(12) United States Patent
Castro Pineiro et al.

(10) Patent No.: US 6,953,792 B2
(45) Date of Patent: Oct. 11, 2005

(54) CYCLOHEXYL DERIVATIVES AND THEIR USE AS THERAPEUTIC AGENTS

(75) Inventors: Jose Luis Castro Pineiro, Bishops Stortford (GB); Kevin Dinnell, Much Hadham (GB); Jason Matthew Elliot, Felsted (GB); Gregory John Hollingworth, Brentwood (GB); Duncan Edward Shaw, Bishops Stortford (GB); Christopher John Swain, Duxford (GB); Lihu Yang, Edison, NJ (US)

(73) Assignees: Merck Sharp & Dohme Limited, Hertfordshire (GB); Merck & Co., Inc., Rahway, NJ (US)

( * ) Notice: Subject to any disclaimer, the term of this patent is extended or adjusted under 35 U.S.C. 154(b) by 55 days.

(21) Appl. No.: 10/276,129

(22) PCT Filed: May 16, 2001

(86) PCT No.: PCT/GB01/02136

§ 371 (c)(1),
(2), (4) Date: Nov. 13, 2002

(87) PCT Pub. No.: WO01/87866

PCT Pub. Date: Nov. 22, 2001

(65) Prior Publication Data

US 2003/0225059 A1 Dec. 4, 2003

(30) Foreign Application Priority Data

May 19, 2000 (GB) ............................................. 0012214

(51) Int. Cl.[7] ...................... A61K 31/495; A61P 25/24; C07D 295/16

(52) U.S. Cl. ...................... 514/217; 514/253; 514/227; 514/235; 514/318; 514/357; 540/597; 544/60; 544/124; 544/360; 546/194; 546/335

(58) Field of Search ........................................ 564/123

(56) References Cited

U.S. PATENT DOCUMENTS

| | | | |
|---|---|---|---|
| 4,611,004 A | | 9/1986 | Ackermann et al. |
| 5,519,034 A | * | 5/1996 | Kozlik et al. ............... 514/307 |
| 5,849,795 A | | 12/1998 | Arcamone et al. |

FOREIGN PATENT DOCUMENTS

| | | |
|---|---|---|
| JP | 59/116243 | 7/1984 |
| WO | WO 00/25770 | 5/2000 |

OTHER PUBLICATIONS

*Chemical Abstracts*, vol. 84, No. 23, Jun. 7, 1976, abstract No. 164575. Markaryan. E. A. et al. Arm. Khim. zh. (1975), 28(10), 829–35.

Steventon et al: *Journal of Medicinal Chemistry*, vol. 41, No. 23, 1998, pp. 4623–4635.

Database Chemcats AsInEx Compound Collection. May 10, 2001. Database accession No. 2002:174244 XP002172980.

* cited by examiner

Primary Examiner—Kamal A. Saeed
(74) Attorney, Agent, or Firm—Curtis C. Panzer; David L. Rose

(57) ABSTRACT

The present invention relates compounds of the formula (I): wherein ring A is a phenyl or pyridyl ring; X represents a linker selected from the group consisting of: (a), (b), (c), (d), (e), (f), (g), (h), (i), (j), (k), (l) and $R^1$, $R^2$, $R^3$, $R^4$, $R^5$, $R^6$, $R^7$, $R^{13}$, $R^{14}$, $R^{15}$, $R^{16}$, R?17, $R^{18}$, $R^{19}$, $R^{21a}$ and $R^{21b}$ are as defined herein. The compounds are of particular use in the treatment or prevention of depression, anxiety, pain, inflammation, migraine, emesis or postherpetic neuralgia.

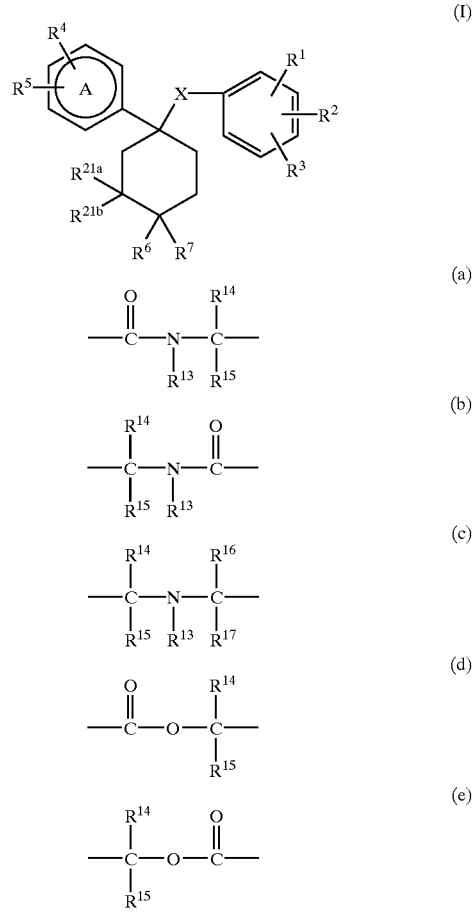

-continued
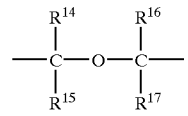
(f)
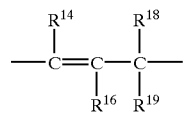
(g)
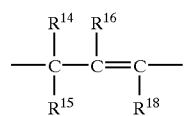
(h)
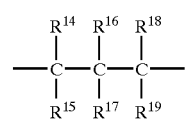
(i)
-continued
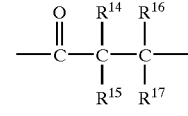
(j)
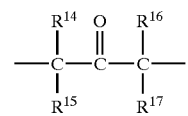
(k)
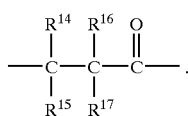
(L)
17 Claims, No Drawings

CYCLOHEXYL DERIVATIVES AND THEIR USE AS THERAPEUTIC AGENTS

CROSS REFERENCE TO RELATED APPLICATIONS

This application is a U.S. National Phase application under 35 U.S.C. § 371 of PCT Application No. PCT/GB01/02136, filed May 16, 2001, which claims priority under 35 U.S.C. § 119 from GB Application No. 0012214.3, filed May 19, 2000.

This invention relates to a class of gem-disubstituted cyclohexane derivatives which are useful as tachykinin antagonists. More particularly, the compounds of the invention are useful as neurokinin 1 (NK-1) receptor antagonists.

The present invention provides compounds of the formula (I):

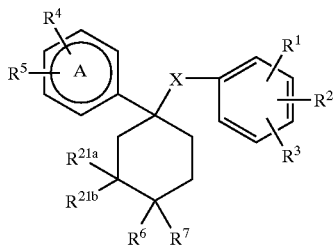

(I)

wherein
ring A is a phenyl or pyridyl ring;
X represents a linker selected from the group consisting of:

(a) $-\overset{O}{\underset{}{C}}-\overset{R^{13}}{\underset{R^{15}}{N}}-\overset{R^{14}}{\underset{}{C}}-$, (b) $-\overset{R^{14}}{\underset{R^{15}}{C}}-\overset{}{\underset{R^{13}}{N}}-\overset{O}{\underset{}{C}}-$, (c) $-\overset{R^{14}}{\underset{R^{15}}{C}}-\overset{}{\underset{R^{13}}{N}}-\overset{R^{16}}{\underset{R^{17}}{C}}-$, (d) $-\overset{O}{\underset{}{C}}-O-\overset{R^{14}}{\underset{R^{15}}{C}}-$, (e) $-\overset{R^{14}}{\underset{R^{15}}{C}}-O-\overset{O}{\underset{}{C}}-$, (f) $-\overset{R^{14}}{\underset{R^{15}}{C}}-O-\overset{R^{16}}{\underset{R^{17}}{C}}-$, (g) $-\overset{R^{14}}{\underset{R^{16}}{C}}=\overset{R^{18}}{\underset{R^{19}}{C}}-\overset{}{\underset{}{C}}-$, (h) $-\overset{R^{14}}{\underset{R^{15}}{C}}-\overset{R^{16}}{\underset{R^{18}}{C}}=\overset{}{\underset{}{C}}-$, (i) $-\overset{R^{14}}{\underset{R^{15}}{C}}-\overset{R^{16}}{\underset{R^{17}}{C}}-\overset{R^{18}}{\underset{R^{19}}{C}}-$, (j) $-\overset{O}{\underset{}{C}}-\overset{R^{14}}{\underset{R^{15}}{C}}-\overset{R^{16}}{\underset{R^{17}}{C}}-$, (k) $-\overset{R^{14}}{\underset{R^{15}}{C}}-\overset{O}{\underset{}{C}}-\overset{R^{16}}{\underset{R^{17}}{C}}-$, and (l) $-\overset{R^{14}}{\underset{R^{15}}{C}}-\overset{R^{16}}{\underset{R^{17}}{C}}-\overset{O}{\underset{}{C}}-$;

$R^1$ represents hydroxy, $C_{1-6}$alkyl, fluoro$C_{1-6}$alkyl, $C_{2-6}$alkenyl, $C_{3-7}$cycloalkyl, $C_{3-7}$cycloalkyl$C_{1-4}$alkyl, $C_{1-6}$alkoxy, fluoro$C_{1-6}$alkoxy, $C_{1-6}$alkoxy$C_{1-4}$alkyl, $C_{1-6}$alkoxy$C_{1-4}$alkoxy, fluoro$C_{1-6}$alkoxy$C_{1-4}$alkyl, $C_{2-6}$alkenyloxy, $C_{3-7}$cycloalkoxy, $C_{3-7}$cycloalkyl$C_{1-4}$alkoxy, phenoxy, cyano, halogen, $NR^aR^b$, $SR^a$, $SOR^a$, $SO_2R^a$, $OSO_2R^a$, $NR^aCOR^c$, $COR^a$, $CO_2R^a$ or $CONR^aR^b$ where $R^a$ and $R^b$ each independently represent hydrogen, $C_{1-4}$alkyl, $C_{3-5}$cycloalkyl, fluoro$C_{1-4}$alkyl or $CH_2CO_2C_{1-4}$alkyl, and $R^c$ represents $C_{1-6}$alkyl, $C_{1-6}$alkoxy, fluoro$C_{1-6}$alkyl or phenyl;

$R^2$ represents hydrogen, halogen, $C_{1-6}$alkyl or $C_{1-6}$alkoxy; or when $R^2$ is adjacent to $R^1$, they may be joined together such that there is formed a 5- or 6-membered saturated or unsaturated ring containing one or two atoms selected from nitrogen, oxygen and sulphur, which ring is optionally substituted by a group selected from $C_{1-4}$alkyl, $CF_3$, =O or =S;

$R^3$ represents hydrogen, halogen, $C_{1-6}$alkyl, fluoro$C_{1-6}$alkyl, $C_{1-6}$alkoxy, fluoro$C_{1-6}$alkoxy, $C_{3-7}$cycloalkyl, $C_{3-7}$cycloalkyl$C_{1-4}$alkyl, cyano, $SR^a$, $SOR^a$, $SO_2R^a$, $NR^aR^b$, $NR^aCOR^{14}$, $COR^a$, $CO_2R^a$, $CONR^aR^b$ or $C_{1-4}$alkyl substituted by cyano, $CO_2R^a$ or $CONR^aR^b$ where $R^a$ and $R^b$ are as previously defined;

or $R^3$ represents a 5- or 6-membered aromatic heterocyclic group containing 1, 2, 3 or 4 heteroatoms, selected from nitrogen, oxygen and sulphur, which group is optionally substituted by one or two groups selected from $C_{1-6}$alkyl, $C_{1-6}$alkoxy, $C_{3-7}$cycloalkyl, $C_{3-7}$cycloalkyl$C_{1-4}$alkyl, trifluoromethyl, $OCF_3$, $NO_2$, $CN$, $SR^a$, $SOR^a$, $SO_2R^a$, $COR^a$, $CO_2R^a$, phenyl, $-(CH_2)_rNR^aR^b$, $-(CH_2)_rNR^aCOR^b$, $-(CH_2)_rCONR^aR^b$, or $CH_2C(O)R^a$, where $R^a$ and $R^b$ are as previously defined and r is zero, 1 or 2;

$R^4$ is hydrogen, halogen, $C_{1-6}$alkyl, $C_{1-6}$alkoxy, fluoro$C_{1-6}$alkyl, fluoro$C_{1-6}$alkoxy, hydroxy, $NO_2$, $CN$, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ are as previously defined;

$R^5$ is hydrogen, halogen, $C_{1-6}$alkyl, fluoro$C_{1-6}$alkyl or $C_{1-6}$alkoxy substituted by $C_{1-4}$alkoxy;

$R^6$ represents hydrogen, hydroxy or a $C_{1-4}$alkyl group optionally substituted by a hydroxy group;

$R^7$ represents hydrogen, hydroxy, —$(CH_2)_nNR^8R^9$, —$(CH_2)_nCO_2R^a$, carbocyclyl, C-linked heterocyclyl or heteroaryl;

or $R^6$ and $R^7$ together represent =O, =CHCO$_2R^a$ or —O(CH$_2)_m$O—;

$R^8$ and $R^9$ each independently represent hydrogen, $C_{1-6}$alkyl, $C_{2-6}$alkenyl, hydroxy$C_{1-6}$alkyl, $(CH_2)_qC_{3-7}$cycloalkyl, $(CH_2)_q$aryl, $(CH_2)_q$heterocyclyl, CHO, C(O)$C_{1-6}$alkyl, C(O)(CH$_2)_qC_{3-7}$cycloalkyl, C(O)(CH$_2)_q$aryl, C(O)(CH$_2)_q$heterocyclyl, C(O)(CH$_2)_p$NR$^a$R$^b$, $(CH_2)_qCO_2C_{1-6}$alkyl, CO$_2$(CH$_2)_qC_{3-7}$cycloalkyl, CO$_2$(CH$_2)_q$aryl, CO$_2$(CH$_2)_q$heterocyclyl, CO$_2$(CH$_2)_p$NR$^a$R$^b$, $(CH_2)_p$NR$^a$COR$^b$, $(CH_2)_p$NR$^a$CO$_2R^b$, $(CH_2)_q$CONR$^a$aryl or $(CH_2)_q$CONR$^a$-heterocyclyl where $R^a$ and $R^b$ are as previously defined;

or $R^8$ and $R^9$, together with the nitrogen atom to which they are attached, represent a heteroaliphatic ring selected from the group consisting of:

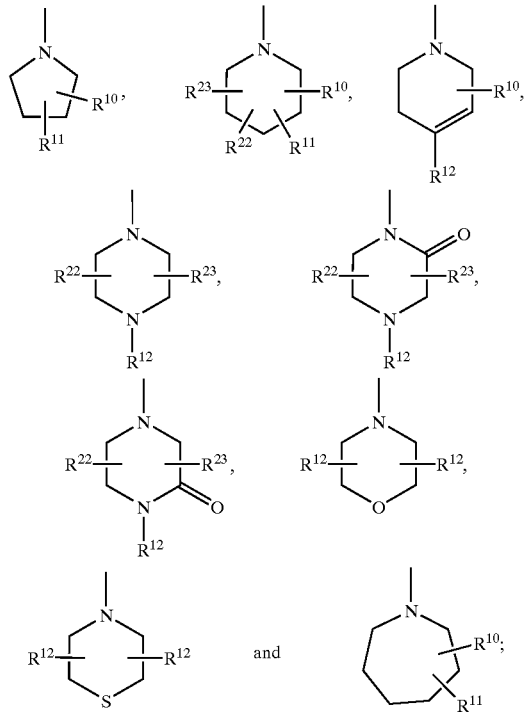

$R^{10}$ and $R^{11}$ each independently represent hydrogen, halogen, hydroxy, $C_{1-6}$alkyl, $C_{2-6}$alkenyl, $C_{2-6}$alkynyl, hydroxy$C_{1-6}$alkyl, fluoro$C_{1-6}$alkyl, $C_{1-6}$alkoxy, $(CH_2)_qC_{3-7}$cycloalkyl, $(CH_2)_q$aryl, $(C_{2-6}$alkenyl)aryl, $(C_{2-6}$alkynyl)aryl, $(CH_2)_q$heterocyclyl, $(CH_2)_q$NR$^a$R$^b$, O(CH$_2)_qC_{3-7}$cycloalkyl, O(CH$_2)_q$aryl, O(CH$_2)_q$heterocyclyl, O(CH$_2)_p$NR$^a$R$^b$, OC(O)C$_{1-6}$alkyl, C(O)C$_{1-6}$alkyl, C(O)(CH$_2)_q$aryl, C(O)(CH$_2)_q$heterocyclyl, C(O)(CH$_2)_q$NR$^a$R$^b$, CO$_2$H, CO$_2C_{1-6}$alkyl, CO$_2$(CH$_2)_qC_{3-7}$cycloalkyl, CO$_2$(CH$_2)_q$aryl, CO$_2$(CH$_2)_q$heterocyclyl or CO$_2$(CH$_2)_p$NR$^a$R$^b$, where $R^a$ and $R^b$ are as previously defined;

or, when they are attached to the same carbon atom, $R^{10}$ and $R^{11}$ may together represent =O, =CHCO$_2R^a$, —O(CH$_2)_m$O—, —CH$_2$O(CH$_2)_s$—, —CH$_2$OCH$_2$C(O)—, —CH$_2$OCH$_2$CH(OH)—, —CH$_2$OCH$_2$C(CH$_3)_2$—, —CH$_2$OC(CH$_3)_2$CH$_2$—, —C(CH$_3)_2$OCH$_2$CH$_2$—, —CH$_2$C(O)OCH$_2$—, —OC(O)CH$_2$CH$_2$—, —C(O)OCH$_2$CH$_2$—, —C(O)OC(CH$_3)_2$CH$_2$—, —C(O)OCH$_2$C(CH$_3)_2$—, —OCH$_2$(CH$_2)_s$—, —OC(CH$_3)_2$CH$_2$CH$_2$—, —OCH$_2$C(CH$_3)_2$CH$_2$—, —OCH$_2$CH$_2$C(CH$_3)_2$—, —OCH$_2$CH=CHCH$_2$—, —OCH$_2$CH(OH)CH$_2$CH$_2$—, —OCH$_2$CH$_2$CH(OH)CH$_2$—, —OCH$_2$C(O)CH$_2$CH$_2$—, —OCH$_2$CH$_2$C(O)CH$_2$—, or a group of the formula

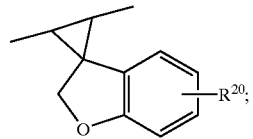

or, where they are attached to adjacent carbon atoms, $R^{10}$ and $R^{11}$ may together represent —OCH$_2$CH$_2$— or —OCH$_2$CH(OH)—, or $R^{10}$ and $R^{11}$ may together form a fused benzene ring;

or, $R^{10}$ and $R^{11}$ together form a $C_{1-2}$alkylene bridge across the pyrrolidine, piperidine or hexamethyleneimine ring to which they are attached;

$R^{12}$ represents hydrogen, $C_{1-6}$alkyl, $(CH_2)_qC_{3-7}$cycloalkyl, $(CH_2)_q$aryl, $(CH_2)_q$heterocyclyl, CHO, C(O)C$_{1-6}$alkyl, C(O)(CH$_2)_qC_{3-7}$cycloalkyl, C(O)(CH$_2)_q$aryl, C(O)(CH$_2)_q$heterocyclyl, CO$_2C_{1-6}$alkyl, CO$_2$(CH$_2)_qC_{3-7}$cycloalkyl, CO$_2$(CH$_2)_q$aryl, CO$_2$(CH$_2)_q$heterocyclyl or CO$_2$(CH$_2)_p$NR$^a$R$^b$, where $R^a$ and $R^b$ are as previously defined;

or, where they are attached to adjacent carbon atoms, $R^{12}$ and $R^{18}$ may together form a fused imidazolyl or triazolyl ring;

$R^{13}$ represents hydrogen, $C_{1-6}$alkyl or C(O)$C_{1-6}$alkyl;

$R^{14}$, $R^{15}$, $R^{16}$, $R^{17}$, $R^{18}$ and $R^{19}$ each independently represent hydrogen, hydroxy, $C_{1-6}$alkyl, $C_{1-6}$alkenyl, hydroxy$C_{1-6}$alkyl, $C_{1-4}$alkoxy$C_{1-4}$alkyl, $(CH_2)_p$NR$^a$R$^b$, CHO, C(O)C$_{1-6}$alkyl or CO$_2C_{1-6}$alkyl;

or, $R^{14}$ and $R^{15}$ together represent —CH$_2$CH$_2$—;

or, $R^{16}$ and $R^{17}$ together represent —CH$_2$CH$_2$—;

or, $R^{18}$ and $R^{19}$ together represent —CH$_2$CH$_2$—;

$R^{20}$ represents hydrogen, halogen, hydroxy, $C_{1-4}$alkyl, hydroxy$C_{1-4}$alkyl or fluoro$C_{1-4}$alkyl;

$R^{21a}$ represents hydrogen, halogen or hydroxy and $R^{21b}$ represents hydrogen;

or $R^{21a}$ and $R^{21b}$ both represent fluorine or together represent oxo (=O);

$R^{22}$ and $R^{23}$ each independently represent hydrogen, halogen, hydroxy, $C_{1-6}$alkyl or oxo (=O);

n is zero, 1 or 2;

m is 1 or 2;

p is 1, 2,3 or 4;

q is zero, 1, 2, 3 or 4; and s is 1, 2 or 3;

and pharmaceutically acceptable salts and N-oxides thereof.

According to an alternative embodiment, the present invention also provides compounds of the formula (I'):

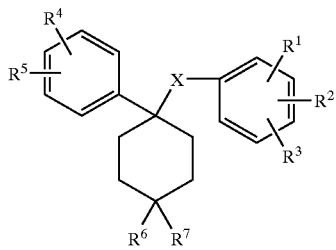

wherein $R^6$ represents hydrogen or a $C_{1-4}$alkyl group optionally substituted by a hydroxy group;

$R^7$ represents hydrogen, hydroxy, —$(CH_2)_nNR^8R^9$, —$(CH_2)_nCO_2R^a$, carbocyclyl or heteroaryl;

or $R^6$ and $R^7$ together represent =O, =CHCO$_2$R$^a$ or —O(CH$_2$)$_m$O—;

$R^8$ and $R^9$ each independently represent hydrogen, $C_{1-6}$alkyl, $C_{2-6}$alkenyl, $(CH_2)_qC_{3-7}$cycloalkyl, $(CH_2)_q$aryl, $(CH_2)_q$heterocyclyl, CHO, C(O)C$_{1-6}$alkyl, C(O)(CH$_2$)$_qC_{3-7}$cycloalkyl, C(O)(CH$_2$)$_q$aryl, C(O)(CH$_2$)$_q$heterocyclyl, C(O)(CH$_2$)$_qNR^aR^b$, $(CH_2)_qCO_2C_{1-6}$alkyl, CO$_2$(CH$_2$)$_qC_{3-7}$cycloalkyl, CO$_2$(CH$_2$)$_q$aryl, CO$_2$(CH$_2$)$_q$heterocyclyl, CO$_2$(CH$_2$)$_pNR^aR^b$, (CH$_2$)$_pNR^aCOR^b$ or (CH$_2$)$_pNR^aCO_2R^b$, where $R^a$ and $R^b$ are as previously defined;

or $R^8$ and $R^9$, together with the nitrogen atom to which they are attached, represent a heteroaliphatic ring selected from the group consisting of:

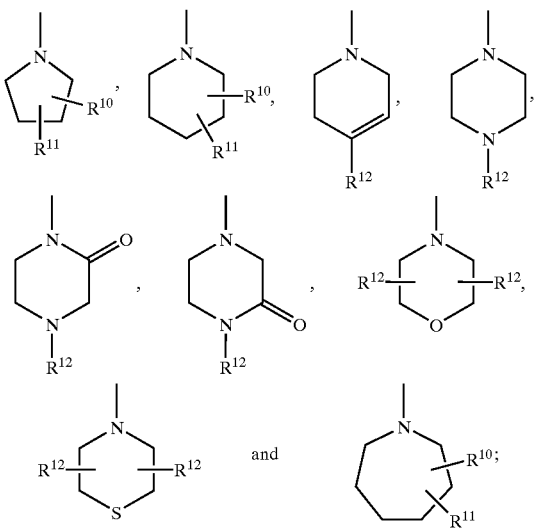

$R^{10}$ and $R^{11}$ each independently represent hydrogen, halogen, hydroxy, $C_{1-6}$alkyl, $C_{2-6}$alkenyl, $C_{2-6}$alkynyl, hydroxyC$_{1-6}$alkyl, $C_{1-6}$alkoxy, $(CH_2)_qC_{3-7}$cycloalkyl, $(CH_2)_q$ aryl, $(C_{2-6}$alkenyl)aryl, $(C_{2-6}$alkynyl)aryl, $(CH_2)_q$heterocyclyl, $(CH_2)_qNR^aR^b$, O(CH$_2$)$_qC_{3-7}$cycloalkyl, O(CH$_2$)$_q$aryl, O(CH$_2$)$_q$heterocyclyl, O(CH$_2$)$_pNR^aR^b$, OC(O)C$_{1-6}$alkyl, C(O)C$_{1-6}$alkyl, C(O)(CH$_2$)$_q$aryl, C(O)(CH$_2$)$_q$heterocyclyl, C(O)(CH$_2$)$_qNR^aR^b$, CO$_2$H, CO$_2$C$_{1-6}$alkyl, CO$_2$(CH$_2$)$_qC_{3-7}$cycloalkyl, CO$_2$(CH$_2$)$_q$aryl, CO$_2$(CH$_2$)$_q$heterocyclyl or CO$_2$(CH$_2$)$_pNR^aR^b$, where $R^a$ and $R^b$ are as previously defined;

or, when they are attached to the same carbon atom, $R^{10}$ and $R^{11}$ together represent =O, =CHCO$_2$R$^a$, —O(CH$_2$)$_m$O—, —OCH$_2$CH$_2$CH$_2$—, —CH$_2$OCH$_2$CH$_2$— or —CH$_2$OCH$_2$C(O)—;

or, where they are attached to adjacent carbon atoms, $R^{10}$ and $R^{11}$ together form a fused benzene ring;

or, $R^{10}$ and $R^{11}$ together form a $C_{1-2}$alkylene bridge across the pyrrolidine, piperidine or hexamethyleneimine ring to which they are attached;

$R^{12}$ represents hydrogen, $C_{1-6}$alkyl, $(CH_2)_qC_{3-7}$cycloalkyl, $(CH_2)_q$aryl, $(CH_2)_q$heterocyclyl, CHO, C(O)C$_{1-6}$alkyl, C(O)(CH$_2$)$_qC_{3-7}$cycloalkyl, C(O)(CH$_2$)$_q$aryl, C(O)(CH$_2$)$_q$heterocyclyl, CO$_2$C$_{1-6}$alkyl, CO$_2$(CH$_2$)$_qC_{3-7}$cycloalkyl, CO$_2$(CH$_2$)$_q$aryl, CO$_2$(CH$_2$)$_q$heterocyclyl or CO$_2$(CH$_2$)$_pNR^aR^b$, where $R^a$ and $R^b$ are as previously defined;

$R^{14}$, $R^{15}$, $R^{16}$, $R^{17}$, $R^{18}$ and $R^{19}$ each independently represent hydrogen, hydroxy, $C_{1-6}$alkyl, $C_{1-6}$alkenyl, hydroxyC$_{1-6}$alkyl, $(CH_2)_pNR^aR^b$, CHO, C(O)C$_{1-6}$alkyl or CO$_2$C$_{1-6}$alkyl;

and X, $R^1$, $R^2$, $R^3$, $R^4$, $R^5$, $R^{13}$, n, m, p and q are as defined in relation to formula (I);

and pharmaceutically acceptable salts thereof.

A preferred class of compound of formula (I) is that wherein $R^1$ is hydroxy, $C_{1-6}$alkyl, fluoroC$_{1-6}$alkyl, $C_{2-6}$alkenyl, $C_{1-6}$alkoxy, fluoroC$_{1-6}$alkoxy, $C_{2-6}$alkenyloxy, $C_{3-7}$cycloalkoxy, $C_{3-7}$cycloalkylC$_{1-4}$alkoxy, cyano, NR$^a$R$^b$, SR$^a$, OSO$_2$R$^a$, or $R^1$ together with the group $R^2$ form a 5-membered saturated ring containing one oxygen atom.

A particularly preferred class of compound of formula (I) is that wherein $R^1$ is $C_{1-6}$alkyl, fluoroC$_{1-6}$alkyl, $C_{1-6}$alkoxy, fluoroC$_{1-6}$alkoxy, $C_{3-7}$cycloalkoxy or $C_{3-7}$cycloalkoxyC$_{1-4}$alkyl, especially methyl, trifluoromethyl, methoxy, trifluoromethoxy, 2,2,2-trifluoroethoxy, difluoromethoxy, cyclopropoxy or cyclopropylmethoxy.

Another preferred class of compound of formula (I) is that wherein $R^2$ is a hydrogen, fluorine or chlorine atom, especially a hydrogen atom.

A further preferred class of compound of formula (I) is that wherein $R^3$ is hydrogen, halogen, fluoroC$_{1-6}$alkyl, fluoroC$_{1-6}$alkoxy, cyano, NR$^a$R$^b$, NR$^a$COR$^d$ (where R$^d$ is methyl, methoxy, trifluoromethyl or phenyl), or a 5-membered aromatic heterocyclic group as previously defined.

Also preferred is the class of compound of formula (I) in which $R^3$ is $C_{1-6}$alkyl, fluoroC$_{1-6}$alkyl, fluoroC$_{1-6}$alkoxy or a 5-membered aromatic heterocyclic group as previously defined, especially methyl, trifluoromethyl, trifluoromethoxy or 5-trifluoromethyl-1,2,3,4tetrazol-1-yl.

Certain particularly apt compounds of the present invention include those wherein $R^3$ is a group selected from pyrrole, furan, thiene, pyridine, pyrazole, imidazole, oxazole, isoxazole, thiazole, isothiazole, pyrazine, pyrimidine, pyridazine, triazole, oxadiazole, thiadiazole, triazine, and tetrazole, each heteroaryl group being optionally substituted as previously defined.

Preferred compounds of the present invention are those wherein $R^3$ is a group selected from furan, pyridine, pyrazole, imidazole, oxazole, isoxazole, pyrazine, pyrimidine, thiazole, 1,2,3-triazole, 1,2,4-triazole, 1,2,4-oxadiazole, 1,3,4-oxadiazole and tetrazole, each heteroaryl group being optionally substituted as previously defined.

Particularly preferred compounds of the present invention are those wherein $R^3$ is a group selected from furan, pyridine, pyrimidine, 1,2,3-triazole, 1,2,4-triazole and tetrazole, each heteroaryl group being optionally substituted as previously defined.

An especially preferred class of compound of formula (I) is that wherein $R^3$ is the group

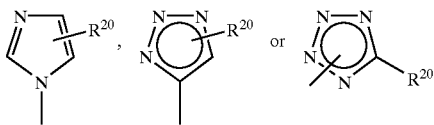

where $R^{20}$ is hydrogen, halogen, $C_{1-6}$alkyl, $C_{1-6}$alkoxy, $CF_3$, $OCF_3$, $NO_2$, CN, $SR^a$, $SOR^a$, $SO_2R^a$, $COR^a$, $CO_2R^a$, $(CH_2)_r CONR^aR^b$, $(CH_2)_rNR^aR^b$ or $(CH_2)_rNR^aCOR^b$, where $R^a$, $R^b$ and r are as previously defined.

$R^{20}$ is preferably hydrogen, $C_{1-4}$alkyl, especially methyl, $CF_3$, $(CH_2)_rCONR^aR^b$, $SOR^a$ or $SO_2R^a$ where $R^a$ and $R^b$ are preferably hydrogen, $C_{1-4}$alkyl or fluoro$C_{1-4}$alkyl and r is as previously defined. Most especially, $R^{20}$ is $CF_3$.

Preferably $R^1$ and $R^3$ are in the 3 and 5 positions of the phenyl ring.

More preferably $R^1$ is 3-fluoro or 3-$CF_3$.

More preferably $R^3$ is 5-fluoro or 5-$CF_3$.

More preferably $R^2$ is hydrogen.

Most preferably $R^1$ is 3-$CF_3$, $R^2$ is hydrogen and $R^3$ is 5-$CF_3$.

Another preferred class of compounds of formula (I) is that wherein $R^1$ and $R^3$ are in the 2- and 5-positions of the phenyl ring.

In this sub-class of compounds of formula (I), $R^1$ is preferably $C_{1-6}$alkoxy or $C_{3-7}$cycloalkoxy, especially methoxy or cyclopropoxy.

Also in this sub-class of compounds of formula (I), $R^2$ is preferably hydrogen.

Also in this sub-class of compounds of formula (I) $R^3$ is preferably hydrogen, $C_{1-6}$alkoxy, fluoro$C_{1-6}$alkoxy or a 5-membered aromatic heterocyclic group as previously defined. Most especially, $R^3$ is hydrogen, methoxy or trifluoromethoxy.

A further preferred class of compound of formula (I) is that wherein $R^4$ is hydrogen.

Another preferred class of compounds of formula (I) is that wherein $R^5$ is hydrogen, fluorine, chlorine or $CF_3$, especially hydrogen or fluorine.

Preferably $R^4$ is hydrogen and $R^5$ is hydrogen or 4fluoro.

Another further preferred class of compounds of formula (I) is that wherein $R^6$ is hydrogen.

A further preferred class of compounds of formula (I) is that wherein $R^7$ is hydroxy, —$(CH_2)_nNR^8R^9$, a C-linked heterocyclyl group or $R^6$ and $R^7$ together represent =O, —$O(CH_2)_mO$— or —$CH_2OCH_2C(O)$—.

Another preferred class of compounds of formula (I) is that wherein $R^7$ is hydroxy or —$(CH_2)_nNR^8R^9$, or $R^6$ and $R^7$ together represent =O, —$O(CH_2)_mO$— or —$CH_2OCH_2 (O)$—.

A further preferred class of compounds of formula (I) is that wherein $R^8$ represents hydrogen, $C_{1-6}$alkyl, $C_{2-6}$alkenyl, hydroxy$C_{1-6}$alkyl, $(CH_2)_qC_{3-7}$cycloalkyl, $(CH_2)_q$aryl, $(CH_2)_q$ heterocyclyl, $C(O)C_{1-6}$alkyl, $C(O)(CH_2)_q$aryl, $C(O)(CH_2)_q$ heterocyclyl, $C(O)(CH_2)_pNR^aR^b$, $(CH_2)_qCO_2C_{1-6}$alkyl, $(CH_2)_pNR^aCO_2R^b$ or $(CH_2)_qCONR^a$aryl;

and $R^9$ represents hydrogen, $C_{1-6}$alkyl, $(CH_2)_qC_{3-7}$ cycloaklyl or $CO_2C_{1-6}$alkyl;

or $R^8$ and $R^9$ together with the nitrogen atom to which they are attached represent a heteroaliphatic ring selected from the group consisting of

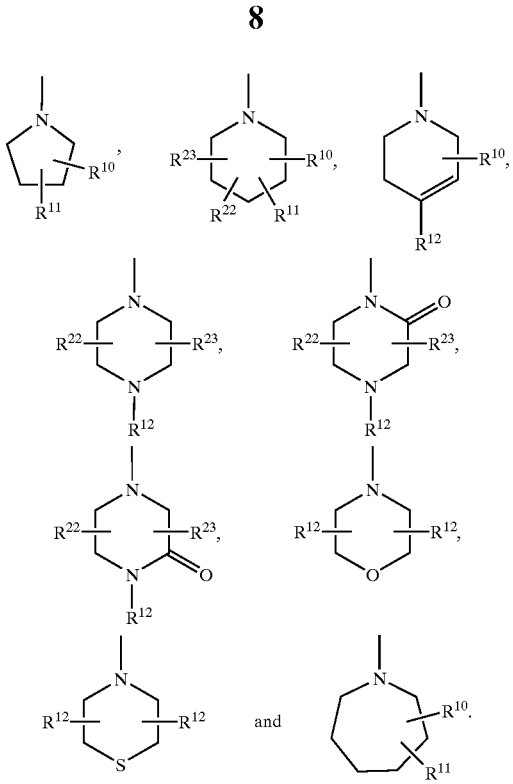

A yet further preferred class of compounds of formula (I) is that wherein $R^8$ represents hydrogen, $C_{1-6}$alkyl, $C_{2-6}$alkenyl, $(CH_2)_qC_{3-7}$cycloalkyl, $(CH_2)_q$aryl, $(CH_2)_q$ heterocyclyl, $C(O)C_{1-6}$alkyl, $C(O)(CH_2)_q$aryl, $C(O)(CH_2)_q$ heterocyclyl, $C(O)(CH_2)_pNR^aR^b$, $(CH_2)_qCO_2C_{1-6}$alkyl or $(CH_2)_pNR^aCO_2R^b$;

and $R^9$ represents hydrogen, $C_{1-6}$alkyl, $(CH_2)_qC_{3-7}$ cycloalkyl or $CO_2C_{1-6}$alkyl;

or $R^8$ and $R^9$ together with the nitrogen atom to which they are attached represent a heteroaliphatic ring selected from the group consisting of

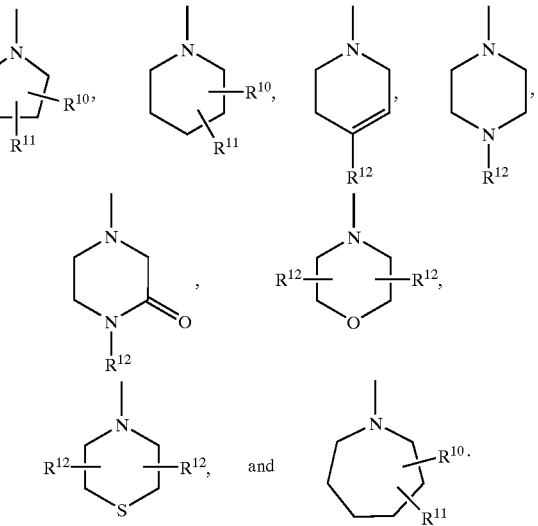

A further preferred class of compounds of formula (I) is that wherein $R^{10}$ represents hydrogen, hydroxy, $C_{1-6}$alkyl, $C_{2-6}$alkenyl, $C_{2-6}$alkynyl, hydroxy$C_{1-6}$alkyl, fluoro$C_{1-6}$ alkyl, $(C_{2-6}$alkynyl)aryl, $(CH_2)_q$aryl, $(CH_2)_q$heterocyclyl, $(CH_2)_qNR^aR^b$, $OC(O)C_{1-6}alkyl$, $C(O)(CH_2)_qNR^aR^b$, $CO_2H$ or $CO_2C_{1-6}alkyl$;

and $R^{11}$ represents hydrogen, halogen, hydroxy, $C_{1-6}alkyl$ or $(CH_2)_qNR^aR^b$;

or when they are attached to the same carbon atom, $R^{10}$ and $R^{11}$ may together represent =O, —O(CH$_2$)$_m$O—, —CH$_2$O(CH$_2$)$_s$—, —CH$_2$OCH$_2$C(O)—, —CH$_2$OCH$_2$CH(OH)—, —CH$_2$OCH$_2$C(CH$_3$)$_2$—, —CH$_2$OC(CH$_3$)$_2$CH$_2$—, —C(CH$_3$)$_2$OCH$_2$CH$_2$—, —CH$_2$C(O)OCH$_2$—, —OC(O)CH$_2$CH$_2$—, —C(O)OCH$_2$CH$_2$—, —C(O)OC(CH$_3$)$_2$CH$_2$—, —C(O)OCH$_2$C(CH$_3$)$_2$—, —OCH$_2$(CH$_2$)$_s$—, —OC(CH$_3$)$_2$CH$_2$CH$_2$—, —OCH$_2$CH=CHCH$_2$—, —OCH$_2$CH(OH)CH$_2$CH$_2$—, —OCH$_2$CH$_2$CH(OH)CH$_2$—, —OCH$_2$C(O)CH$_2$CH$_2$—, or a group of the formula

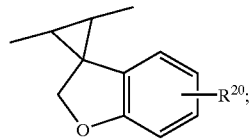

or, when they are attached to adjacent carbon atoms, $R^{10}$ and $R^{11}$ may together represent —OCH$_2$CH$_2$— or —OCH$_2$CH(OH)—, or $R^{10}$ and $R^{11}$ may together form a fused benzene ring;

or $R^{10}$ and $R^{11}$ together form a $C_{1-2}$alkylene bridge across the pyrrolidine or piperidine ring to which they are attached.

Another preferred class of compounds of formula (I) is that wherein $R^{10}$ represents hydrogen, hydroxy, $C_{1-6}$alkyl, $C_{2-6}$alkenyl, $C_{2-6}$alkynyl, hydroxy$C_{1-6}$alkyl, $(C_{2-6}$alkynyl)aryl, $(CH_2)_q$aryl, $(CH_2)_q$heterocyclyl, $(CH_2)_qNR^aR^b$, $OC(O)C_{1-6}$alkyl, $C(O)(CH_2)_qNR^aR^b$, $CO_2H$ or $CO_2C_{1-6}$alkyl;

and $R^{11}$ represents hydrogen, halogen, hydroxy, $C_{1-6}$alkyl or $(CH_2)_qNR^aR^b$;

or when they are attached to the same carbon atom, $R^{10}$ and $R^{11}$ together represent =O or —O(CH$_2$)$_m$O—;

or, when they are attached to adjacent carbon atoms, $R^{10}$ and $R^{11}$ together form a fused benzene ring, or $R^{10}$ and $R^{11}$ together form a $C_{1-2}$alkylene bridge across the pyrrolidine or piperidine ring to which they are attached.

A further preferred class of compounds of formula (I) is that wherein $R^{12}$ represents hydrogen, $C_{1-6}$alkyl, $(CH_2)_qC_{3-7}$cycloalkyl, $(CH_2)_q$aryl, $(CH_2)_q$heterocyclyl, CHO, $C(O)C_{1-6}$alkyl, $C(O)C_{3-7}$cycloalkyl, $C(O)(CH_2)_q$aryl or $CO_2C_{1-6}$alkyl.

A yet further prefered class of compounds of formula (I) is that wherein $R^9$ represents hydrogen, $C_{1-6}$alkyl, $(CH_2)_qC_{3-7}$cycloalkyl or $CO_2C_{1-6}$alkyl.

A particularly preferred class of compounds of formula (I) is that wherein $R^8$ represents hydrogen, $C_{1-6}$alkyl, $C_{2-4}$alkenyl, $C_{3-7}$cycloalkyl, $CH_2C_{3-7}$cycloalkyl, $(CH_2)_q$phenyl, $(CH_2)_q$furyl, $(CH_2)_q$pyridyl, $(CH_2)_q$triazolinone, $C(O)C_{1-4}$alkyl, $C(O)(CH_2)_q$phenyl, $C(O)(CH_2)_q$imidazolyl, $C(O)(CH_2)_q$tetrazolyl, $C(O)(CH_2)$pyrrolidinyl, $C(O)(CH_2)_p$NR$^a$R$^b$, $CH_2C(O)C_{1-4}$alkyl or $(CH_2)_pNR^aCO_2C_{1-4}$alkyl;

and $R^9$ represents hydrogen, $C_{1-6}$alkyl, $CH_2C_{3-5}$cycloalkyl or $CO_2C_{1-4}$alkyl;

or $R^8$ and $R^9$ together with the nitrogen atom to which they are attached represent a heteroaliphatic ring selected from the group consisting of:

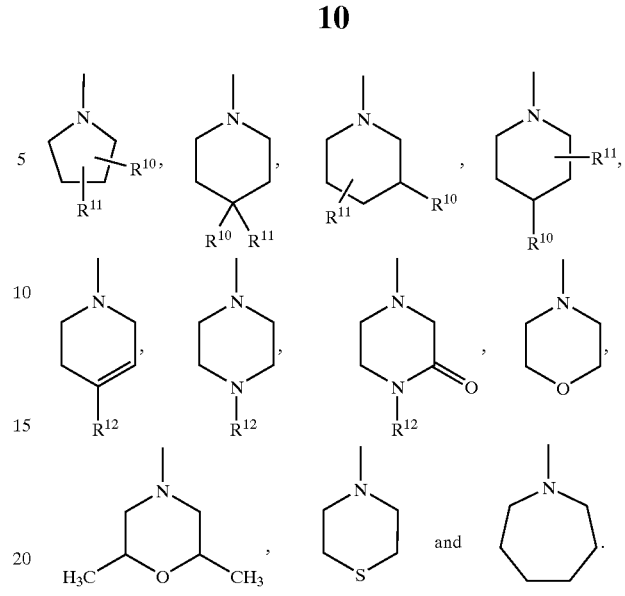

A further particularly preferred class of compounds of formula (I) is that wherein:

$R^{10}$ represents hydrogen, hydroxy, methyl, allyl, acetylene, hydroxy$C_{1-4}$alkyl, —C≡C(phenyl), phenyl, 4-fluorophenyl, CH$_2$phenyl, CH$_2$CH$_2$phenyl, heterocyclyl (wherein said heterocyclyl is selected from the group consisting of pyrrolidinyl, piperidinyl, piperazinyl, morpholinyl, thiomorpholinyl, and hexamethyleneimine, wherein each ring is optionally substituted by one or two groups selected from methyl, hydroxymethyl, cyclohexyl, dimethylamino and benzisothiazole or there is optionally a benzene ring fused to the ring, or there is optionally present a —CH$_2$CH$_2$— bridge across the ring), NR$^a$R$^b$, OC(O)CH$_3$, C(O)NR$^a$R$^b$, CO$_2$H or CO$_2$C$_{1-4}$alkyl; and $R^{11}$ represents hydrogen, fluorine, hydroxy, methyl or dimethylamino;

or, when they are attached to the same carbon atom, $R^{10}$ and $R^{11}$ together represent =O or —OCH$_2$CH$_2$O—;

or, when they are attached to adjacent carbon atoms, $R^{10}$ and $R^{11}$ together form a fused benzene ring;

or, $R^{10}$ and $R^{11}$ together form a —CH$_2$CH$_2$— bridge across the pyrrolidine or piperidine ring to which they are attached.

A yet further particularly preferred class of compounds of formula (I) is that wherein $R^{12}$ represents hydrogen, $C_{1-6}$alkyl, $C_{3-6}$cycloalkyl, CH$_2$C$_{3-6}$cycloalkyl (especially CH$_2$cyclopropyl or CH$_2$cyclohexyl), phenyl, CH$_2$phenyl, CH$_2$CH$_2$phenyl (wherein each of said phenyl groups are optionally substituted by one or two substituents selected from fluorine, CF$_3$ or methoxy), CH$_2$heterocyclyl (wherein said heterocyclyl is selected from the group consisting of 2-, 3- or 4-pyridine, 2- or 3-thiophene, 2- or 3-furan, thiazole, and benzisothiazole), CHO, C(O)C$_{1-4}$alkyl, C(O)C$_{3-6}$cycloalkyl (especially C(O)cyclopropyl or C(O)cyclohexyl), C(O)CH$_2$cycloalkyl (especially C(O)CH$_2$cyclopropyl or C(O)CH$_2$cyclohexyl), C(O)CH$_2$CH$_2$C$_{3-6}$cycloalkyl (especially C(O)CH$_2$CH$_2$cyclohexyl), C(O)phenyl or CO$_2$C$_{1-4}$alkyl.

Yet another particularly preferred class of compounds of formula (I) is that wherein $R^9$ represents hydrogen, $C_{1-6}$alkyl, CH$_2$C$_{3-5}$cycloalkyl or CO$_2$C$_{1-4}$alkyl.

Another preferred class of compound of formula (I) is that wherein the ring A is a phenyl ring.

Particularly preferred compounds of formula (I) are those wherein $R^7$ represents a group selected from:

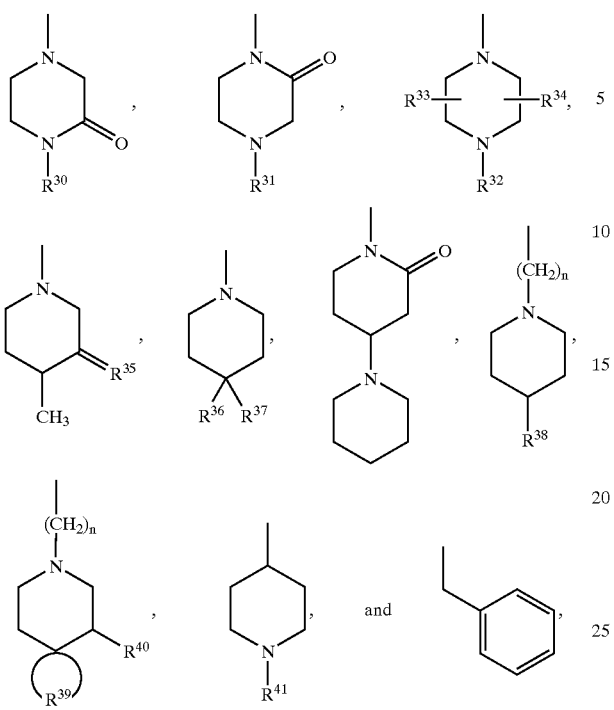

wherein

R³⁰ represents 4-pyridyl, phenyl, phenyl mono-substituted by fluorine, chlorine, methyl, methoxy or CO₂methoxy, or phenyl disubstituted by methyl;

R³¹ represents $C_{2-4}$alkyl or $(CH_2)_qC_{3-7}$cycloalkyl, especially tert-butyl, cyclopropylmethyl or cyclohexyl;

R³² represents $C_{1-6}$alkyl, tetrahydropyranyl or benzyl;

R³³ and R³⁴, which may be attached to the same or different carbon atoms, each independently represent hydrogen or methyl;

R³⁵ represents hydroxy or methoxy;

R³⁶ represents hydroxy$C_{1-4}$alkyl (especially hydroxymethyl), $C_{1-4}$alkoxy (especially methoxy) or hydroxy;

R³⁷ represents methoxy $C_{2-4}$alkyl (especially methoxymethyl) or $C_{2-4}$alkyl;

R³⁸ represents hydrogen, oxo (=O), hydroxy, trifluoromethyl, $C_{1-3}$alkyl (especially isopropyl) or hydroxy$C_{1-3}$alkyl (especially hydroxymethyl or hydroxyethyl);

R³⁹ represents a ring-forming moiety selected from —OCH₂CH₂O—, —CH₂OCH₂CH₂—, —CH₂OCH₂CH₂CH₂—, —CH₂OCH₂C(O)—, —CH₂OCH₂CH(OH)—, —CH₂OC(CH₃)₂CH₂—, —C(CH₃)₂OCH₂CH—, —CH₂C(O)OCH₂—, —C(O)OCH₂CH₂—, —C(O)OC(CH₃)₂CH₂—, —OCH₂CH₂CH₂—, —OCH₂CH₂CH₂CH₂—, —OC(CH₃)₂CH₂CH₂—, —OCH₂CH=CHCH₂—, —OCH₂CH(OH)CH₂CH₂—, —OCH₂CH₂CH(OH)CH₂—, —OCH₂C(O)CH₂CH₂ and a group of the formula

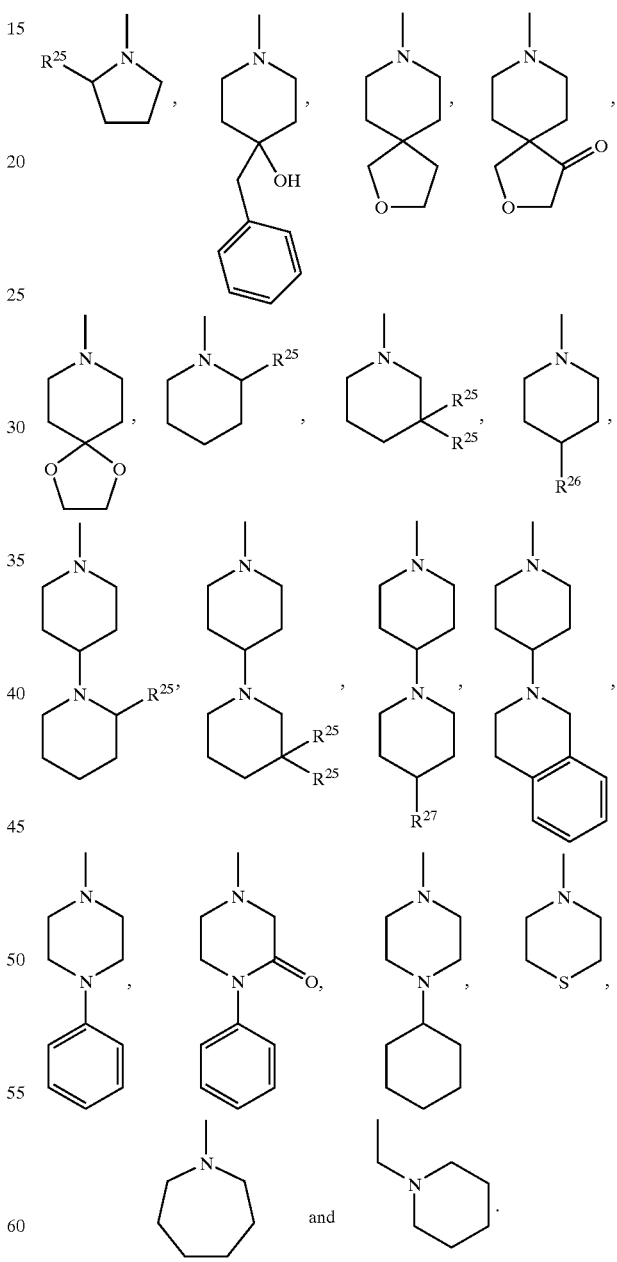

R⁴⁰ is hydrogen or hydroxy, especially hydrogen;
R⁴¹ is $C_{1-3}$alkyl, especially isopropyl; and
n is zero, 1 or 2, especially zero.

Further preferred compounds of formula (I) are those wherein R⁷ represents a group selected from:

wherein
R²⁵ represents hydrogen, methyl or hydroxymethyl;
R²⁶ represents hydrogen, methyl, hydroxy, methylamino, dimethylamino, cyclopropylamino, phenyl, or phenyl substituted by fluorine; and $R^{27}$ represents hydrogen, methyl, hydroxy, methylamirno, dimethylamino or cyclopropylamino.

Another preferred class of compounds of formula (I) is that wherein $R^{21a}$ represents hydrogen, fluorine or hydroxy and $R^{21b}$ is hydrogen, or $R^{21a}$ and $R^{21b}$ both represent fluorine or together represent oxo (=O). In particular, $R^{21a}$ is preferably hydrogen, fluorine or hydroxy and $R^{21b}$ is hydrogen. Most especially, $R^{21a}$ and $R^{21b}$ are preferably both hydrogen.

Another preferred class of compounds of formula (I) is that wherein X represents a linker selected from:

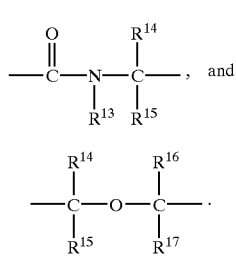

Another preferred class of compounds of formula (I) is that wherein $R^{13}$ represents hydrogen, methyl or acetyl. In particular, $R^{13}$ represents hydrogen.

A further preferred class of compounds of formula (I) is that wherein one of the groups $R^{14}$, $R^{15}$, $R^{16}$ and $R^{17}$ represents hydrogen, hydroxy, $C_{1-6}$alkyl, hydroxy$C_{1-6}$alkyl, $(CH_2)_pNR^aR^b$, CHO, $C(O)C_{1-6}$alkyl or $CO_2C_{1-6}$alkyl, and the other(s) of the groups $R^{14}$, $R^{15}$, $R^{16}$ and $R^{17}$ each represent hydrogen.

A particularly preferred class of compounds of formula (I) is that wherein one of the groups $R^{14}$, $R^{15}$, $R^{16}$ and $R^{17}$ represents methyl or hydroxymethyl, and the other(s) of groups $R^{14}$, $R^{15}$, $R^{16}$ and $R^{17}$ each represent hydrogen.

A further preferred class of compounds of formula (I) is that wherein $R^{18}$ and $R^{19}$ each independently represent hydrogen or methyl.

Most especially, a preferred class of compounds of formula (I) is that wherein X represents a linker selected from:

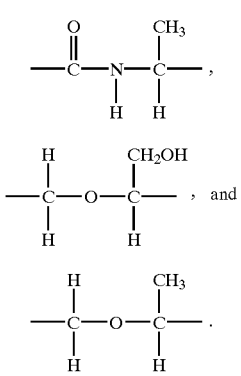

Another preferred class of compounds of formula (I) is that wherein n is zero.

A further preferred class of compounds of formula (I) is that wherein m is 2.

Another preferred class of compounds of formula (I) is that wherein p is 1, 2 or 3, particularly 1 or 2, and especially 1.

A further preferred class of compounds of formula (I) is that wherein q is zero, 1 or 2, particularly zero or 1.

One favoured group of compounds of the present invention are of the formula (Ia) and pharmaceutically acceptable salts thereof:

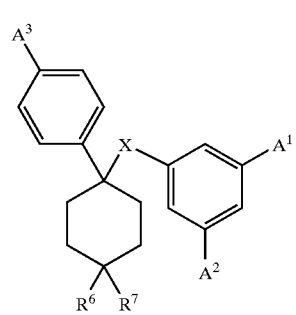

wherein
$A^1$ is fluorine or $CF_3$;
$A^2$ is fluorine or $CF_3$;
$A^3$ is fluorine or hydrogen;
$R^6$ and $R^7$ are as defined in relation to formula (I); and
X is a linker selected from:

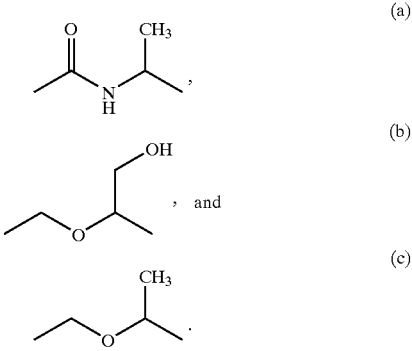

When any variable occurs more than one time in formula (I) or formula (Ia) or in any substituent, its definition on each occurrence is independent of its definition at every other occurrence.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

As used herein, the term "hydroxy$C_{1-6}$alkyl" means a $C_{1-6}$alkyl group in which one or more (in particular 1 to 3, and especially 1) hydrogen atoms have been replaced by hydroxy groups. Particularly preferred are hydroxy$C_{1-3}$alkyl groups, for example, $CH_2OH$, $CH_2CH_2OH$, $CH(CH_3)OH$ or $C(CH_3)_2OH$, and most especially $CH_2OH$.

As used herein, the terms "fluoro$C_{1-6}$alkyl" and "fluoro$C_{1-6}$alkoxy" means a $C_{1-6}$alkyl or $C_{1-6}$alkoxy group in which one or more (in particular, 1 to 3) hydrogen atoms have been replaced by fluorine atoms. Particularly preferred are fluoro$C_{1-3}$alkyl and fluoro$C_{1-3}$alkoxy groups, for example, $CF_3$, $CH_2CH_2F$, $CH_2CHF_2$, $CH_2CF_3$, $OCF_3$, $OCH_2CH_2F$, $OCH_2CHF_2$ or $OCH_2CF_3$, and most especially $CF_3$, $OCF_3$ and $OCH_2CF_3$.

The cycloalkyl groups referred to herein may represent, for example, cyclopropyl, cyclobutyl, cyclopentyl or cyclohexyl. A suitable $(CH_2)_qC_{3-7}$cycloalkyl group where q is 1 may be, for example, cyclopropylmethyl or cyclohexylmethyl.

Similarly cycloalkoxy groups referred to herein may represent, for example, cyclopropoxy or cyclobutoxy.

As used herein, the terms "alkenyl" and "alkynyl" as a group or part of a group means that the group is straight or branched. Examples of suitable alkenyl groups include vinyl and allyl. A suitable alkynyl group is acetylene or propargyl.

When used herein the term "halogen" means fluorine, chlorine, bromine and iodine. The most apt halogens are fluorine and chlorine of which fluorine is preferred, unless otherwise stated.

As used herein, the term "aryl" as a group or part of a group means an aromatic radical such as phenyl, biphenyl or naphthyl, wherein said phenyl, biphenyl or naphthyl group may be optionally substituted by one, two or three groups independently selected from halogen, $C_{1-6}$alkyl, $C_{1-6}$alkoxy, fluoro$C_{1-6}$alkyl, fluoro$C_{1-6}$alkoxy, $NO_2$, cyano, $SR^a$, $SOR^a$, $SO_2R^a$, $COR^a$, $CO_2R^a$, $CONR^aR^b$, $C_{2-6}$alkenyl, $C_{2-6}$alkynyl, $C_{1-4}$alkoxy$C_{1-4}$alkyl or —$O(CH_2)_mO$—. Preferably said phenyl, biphenyl or naphthyl group is optionally substituted by one or two substituents, especially none or one. Particularly preferred substituents include fluorine, chlorine, bromine, $C_{1-4}$alkyl (especially methyl), $C_{1-4}$alkoxy (especially methoxy), trifluoromethyl, trifluormethoxy or vinyl.

As used herein, the term "heterocyclyl" as a group or part of a group means a saturated, partially saturated or unsaturated heteroatom-containing ring-shaped radical, where the heteroatoms may be selected from nitrogen, oxygen and sulfur. Examples of saturated heterocyclyl radicals include N-linked saturated 3 to 6-membered heteromonocyclic groups containing 1 to 3 nitrogen atoms and optionally 1 oxygen or sulfur atom (for example, azetidinyl, pyrrolidinyl, piperidinyl, morpholinyl, thiomorpholinyl, piperazinyl or piperazinyl substituted on the nitrogen atom by a $C_{1-4}$alkyl group or a $C_{2-4}$alkyl group substituted by hydroxy or $C_{1-2}$alkoxy). Examples of saturated heterocyclyl radicals also include C-linked saturated 3 to 6-membered heteromonocyclic groups containing, for example, one oxygen atom (for instance, tetrahydrofuranyl or tetrahydropyranyl). Examples of partially saturated heterocyclyl radicals include N-linked partially saturated 3 to 6-membered heteromonocyclic groups containing 1 to 3 nitrogen atoms (for example, 3-pyrroline). Examples of unsaturated heterocyclyl radicals include heteroaromatic rings selected from pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indolyl, benzofuranyl, benzthiophenyl, benzimidazolyl, benzisoxazolyl, benzoxazolyl, benzthiazolyl or benzisothiazolyl.

Said saturated and partially saturated heterocyclyl radicals may be optionally substituted by one, two or three groups independently selected from halogen, $C_{1-6}$alkyl, $C_{1-6}$alkoxy, fluoro$C_{1-6}$alkyl, fluoro$C_{1-6}$alkoxy, $NO_2$, cyano, oxo (=O), $NR^aR^b$, $SR^a$, $SOR^a$, $SO_2R^a$, $COR^a$, $CO_2R^a$, $CONR^aR^b$, $C_{2-6}$alkenyl, $C_{2-6}$alkynyl, $C_{1-4}$alkoxy$C_{1-4}$alkyl, —$O(CH_2)_mO$—, —$OCH_2CH_2CH_2$—, —$CH_2OCH_2CH_2$— or —$CH_2OCH_2C(O)$—. Preferably said saturated or partially saturated heterocyclyl radical is optionally substituted by one or two substituents, especially none or one. Particularly preferred substituents include fluorine, chlorine, bromine, $C_{1-4}$alkyl (especially methyl), $C_{1-4}$alkoxy (especially methoxy), trifluoromethyl, trifluoromethoxy, oxo, vinyl, $C_{1-4}$alkylamino (especially methylamino) or di($C_{1-4}$alkyl)amino (especially dimethylamino).

Said unsaturated heterocyclyl radicals may be optionally substituted by one, two or three groups independently selected from halogen, $C_{1-6}$alkyl, $C_{1-6}$alkoxy, fluoro$C_{1-6}$alkyl, fluoro$C_{1-6}$alkoxy, $NO_2$, cyano, $NR^aR^b$, $SR^a$, $SOR^a$, $SO_2R^a$, $COR^a$, $CO_2R^a$, $CONR^aR^b$, $C_{2-6}$alkenyl, $C_{2-6}$alkynyl, $C_{1-4}$alkoxy$C_{1-4}$alkyl or —$O(CH_2)_mO$—. Preferably said unsaturated heterocyclyl is optionally substituted by one or two substituents, especially none or one. Particularly preferred substituents include fluorine, chlorine, bromine, $C_{1-4}$alkyl (especially methyl), $C_{1-4}$alkoxy (especially methoxy), trifluoromethyl, trifluoromethoxy or vinyl.

As used herein, the term "carbocyclyl" as a group or part of a group means a 3 to 7-membered cycloalkyl radical such as cyclopropyl, cyclobutyl, cyclopentyl or cyclohexyl, wherein said cycloalkyl radical may be optionally substituted by one, two or three groups independently selected from halogen, $C_{1-6}$alkyl, $C_{1-6}$alkoxy, hydroxy$C_{1-6}$alkyl, fluoro$C_{1-6}$alkyl, fluoro$C_{1-6}$alkoxy, $NO_2$, cyano, $SR^a$, $SOR^a$, $SO_2R^a$, $COR^a$, $CO_2R^a$, $CONR^aR^b$, $C_{2-6}$alkenyl, $C_{2-6}$alkynyl, $C_{1-4}$alkoxy$C_{1-4}$alkyl or —$O(CH_2)_mO$—. Preferably said cycloalkyl radical is substituted by one or two substituents, especially one. Particularly preferred substituents include fluorine, chlorine, bromine, $C_{1-4}$alkyl (especially methyl), methoxy, hydroxy$C_{1-4}$alkyl (especially $C(CH_3)_2OH$), trifluoromethyl, trifluoromethoxy or vinyl.

Specific compounds within the scope of this invention include:

cis-(RS)-4-methanesulfonyloxy-N-{1-[3,5-bis(trifluoromethyl)phenyl]ethyl}-1-phenylcyclohexanecarboxamide;

(RS)-1-{1-[(1,4-dioxa-8-phenylspiro[4.5]decan-8-yl)methoxy]ethyl}-3,5-bis(trifluoromethyl)benzene;

(RS)-1-{1-[(4-oxo-1-phenylcyclohexyl)methoxy]ethyl}-3,5-bis(trifluoromethyl)benzene;

(RS)-β-[(1,4-dioxa-8-phenylspiro[4.5]decan-8-yl)methoxy]-3,5-bis(trifluoromethyl)benzeneethanol;

(RS)-β-[(4oxo-1-phenylcyclohexyl)methoxy]-3,5-bis(trifluoromethyl)benzeneethanol;

(RS)-4-oxo-1-phenyl-N-{1-[3,5-bis(trifluoromethyl)phenyl]ethyl}cyclohexanecarboxamide;

(RS)-1-(8-phenyl-1,4-dioxaspiro[4.5]decan-8-yl)-3-[3,5-bis(trifluoromethyl)phenyl]propan-2-yl ethanoate;

(RS)-1-(8-phenyl-1,4-dioxaspiro[4.5]decan-8-yl)-3-[3,5-bis(trifluoromethyl)phenyl]propan-1-yl ethanoate;

(RS)-1-(8-phenyl-1,4-dioxaspiro[4.5]decan-8-yl)-3-[3,5-bis(trifluoromethyl)phenyl]propan-2-ol;

RS)-4-{2-hydroxy-3-[3,5-bis(trifluoromethyl)phenyl]propyl}-4-phenylcyclohexanone;

trans-(RS)-1-({4-[4-(4-fluorophenyl)piperidin-1-yl]-α-methyl-1-phenylcyclohexanemethoxy}methyl)-3,5-bis(trifluoromethyl)benzene;

cis-(RS)-1-({α-ethenyl-4-[4(4-fluorophenyl)piperid-1-yl-]-1-phenylcyclohexanemethoxy}methyl)-3,5-bis(trifluoromethyl)benzene;

trans-(RS)-1-({α-ethenyl-4-[4-(4-fluorophenyl)piperidin-1-yl]-1-phenylcyclohexanemethoxy}methyl)-3,5-bis(trifluoromethyl)benzene;

trans-(RS)-4-[4-(4fluorophenyl)piperidin-1-yl]-1-phenyl-α-[3,5-bis(trifluoromethyl)phenylmethoxy]cyclohexaneethanol;

trans-(RS)-1-({α-ethyl-4-[4-(4-fluorophenyl)piperidin-1-yl]-1-phenylcyclohexanemethoxy}methyl)-3,5-bis(trifluoromethyl)benzene;

trans-1-[({4-[4-(4-fluorophenyl)piperidin-1-yl]-1-phenylcyclohexyl}methoxy)methyl]-2-methoxybenzene;

trans-1-[({4-[4-(4-fluorophenyl)piperidin-1-yl]-1-phenylcyclohexyl}methoxy)methyl]-2-(cyclopropoxy)-5-(trifluoromethoxy)benzene;

cis-(RS)-1-[1-({4-[4-(4-fluorophenyl)piperidin-1-yl]-1-phenylcyclohexyl}methoxy)ethyl]-3,5-bis(trifluoromethyl)benzene;
trans-(RS)-1-[1-({4-[4-(4-fluorophenyl)piperidin-1-yl]-1-phenylcyclohexyl}methoxy)ethyl]-3,5-bis(trifluoromethyl)benzene;
trans-(RS)-β-[(4-hydroxy-1-phenylcyclohexyl)methoxy]-3,5-bis(trifluoromethyl)benzeneethanol;
cis-(RS)-β-[(4-hydroxy-1-phenylcyclohexyl)methoxy]-3,5-bis(trifluoromethyl)benzeneethanol;
cis-(RS)-β-({4-[4-(4-fluorophenyl)piperidin-1-yl]-1-phenylcyclohexyl}methoxy)-3,5-bis(trifluoromethyl)benzeneethanol;
trans-(RS)-β-({4-[4-(4-fluorophenyl)piperidin-1-yl]-1-phenylcyclohexyl}methoxy)-3,5-bis(trifluoromethyl)benzeneethanol;
cis- and trans-(RS)-β-{[1-phenyl-4-(phenylmethylamino)cyclohexyl]methoxy}-3,5-bis(trifluoromethyl)benzeneethanol;
cis- and trans-(RS)-β-[(1-phenyl-4-(piperidin-1-yl)cyclohexyl)methoxy]-3,5-bis(trifluoromethyl)benzeneethanol;
trans-(RS)-β-{[1-phenyl-4-(phenylmethylamino)cyclohexyl]methoxy}-3,5-bis(trifluoromethyl)benzeneethanol;
cis-(RS)-β-{[1-phenyl-4-(phenylmethylamino)cyclohexyl]methoxy}-3,5-bis(trifluoromethyl)benzeneethanol;
trans-(RS)-β-[(4-amino-1-phenylcyclohexyl)methoxy]-3,5-bis(trifluoromethyl)benzeneethanol;
cis-(RS)-β-[(4-amino-1-phenylcyclohexyl)methoxy]-3,5-bis(trifluoromethyl)benzeneethanol;
trans-(RS)-β-({4-[N-methyl(phenylmethyl)amino]-1-phenylcyclohexyl}methoxy)-3,5-bis(trifluoromethyl)benzeneethanol;
trans-(RS)-β-[(4-methylamino-1-phenylcyclohexyl)methoxy]-3,5-bis(trifluoromethyl)benzeneethanol;
trans-(RS)-β-[(4-{N-[2-(dimethylamino)acetyl]amino}-1-phenylcyclohexyl)methoxyl]-3,5-bis(trifluoromethyl)benzeneethanol;
trans-(RS,S)-N-(1-{[α-hydroxymethyl-3,5-bis(trifluoromethyl)phenylmethoxy]methyl}-1-phenylcyclohexyl)-2-pyrrolidinecarboxamide;
cis- and trans-(RS)-β-[(1-phenyl-4-dimethylaminocyclohexyl)methoxy]-3,5-bis(trifluoromethyl)benzeneethanol;
trans-(RS)-β-[(4-cyclopropylmethylamino-1-phenylcyclohexyl)methoxy]-3,5-bis(trifluoromethyl)benzeneethanol;
1,2-dihydro-5-{[N-(1-{[α-hydroxymethyl-3,5-bis(trifluoromethyl)phenylmethoxy]methyl}-1-phenylcyclohex-4-yl)methylamino]methyl}-3H-1,2,4-triazol-3-one;
cis-(RS)-methyl 1-(1-{[α-hydroxymethyl-3,5-bis(trifluoromethyl)phenylmethoxy]methyl}-1-phenylcyclohex-4-yl)piperidine-4-carboxylate;
trans-(RS)-methyl 1-(1-{[α-hydroxymethyl-3,5-bis(trifluoromethyl)phenylmethoxy]methyl}-1-phenylcyclohex-4yl)piperidine-4-carboxylate;
trans-(RS)-1-(1-{[α-hydroxymethyl-3,5-bis(trifluoromethyl)phenylmethoxy]methyl}-1-phenylcyclohex-4-yl)piperidine-4-methanol;
trans-(RS)-1-(1-{[α-hydroxymethyl-3,5-bis(trifluoromethyl)phenylmethoxy]methyl}-1-phenylcyclohex-4-yl)piperidine-4-carboxylic acid;
trans-(RS)-1-(1-{[α-hydroxymethyl-3,5-bis(trifluoromethyl)phenylmethoxy]methyl}-1-phenylcyclohex-4yl)-α,α-dimethylpiperidine-4-methanol;
trans-(RS)-1-(1-{[α-hydroxymethyl-3,5-bis(trifluoromethyl)phenylmethoxy]methyl}-1-phenylcyclohex-4-yl)-N,N-dimethylpiperidine-4-carboxamide;
RS)-methyl (1-(1-{[α-hydroxymethyl-3,5-bis(trifluoromethyl)phenylmethoxy]methyl}-1-phenylcyclohex-4-ylidene)acetate;
cis- and trans-(RS)-methyl(1-(1-{[α-hydroxmethyl-3,5-bis(trifluoromethyl)phenylmethoxy]methyl}-1-phenylcyclohex-4-yl)acetate;
cis-(RS)-1-[2-(1-(1-{[α-hydroxymethyl-3,5-bis(trifluoromethyl)phenylmethoxy]methyl}-1-phenylcyclohex-4yl)ethyl]pyrrolidine;
trans-(RS)-1-[2-(1-(1-{[α-hydroxymethyl-3,5-bis(trifluoromethyl)phenylmethoxy]methyl}-1-phenylcyclohex-4-yl)ethyl]pyrrolidine;
trans-(RS)-methyl α-({4-[4-(4-fluorophenyl)piperidin-1-yl]-1-phenylcyclohexyl}methoxy)-3,5-bis(trifluoromethyl)benzeneacetate;
trans-3,5-bis(trifluoromethyl)phenylmethyl 4-[4-(4-fluorophenyl)piperidin-1-yl]-1-phenylcyclohexanecarboxylate;
trans-(RS)-1-[3,5-bis(trifluoromethyl)phenyl]ethyl 4-[4-(4-fluorophenyl)piperidin-1-yl]-1-phenylcyclohexanecarboxylate;
trans-(RS)-2-hydroxy-2-[3,5-bis(trifluoromethyl)phenyl]ethyl 4-[4-(4-fluorophenyl)piperidin-1-yl]-1-phenylcyclohexanecarboxylate;
trans-(RS)-α-(hydroxymethyl)-[3,5-bis(trifluoromethyl)phenyl]methyl 4-[4-(4-fluorophenyl)piperidin-1-yl]-1-(phenyl)cyclohexanecarboxylate;
trans-(RS)-methyl α-({4-[4-(4-fluorophenyl)piperidin-1-yl]-1-phenylcyclohexyl}carbonyloxy)-3,5-bis(trifluoromethyl)benzeneacetate;
cis-{4-[4-(4fluorophenyl)piperidin-1-yl]-1-phenylcyclohexyl}methyl 3,5-bis(trifluoromethyl)benzoate;
trans-{4-[4-(4-fluorophenyl)piperidin-1-yl]-1-phenylcyclohexyl}methyl 3,5-bis(trifluoromethyl)benzoate;
cis-1-phenyl-4-(4-phenylpiperidin-1-yl)-N-{[3,5-bis(trifuoromethyl)phenyl]methyl}cyclohexanecarboxamide;
trans-1-phenyl-4-(4-phenylpiperidin-1-yl)-N-{[3,5-bis(trifiuoromethyl)phenyl]methyl}cyclohexanecarboxamide;
trans-4-[4-(4-fluorophenyl)piperidin-1-yl]-N-{[3-(methoxy)phenyl]methyl}-1-phenylcyclohexanecarboxamide;
trans-(RS)-4-[4-(4-fluorophenyl)piperidin-1-yl]-N-{1-[3,5-bis(trifluoromethyl)phenyl]ethyl}-1-phenylcyclohexanecarbomide;
trans-(R)-4-[4-(4-fluorophenyl)piperidin-1-yl]-N-{1-[3,5-bis(trifluoromethyl)phenyl]ethyl}-1-phenylcyclohexanecarboxamide;
trans-(S)-4-[4-(4-fluorophenyl)piperidin-1-yl]-N-{1-[3,5-bis(trifluoromethyl)phenyl]ethyl}-1-phenylcyclohexanecarboxamide;
cis-(RS)-4-[4-(4-fluorophenyl)piperidin-1-yl]-N-{1-[3,5-bis(trifluoromethyl)phenyl]ethyl}-1-phenylcyclohexanecarboxamide;
trans-N-methyl-1-phenyl-4-(4-phenylpiperidin-1-yl)-N-{[3,5-bis(trifluoromethyl)phenyl]methyl}cyclohexanecarboxamide;
trans-(RS)-4-[4-(4-fluorophenyl)piperidin-1-yl]-N-methyl-{1-[3,5-bis(trifluoromethyl)phenyl]ethyl}-1-phenylcyclohexanecarboxamide;

trans-(RS)-4-[4-(4-fluorophenyl)piperidin-1-yl]-1-phenyl-N-{2-hydroxy-1-[3,5-bis(trifluoromethyl)phenyl]}ethyl}cyclohexanecarboxamide;

trans-(RS)-4-(1,4-dioxa-8-azaspiro[4.5]decane-8-yl)-1-phenyl-N-{1-[3,5-bis(trifluoromethyl)phenyl] ethyl}cyclohexanecarboxamide;

trans-(RS)-4-(4oxopiperidin-1-yl)-1-phenyl-N-{4-[3,5-bis(trifluoromethyl)phenyl]ethyl}cyclohexanecarboxamide;

trans-(RS)-4-(4hydroxypiperidin-1-yl)-1-phenyl-N-{1-[3,5-bis(trifluoromethyl)phenyl] ethyl}cyclohexanecarboxamide;

trans-(RS)-4-(but-3-enylamino)-1-phenyl-N-{1-[3,5-bis(trifluoromethyl)phenyl]ethyl}cyclohexanecarboxamide;

trans-(RS)-4-(4-hydroxy-4-phenylpiperidin-1-yl)-1-phenyl-N-{1-[3,5-bis(trifluoromethyl)phenyl] ethyl}cyclohexanecarboxamide;

trans-(RS)-4-(1,2,3,6-tetrahydro-4-phenylpyridin-1-yl)-1-phenyl-N-{1-[3,5-bis(trifluoromethyl)phenyl] ethyl}cyclohexanecarboxamide;

trans-(RS)-4-(1,2,3,6-tetrahydro-4-methylpyridin-1-yl)-1-phenyl-N-{1-[3,5-bis(trifluoromethyl)phenyl] ethyl}cyclohexanecarboxamide;

trans-(RS)-4-(4-hydroxy-4-(phenylethyl)piperidin-1-yl)-1-phenyl-N-{1-[3,5-bis(trifluoromethyl)phenyl] ethyl}cyclohexanecarboxamide;

trans-(RS)-4-[(phenyhmethyl)amino-N-{1-[3,5-bis(trifluoromethyl)phenyl]ethyl}-1-phenylcyclohexanecarboxamide;

cis-(RS)-4-[(phenylmethyl)amino]-N-{1-[3,5-bis(trifluoromethyl)phenyl]ethyl}-1-phenylcyclohexanecarboxamide;

trans-(RS)-4-[N-methyl(phenylmethyl)amino]-N-{1-[3,5-bis(trifluoromethyl)phenyl]ethyl}-1-phenylcyclohexanecarboxamide;

trans-(RS)-4-methylamino-N-{1-[3,5-bis(trifluoromethyl)phenyl]ethyl}-1-phenylcyclohexanecarboxamide;

trans-(RS)-4-amino-N-{1-[3,5-bis(trifluoromethyl)phenyl] ethyl}-1-phenylcyclohexanecarboxamide;

trans-(RS)-4-(dimethylamino)-N-{1-[3,5-bis(trifluoromethyl)phenyl]ethyl}-1-phenylcyclohexanecarboxamide;

trans-(RS)-4-[4-(phenylbutyl)amino]-N-{1-[3,5-bis(trifluoromethyl)phenyl]ethyl}-1-phenylcyclohexanecarboxamide;

trans-(RS)-4-[N-methyl-4-(phenylbutyl)amino]-N-{1-[3,5-bis(trifluoromethyl)phenyl]ethyl}-1-phenylcyclohexanecarboxamide;

trans-(RS)-4-acetylamino-N-{1-[3,5-bis(trifluoromethyl)phenyl]ethyl}-1-phenylcyclohexanecarboxamide;

trans-(RS)-4-[(1-oxo-4-phenylbutyl)amino]-N-{1-[3,5-bis(trifluoromethyl)phenyl]ethyl}-1-phenylcyclohexanecarboxamide;

cis- and trans-(RS)-1,1-dimethylethyl 4-[1-({1-[3,5-bis(trifluoromethyl)phenyl]ethylamino}carbonyl)-1-phenylcyclohex-4-yl]-1-piperazinecarboxylate;

trans-(RS)-4-[4-(phenylmethyl)piperazin-1-yl]-N-{1-[3,5-bis(trifluoromethyl)phenyl]ethyl}-1-phenylcyclohexanecarboxamide;

trans-(RS)-4-(piperazin-1-yl)-N-{1-[3,5-bis(trifluoromethyl)phenyl]ethyl}-1-phenylcyclohexanecarbomide;

trans-(RS)-4-(4-methylpiperazin-1-yl)-N-{1-[3,5-bis(trifluoromethyl)phenyl]ethyl}-1-phenylcyclohexanecarboxamide;

trans-(RS)-4-(4-acetylpiperazin-1-yl)-N-{1-[3,5-bis(trifluoromethyl)phenyl]ethyl}-1-phenylcyclohexanecarboxamide;

trans-(RS)-4-(aminomethyl)-N-{1-[3,5-bis(trifluoromethyl)phenyl]ethyl}-1-phenylcyclohexanecarboxamide;

trans-(RS)-4-(N,N-dimethylaminomethyl)-N-{1-[3,5-bis(trifluoromethyl)phenyl]ethyl}-1-phenylcyclohexanecarboxamide;

trans-(RS)-4-[(piperidin-1-yl)methyl]-N-{1-[3,5-bis(trifluoromethyl)phenyl]ethyl}-1-phenylcyclohexanecarboxamide;

trans-(RS)-4-[(morpholin-4-yl)methyl]-N-(1-[3,5-bis(trifluoromethyl)phenyl]ethyl{-1-phenylcyclohexanecarboxamide;

trans-(RS)-4-({N-[2-(dimethylamino)acetyl]}aminomethyl)-N-{1-[3,5-bis(trifluoromethyl)phenyl] ethyl}-1-phenylcyclohexanecarboxamide;

trans-(RS)-4-(1H-1,2,3-triazol-1-yl)-N-{1-[3,5-bis(trifluoromethyl)phenyl]ethyl}-1-phenylcyclohexanecarboxamide;

trans-N-({4-[4-(4-fluorophenyl)piperidin-1-yl]-1-phenylcyclohexylmethyl}-3,5-bis(trifluoromethyl) benzenecarboxamide;

trans-N-({4-[4-(4-fluorophenyl)piperidin-1-yl]-1-phenylcyclohexyl}methyl)-2-(methoxy) benzenemethanamine;

trans-N-({4-[4-(4-fluorophenyl)piperidin-1-yl]-1-phenylcyclohexyl}methyl)-3,5-bis(trifluoromethyl) benzenemethanamine;

cis-N-({4-[4-(4-fluorophenyl)piperidin-1-yl]-1-phenylcyclohexyl}methyl)-3,5-bis(trifluoromethyl) benzenemethanamine;

trans-N-({4-[4-(4-fluorophenyl)piperidin-1-yl]-1-phenylcyclohexyl}methyl)-N-methyl-3,5-bis (trifluoromethyl)benzenemethanamine;

cis- and trans-N-({4-[4-(4-fluorophenyl)piperidin-1-yl]-1-phenylcyclohexyl}methyl)-N-{[3,5-bis(trifluoromethyl)phenyl]methyl}acetamide;

trans-(RS)-N-({4-[4-(4-fluorophenyl)piperidin-1-yl]-1-phenylcyclohexy}methyl)-α-methyl-3,5-bis (trifluoromethyl)benzenemethanamine;

trans-(RS)-α-({4-[4-(4-fluorophenyl)piperidin-1-yl]-1-phenylcyclohexy}methylamino)-3,5-bis(trifluoromethyl) benzeneethanol;

trans-(RS)-α-({4-[4-(4-fluorophenyl)piperidin-1-yl]-1-phenylcyclohexyl}methylamino)-3,5-bis (trifluoromethyl)benzeneethanamine;

cis- and trans-(E)-4-(4-fluorophenyl)-1-(4-phenyl-4-{3-[3,5-bis(trifluoromethyl)phenyl]prop-1-enyl}cyclohexyl) piperidine;

cis- and trans-(E)-4-(4-fluorophenyl)-1-(4-phenyl-4-{3-[3,5-bis(trifuoromethyl)phenyl]propyl}cyclohexyl) piperidine;

cis- and trans-(RS)-4-(4-fluorophenyl)-1-(4-{2-hydroxy-3-[3,5-bis(trifluoromethyl)phenyl]propyl}-4-phenylcyclohexyl)piperidine;

cis- and trans-(RS)-4-(4-fluorophenyl)-1-(4-{2-oxo-3-[3,5-bis(trifluoromethyl)phenyl]propyl}-4-phenylcyclohexyl)piperidine;

1-{[(1,4-dioxa-8-phenylspiro[4.5]decan-8-yl)methoxy]methyl}-3,5-bis(trifluoromethyl)benzene;

1-({[4-oxo-1-phenylcyclohexyl]methoxy}methyl)-3,5-bis(trifluoromethyl)benzene;

cis-1-({4-[4-(4-fluorophenyl)piperidin-1-yl]-1-phenylcyclohexanemethoxy}methyl)-3,5-bis (trifluoromethyl)benzene;

trans-1-({4-[4-(4-fluorophenyl)piperidin-1-yl]-1-phenylcyclohexanemethoxy}methyl)-3,5-bis (trifluoromethyl)benzene;

(RS)-4-methylene-1-phenyl-N-{1-[3,5-bis(trifluoromethyl)phenyl]ethyl}cyclohexanecarboxamide;

cis-(RS)-4-(hydroxymethyl)-N-{1-[3,5-bis(trifluoromethyl)phenyl]ethyl}-1-phenylcyclohexanecarboxamide;
trans-(RS)-4-(hydroxymethyl)-N-{1-[3,5-bis(trifluoromethyl)phenyl]ethyl}-1-phenylcyclohexanecarboxamide;

and pharmaceutically acceptable salts thereof.

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention have one or more asymmetric centres, and may accordingly exist both as enantiomers and as diastereoisomers. It is to be understood that all such isomers and mixtures thereof are encompassed within the scope of the present invention.

The preferred compounds of the formula (I) and (Ia) will have the stereochemistry of the 1- and 4-positions as shown in formula (Ib)

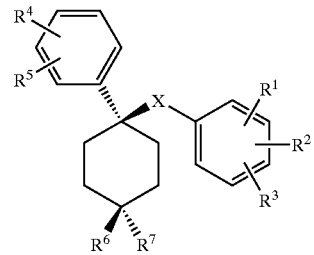

(Ib)

It will be appreciated that the preferred definitions of the various substituents recited herein may be taken alone or in combination and, unless otherwise stated, apply to the generic formula for compounds of the present invention as well as to the preferred classes of compound represented by formula (Ia) and formula (Ib).

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, solutions or suspensions, or suppositories, for oral, parenteral or rectal administration, or administration by inhalation or insufflation. Oral compositions such as tablets, pills, capsules or wafers are particularly preferred.

A more detailed description of pharmaceutical compositions that are suitable for the formulation of compounds of the present invention is disclosed in U.S. Pat. No. 6,071,927, the content of which is incorporated herein by reference (see in particular, column 8, line 50 to column 10, line 4).

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. A comprehensive listing of clinical conditions, uses and methods of treatment for which the compounds of the present invention will be useful is disclosed in U.S. Pat. No. 6,071,927, the content of which is incorporated herein by reference (see, in particular, column 10, line 14 to column 22, line 18).

In particular, the compounds of the present invention are useful in the treatment of a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; and anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders.

The compounds of the present invention are also particularly useful in the treatment of nociception and pain. Diseases and conditions in which pain predominates, include soft tissue and peripheral damage, such as acute trauma, osteoarthritis, rheumatoid arthritis, musculo-skeletal pain, particularly after trauma, spinal pain, myofascial pain syndromes, headache, migraine, episiotomy pain, and burns.

The compounds of the present invention are also particularly useful in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; in the treatment of inflammatory diseases such as inflammatory bowel disease, psoriasis, fibrositis, osteoarthritis, rheumatoid arthritis, pruritis and sunburn; and in the treatment of allergic disorders such as eczema and rhinitis.

The compounds of the present invention are also particularly useful in the treatment of gastrointestinal (GI) disorders, including inflammatory disorders and diseases of the GI tract such as ulcerative colitis, Crohn's disease and irritable bowel syndrome.

The compounds of the present invention are also particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents, including those routinely used in cancer chemotherapy; by radiation including radiation therapy such as in the treatment of cancer; and in the treatment of post-operative nausea and vomiting.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

In the treatment of psychiatric disorders, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

According to a general process (A), compounds of formula (I), in which X is —C(O)N($R^{13}$)C$R^{14}R^{15}$—, may be prepared by the reaction of a compound of formula (II) with a compound of formula (III)

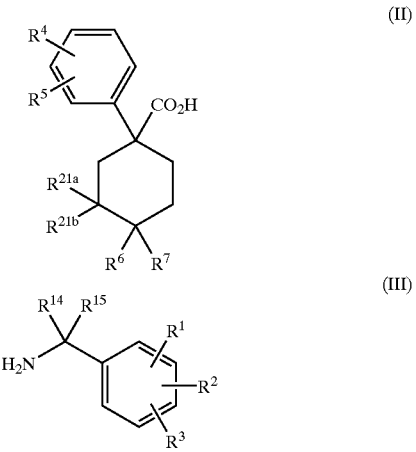

in the presence of a base and a coupling reagent.

Suitable bases of use in the reaction include tertiary amines, for example, triethylamine.

Suitable coupling reagents include any of the coupling reagents commonly used in peptide synthesis. A preferred coupling reagent is 1-(3-dimethylaminopropyl)-3-ethylcarbodiimide hydrochloride (EDC). Preferably the coupling reaction is effected in the presence of 1-hydroxybenzotriazole hydrate (HOBT).

The reaction is conveniently effected in a suitable organic solvent such as, for example, dimethylformamide.

According to an alternative general process (B), compounds of formula (I), in which X is —C(O)N($R^{13}$)C$R^{14}R^{15}$—, may be prepared by the reaction of an amine of formula (III) with an activated carboxylic acid derivative of formula (IV)

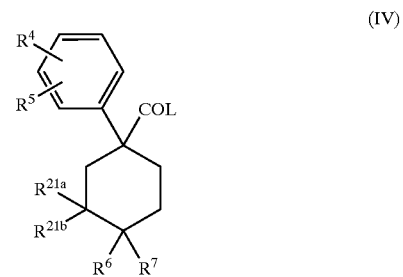

where L is a leaving group.

Suitable activated carboxylic acid derivatives represented in formula (IV) include acyl halides (e.g. acid chlorides) and acid anhydrides including mixed anhydrides (e.g. acid formic anhydride). These activated derivatives may be formed from the corresponding acid of formula (II) by well known procedures. For example, acid chlorides may be prepared by reaction with phosphorus pentachloride, thionyl chloride or oxalyl chloride and acid anhydrides may be prepared by reaction with an appropriate acid anhydride (e.g. trifluoroacetic anhydride), an acid chloride (e.g. acetyl chloride), an alkyl or aralkyl haloformate (e.g. ethyl or benzyl chloroformate) or methanesulphonyl chloride.

A particularly preferred reagent for activating the carboxylic acid group is bis(2-oxo-3-oxazolidinyl)phosphinic chloride (BOP-Cl).

Activated carboxylic acid derivatives of formula (IV) may also be prepared in situ by reaction of the corresponding acids of formula (II), with a coupling reagent such as carbonyldiimidazole, dicyclohexylcarbodiimide or diphenylphosphorylazide.

The conditions under which the activated carboxylic acid derivatives of formula (IV) are formed and subsequently reacted with the amines of formula (III) will depend upon the nature of the activated derivative. However, in general the reaction between the compounds (III) and (IV) may be carried out in a non-aqueous medium such as, for example, dimethylformamide, tetrahydrofuran, acetonitrile or a halogenated hydrocarbon such as dichloromethane at a temperature within the range −25° C. to +150° C. The reaction may optionally be carried out in the presence of a base such as triethylamine or pyridine and the base may also be used as the solvent for reaction.

Where acid chlorides are used, the reaction may be carried out using the Schotten-Baumann technique in the presence of a suitable base, for example, aqueous sodium hydroxide, conveniently at a temperature between 0° C. and 100° C., for example, room temperature.

According to another general process (C), compounds of formula (I), in which X is —$CR^{14}R^{15}N(R^{13})C(O)$—, may be prepared by the reaction of a compound of formula (V) with a compound of formula (VI) or an activated derivative thereof

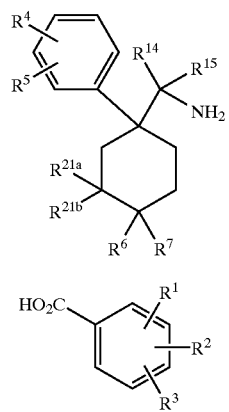

(V)

(VI)

using the methods described in processes (A) and (B), above.

According to another general process (D), compounds of formula (I), in which X is —$CR^{14}R^{15}N(R^{13})CR^{16}R^{17}$—, may be prepared by the reaction of a compound of formula (VII) with a compound of formula (VIII)

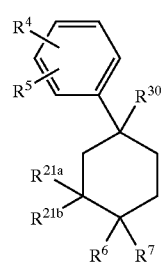

(VII)

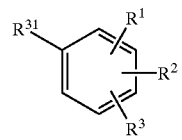

(VIII)

(wherein $R^{30}$ is —$CR^{14}R^{15}NH_2$ and $R^{31}$ is CHO, or $R^{30}$ is CHO and $R^{31}$ is —$CR^{16}R^{17}NH_2$) in the presence of a reducing agent.

Suitable reducing agents for use in this reaction include, for example, sodium cyanoborohydride or sodium triacetoxyborohydride.

The reaction is conveniently effected in a suitable solvent such as a halogenated hydrocarbon, for example, 1,2-dichloroethane, an alcohol, for example, methanol, acetic acid or a mixture thereof.

According to another general process (E), compounds of formula (I), in which X is —$C(O)OCR^{14}R^{15}$—, may be prepared by the reaction of an activated carboxylic acid derivative (IV) with a compound of formula (IX)

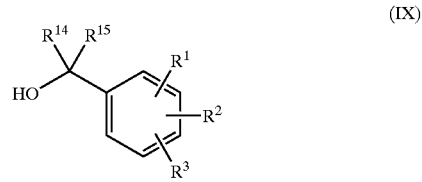

(IX)

in the presence of a base.

Suitable bases of use in the reaction include aromatic amines such as pyridine or 4-(dimethylamino)pyridine (DMAP).

The reaction is conveniently effected in a suitable aprotic solvent such as, for example, dimethylformamide, or a halogenated hydrocarbon, for example, dichloromethane, or a mixture thereof.

According to another general process (F), compounds of formula (I), in which X is —$CR^{14}R^{15}OC(O)$—, may be prepared by the reaction of a compound of formula (X) with a compound of formula (XI)

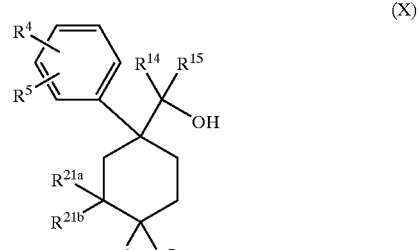

(X)

(XI)

(provided that $R^{21a}$ is not hydroxy) using a method described in process (E) above.

According to another general process (G), compounds of formula (I), in which X is —CR$^{14}$R$^{15}$OCR$^{16}$R$^{17}$—, may be prepared by reacting a compound of formula (X) with a compound of formula (XII)

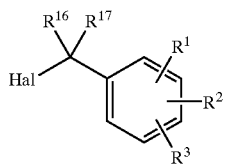

(XII)

(wherein Hal is a halogen atom such as chlorine, iodine or, preferably, bromine), in the presence of a base such as sodium hydride.

The reaction is conveniently effected in a suitable aprotic solvent such as, for example, dimethylformamide.

According to another general process (H), compounds of formula (I), in which X is —CH=CHCR$^{18}$R$^{19}$—, may be prepared by the reaction of a compound of formula (VII) where R$^{30}$ is CHO with a compound of formula (XIII)

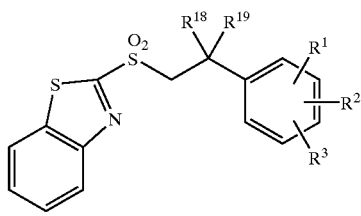

(XIII)

in the presence of lithium hexamethyldisilazide.

The reaction is conveniently effected in a suitable aprotic solvent such as an ether, for example, tetrahydrofuran, at a reduced temperature, for example, at about −78° C.

According to another general process (J), compounds of formula (I), in which X is —CR$^{14}$R$^{15}$CH=CH—, may be prepared by the reaction of a compound of formula (VIII) wherein R$^{31}$ is CHO with a compound of formula (XIV)

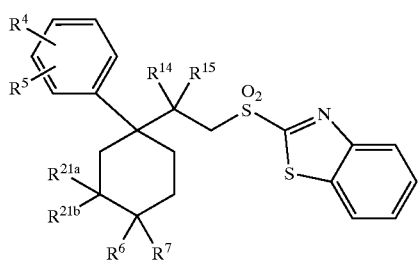

(XIV)

using the method described in process (H), above.

It will be appreciated that compounds of formula (I) may also be prepared from other compounds of formula (I) by a variety of interconversion processes.

Thus, according to general process (K.1), compounds of formula (I) in which X is —CR$^{14}$R$^{15}$N(R$^{13}$)CR$^{16}$R$^{17}$—, may be prepared by the interconversion of a compound of formula (I) in which X is either —C(O)N(R$^{13}$)CR$^{14}$R$^{15}$— or —CR$^{14}$R$^{15}$N(R$^{13}$)C(O)—, by reaction with a reducing agent.

Suitable reducing agents for use in this reaction include sodium borohydride or borane.tetrahydrofuran complex.

The reaction is conveniently effected in a solvent such as an ether, for example, tetrahydrofuran.

According to another general process (K.2), compounds of formula (I) in which X is —CR$^{14}$R$^{15}$OCH(CH$_3$)— or —CH(CH$_3$)OCR$^{14}$R$^{15}$—, may be prepared by interconversion of a compound of formula (I) in which X is —CR$^{14}$R$^{15}$OC(O)— or —C(O)OCR$^{14}$R$^{15}$—, respectively, by reaction with dimethyltitanocene in toluene followed by reduction using, for instance, catalytic hydrogenation conditions, for example, hydrogenation in the presence of palladium hydroxide on carbon, in a suitable solvent such as an ester, for example, ethyl acetate.

According to another general process (K.3), compounds of formula (I) in which X is —CR$^{14}$R$^{15}$OCH(CH$_2$OH)— or —CH(CH$_2$OH)OCR$^{14}$R$^{15}$—, may be prepared by interconversion of a compound of formula (I) in which X is —CR$^{14}$R$^{15}$OC(O)— or —C(O)OCR$^{14}$R$^{15}$—, respectively, by reaction with dimethyltitanocene in toluene followed by reduction using, for instance, a reducing agent such as borane.tetrahydrofuran complex, followed by treatment with hydrogen peroxide in the presence of a base such as sodium hydroxide.

According to another general process (K.4), compounds of formula (I) in which X is —CR$^{14}$R$^{15}$CR$^{16}$R$^{17}$CR$^{18}$R$^{19}$—, may be prepared by interconversion of a compound of formula (I) in which X is —CR$^{14}$=CR$^{16}$CR$^{18}$R$^{19}$— or —CR$^{14}$R$^{15}$CR$^{16}$=CR$^{18}$—, by reduction using, for instance, catalytic hydrogenation conditions, for example, hydrogenation in the presence of palladium hydroxide on carbon, in a suitable solvent such as an alcohol, for example, methanol.

According to another general process (K.5), compounds of formula (I) in which R$^7$ is —(CH$_2$)$_n$NR$^8$R$^9$ (where n is zero) may be prepared by interconversion of a compound of formula (I) in which R$^6$ and R$^7$ together represent =O, by reaction with an appropriate amine, R$^8$R$^9$NH, in the presence of sodium cyanoborohydride and a Lewis acid, for example, zinc chloride, in a solvent such as an alcohol, for example, methanol, or in the presence of sodium triacetoxyborohydride in a solvent such as a halogenated hydrocarbon, for example, 1,2-dichloroethane.

Yet further interconversion reactions that may be effected using conventional procedures are shown in the following Scheme 1. The methods depicted in Scheme 1 are not exhaustive and illustrate just some of the possible routes to further compounds of formula (I).

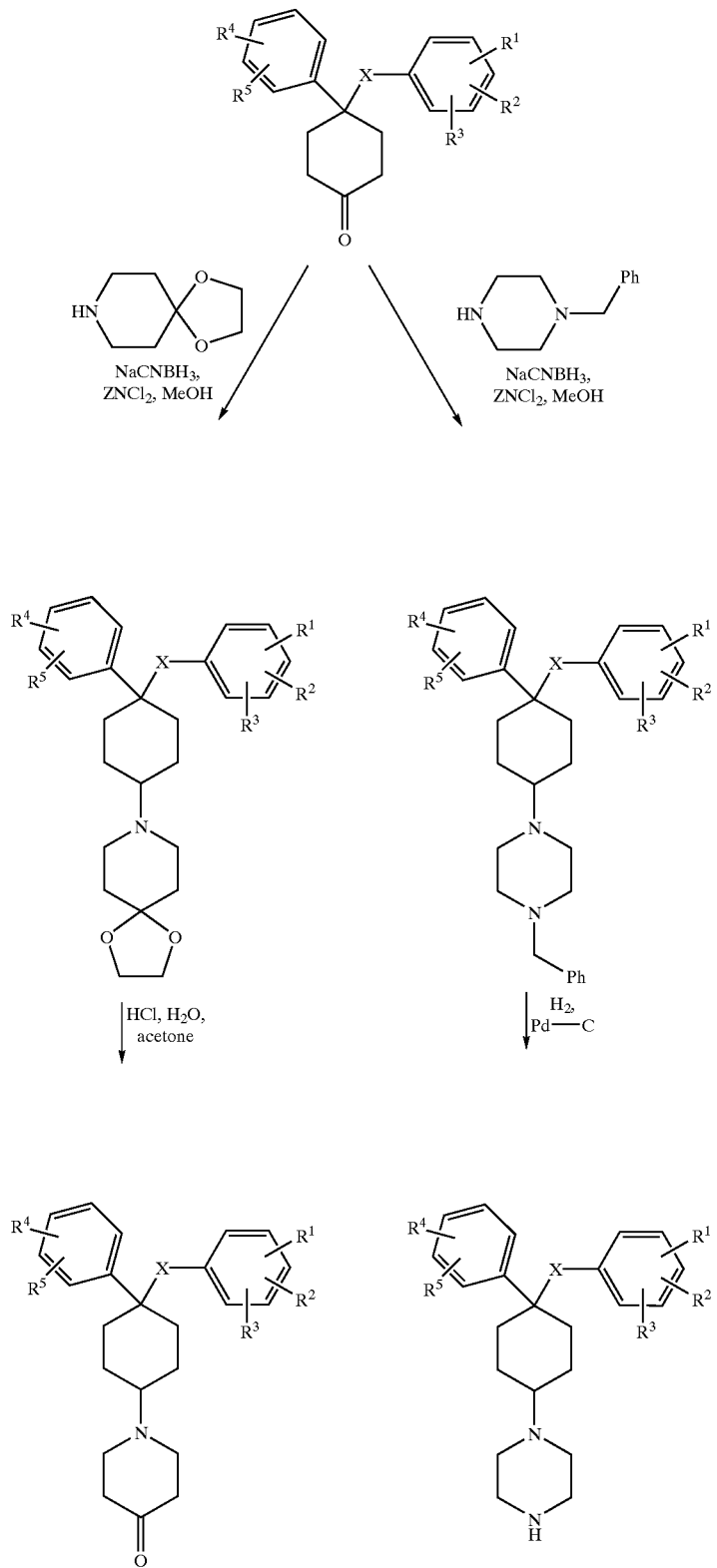
Scheme 1

-continued
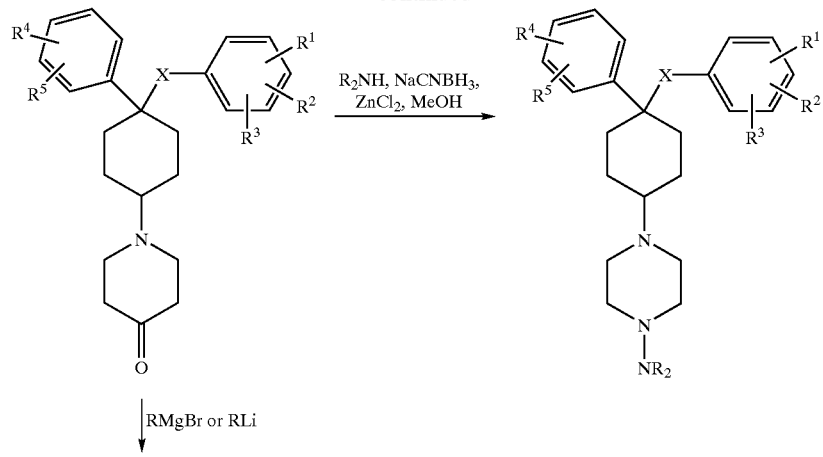
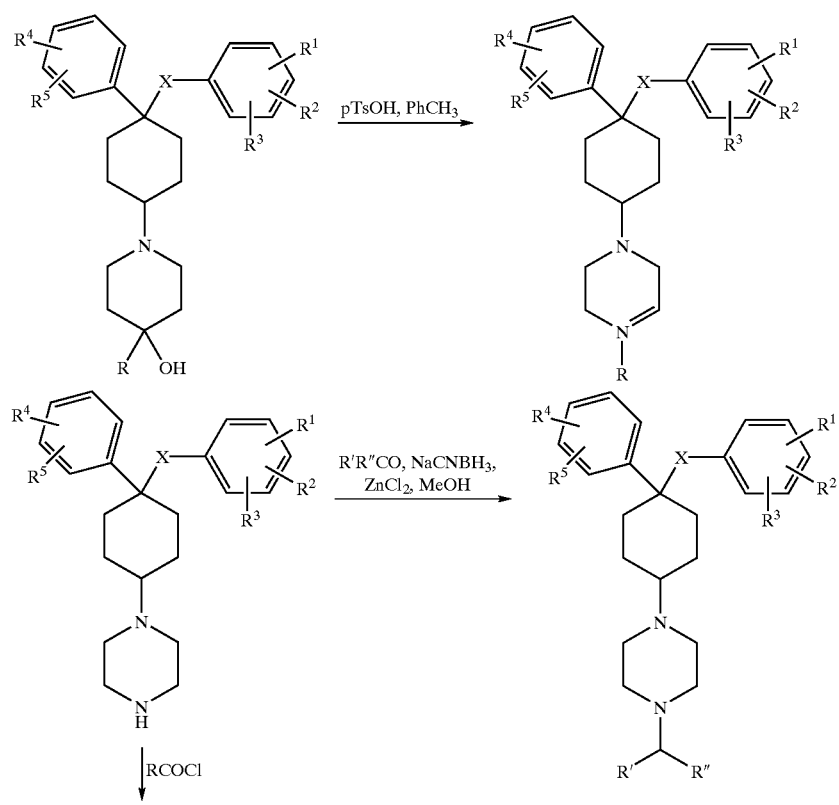
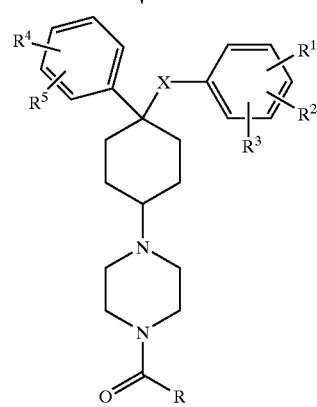

It will be appreciated that reference to R, R' and R" in Scheme 1 refers to suitable substituents within the scope of the definitions of formula (I), insofar as said substituents are compatible with the reaction conditions described in Scheme 1.

Preferably, where $R^{21a}$ is halogen or hydroxy, or $R^{21a}$ and $R^{21b}$ both represent fluorine or together represent oxo (=O), such substituents are introduced at a late stage by conventional methodology. It will be appreciated, however, that where such substituents are compatible with the reactions described above, then such groups may be present, even if not depicted in the above formulae.

Further details of suitable procedures for the preparation of compounds of formula (I) will be found in the accompanying Examples.

Compounds of formula (II) may be prepared by conventional methods. Thus for example, a compound of formula (II) wherein $R^6$ and $R^7$ together represent =O may be prepared according to the following two-step procedure or by methods analogous thereto:

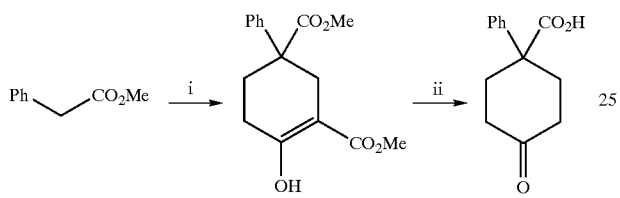

In step (i), methyl phenyl acetate is treated with a base such as sodium hydride and reacted with methyl acrylate. The reaction is conveniently effected in a solvent such as dimethylformamide at a temperature between 0° C. and room temperature. In step (ii), selective decarboxylation is effected using, for example, lithium hydroxide. The reaction is conveniently effected in a solvent or mixture of solvents such as an alcohol, for example, methanol, an ether, for example, tetrahydrofuran, and water. The desired carboxylic acid is obtained by acid hydrolysis of the ester using, for example, a mineral acid such as hydrochloric acid.

Compounds of formula (III) are either known compounds or may be prepared by conventional methods. Examples of suitable methods include, but are not limited to, the methods shown in Scheme 2.

Scheme 2

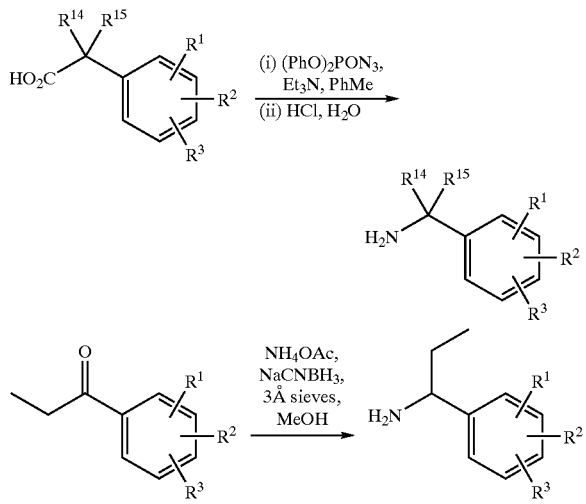

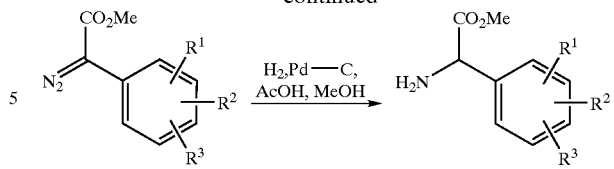

Compounds of formula (V) in which $R^{14}$ and $R^{15}$ are both hydrogen may be prepared from the corresponding carbonitrile compound of formula (XV)

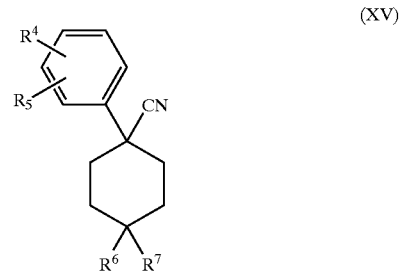

(XV)

by treatment with a reducing agent such as lithium aluminium hydride. The reaction is conveniently effected at room temperature in a solvent such as an ether, for example, diethyl ether.

Similarly, compounds of formula (VII) in which $R^{30}$ is CHO may be prepared, for example, by reduction of the corresponding carbonitrile of formula (XV) using a suitable reducing agent such as diisobutylaluminium hydride (DIBAL-H). The reaction is conveniently effected in a solvent such as a halogenated hydrocarbon, for example, dichloromethane, or a hydrocarbon, for example, hexane, or a mixture thereof.

Compounds of formula (IX) are either known compounds or may be prepared by conventional methods, for instance, reduction of the corresponding carboxylic acid using, for example, lithium aluminium hydride at room temperature in a solvent such as as ether, for example, diethyl ether.

Similarly, compounds of formula (X) may be prepared by reduction of the corresponding carboxylic acid or, more preferably, the corresponding aldehyde of formula (VII) in which $R^{30}$ is CHO. Suitable reducing agents include diisobutylaluminium hydride, lithium aluminium hydride or, more preferably, sodium borohydride. The reaction is conveniently effected in a solvent such as an ether, for example, diethyl ether, a halogenated hydrocarbon, for example dichloromethane, or a hydrocarbon, for example, hexane, or a mixture thereof.

Compounds of formula (XI) may be prepared from the corresponding carboxylic acid of formula (VI) using methods analogous to those described herein for the synthesis of compounds of formula (IV).

Compounds of formulae (XIII) and (XIV) may be prepared by conventional methods, in particular by the reaction of a compound of formula (XVI) or (XVII), respectively

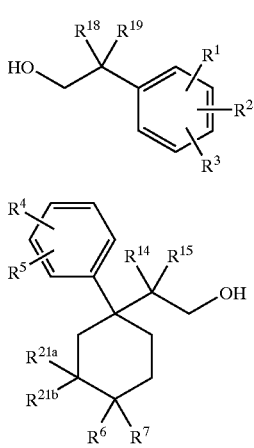

(provided that $R^{21a}$ is not hydroxy) with 2,2'-dithiobis (benzothiazole) in the presence of tributylphosphine to afford the ethylthiobenzothiazole which is subsequently oxidised using, for example, oxone. The benzothiazole step is conveniently effected in an aprotic solvent such as an ether, for example, tetrahydrofuran, whilst the oxidation step is conveniently effected in a solvent such as a halogenated hydrocarbon, for example, chloroform.

Compounds of formulae (VI), (XII), (XV) and (XVI) are either known compounds or may be prepared by conventional methods, for instance, by methods analogous to those described herein.

Compounds of formula (I) in which the ring A is a pyridyl ring may be prepared in an analogous manner to the methods described above, replacing the phenyl ring depicted in the above formulae as appropriate.

It will be appreciated that the general methodology described above may be adapted, using methods that are readily apparent to one of ordinary skill in the art, in order to prepare further compounds of the present invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with $IC_{50}$ at the $NK_1$ receptor of less than 100 nM on said test method.

The following non-limiting Examples serve to illustrate the preparation of compounds of the present invention:

DESCRIPTION 1

Dimethyl 4-Oxo-1-phenyl-1,3-cyclohexanedicarboxylate

Sodium hydride (60% in mineral oil, 35.8 g, 1.49 mol) was washed with hexane to remove the mineral oil, suspended in dimethylformamide (400 mL) and cooled to 0° C. Methyl phenyl acetate (42 mL, 0.3 mol) was added slowly with stirring. Methyl acrylate (59 mL, 0.65 mol) was added dropwise over 2 hours at 0° C. and the mixture was stirred at room temperature overnight. Aqueous ammonium chloride (saturated) was added and the mixture was extracted with dichloromethane (2×700 mL). The combined organic fractions were washed with water (5×500 mL), dried ($MgSO_4$) and the solvent was evaporated under reduced pressure. The residue was purified by flash column chromatography on silica gel, eluting with isohexane/$Et_2O$ (80:20) and the residue was triturated with isohexane/$Et_2O$ (50:50). The solid was collected and dried in vacuo to give the tide compound as colorless crystals (30 g, 35%).

$^1H$ NMR (400 MHz, $CDCl_3$) δ 12.11 (1H, s), 7.36–7.25 (5H, m), 3.81 (3H, s), 3.64 (3H, s), 3.08 (1H, d, J 16.1 Hz), 2.73 (1H, d, J 16.1 Hz), 2.26–2.37 (2H, m), and 2.22–2.17 (2H, m).

DESCRIPTION 2

4-Oxo-1-phenylcyclohexanecarboxylic Acid

Lithium hydroxide monohydrate (11.08 g, 264 mmol) was added to a suspension of dimethyl 4-oxo-1-phenyl-1,3-cyclohexanedicarboxylate (Description 1, 25.5 g, 87.9 mmol) in methanol (250 mL), water (83 mL) and tetrahydrofuran (83 mL) and the mixture was heated under reflux for 3 days. The mixture was cooled and the tetrahydrofuran and methanol were evaporated under reduced pressure. The pH was adjusted to 1 with hydrochloric acid (5M) and the mixture was extracted with dichloromethane. The combined organic fractions were dried ($MgSO_4$) and the solvent was evaporated under reduced pressure to give the title compound as a light yellow solid (19 g, 99%). $^1H$ NMR (400 MHz, $CDCl_3$) δ 7.50–7.29 (5H, m), 2.29–2.73 (2H, m), 2.62–2.55 (2H, m), 2.47–2.41 (2H, m), and 2.35–2.27 (2H, m).

DESCRIPTION 3

(RS)-1-[3,5-Bis(trifluoromethyl)phenyl]-1,2-ethanediol

Osmium tetroxide (2.5 wt % solution in 2-methyl-2-propanol, 1 mL) was added to a mixture of 1-ethenyl-3,5-bis(trifluoromethyl)benzene (1.85 g, 7.74 mmol) and N-methylmorpholine-N-oxide (1.13 g, 9.67 mmol) in tetrahydrofuran (35 mL) and water (15 mL) and the mixture was stirred at room temperature for 18 hours. Aqueous sodium bisulfite (saturated, 30 mL) was added and the tetrahydrofuran was evaporated under reduced pressure. The mixture was extracted with ethyl acetate (2×100 mL) and the combined organic fractions were dried ($Na_2SO_4$) and the solvent was evaporated under reduced pressure to give the title compound (2.09 g, 98%). $^1H$ NMR (400 MHz, $CDCl_3$) δ 7.86 (2H, s), 7.82 (1H, s), 4.97 (1H, dd, J 8.0, 4.0 Hz), 3.87 (1H, dd, J 11.0, 4.0 Hz), and 3.66 (1H, dd, J 8.0, 11.0 Hz).

DESCRIPTION 4

(RS)-1-[3,5-Bis(trifluoromethyl)-α-{[2-(trimethylsilyl)ethoxy]methoxymethyl}benzenemethanol N-Ethyl-N,N-diisopropylamine (465 μl, 2.67 mmol) was added over 2 minutes, to a solution of (RS)-1-[3,5-bis(trifluoromethyl)phenyl]-1,2-ethanediol (Description 3, 488 mg, 1.78 mmol) and [2-(chloromethoxy)ethyl] trimethylsilane (315 μl, 1.78 mmol) in dichloromethane (3 mL) and the mixture was stirred at room temperature for 4 hours, then at 50° C. for 1 hour. The mixture was cooled and dichloromethane (20 mL) and water (20 mL) were added.

The layers were separated and the aqueous layer was extracted with dichloromethane (10 mL). The combined organic fractions were dried ($Na_2SO_4$) and the solvent was evaporated under reduced pressure. The residue was purified by flash column chromatography on silica gel, eluting with isohexane/EtOAc (90:10) to give the title compound (352 mg, 49%). $^1H$ NMR (400 MHz, $CDCl_3$) δ 7.86 (2H, s), 7.79 (1H, s), 4.96 (1H, m), 4.73 (2H, s), 3.87 (1H, dd, J 11.1, 3.0 Hz), 3.73 (1H, br s), 3.61 (3H, m), 0.93 (2H, t, J 8.5 Hz), and 0.02 (9H, s).

DESCRIPTION 5

(RS)-α-Methyl-3,5-bis(trifluoromethyl) benzenemethanamine

O-Methylhydroxylamine hydrochloride (19.57 g, 234 mmol) was added to a solution of 1-[3,5-bis(trifluoromethyl)phenyl]ethanone (50 g, 195 mmol), and sodium acetate (31.9 g, 234 mmol) in ethanol (450 mL) and water (150 mL) and the mixture was heated under reflux for 18 hours. The mixture was cooled, water (1000 mL) was added and the mixture was extracted with diethyl ether. The combined organic fractions were dried ($MgSO_4$) and the solvent was evaporated under reduced pressure. The residue was dissolved in tetrahydrofuran (100 mL), cooled to 0° C. and borane-tetrahydrofuran complex (1M in tetrahydrofuran, 730 mL) was added. The mixture was heated under reflux for 18 hours, cooled and hydrochloric acid (5M, 500 mL) was added slowly. The tetrahydrofuran was evaporated under reduced pressure and the mixture was basified with aqueous sodium hydroxide (4M). The mixture was extracted with ether and the combined organic fractions were washed with aqueous sodium hydroxide (4M) and dried ($MgSO_4$), and ethereal hydrogen chloride (400 mL, 400 mmol) was added. The solid was collected, washing with diethyl ether, and dried in vacuo to give (RS)-α-methyl-3,5-bis (trifluoromethyl)benzenemethanamine hydrochloride as a colorless solid (48.2 g, 100%). $^1H$ NMR (400 MHz, $CD_3OD$) δ 8.13 (2H, s), 8.07 (1H, s), 4.73 (1H, q, J 6.8 Hz), 3.31 (2H, d, J 1.4 Hz), and 1.69 (3H, d, J 6.8 Hz). m/z ($ES^+$) 258 (M+1). A sample was suspended in aqueous sodium hydroxide (4M) and extracted with ether. The combined organic fractions were washed with aqueous sodium hydroxide (4M), dried ($MgSO_4$) and the solvent was evaporated under reduced pressure to give the title compound as a colorless oil. $^1H$ NMR (400 MHz, $CDCl_3$) δ 7.85 (2H, s), 7.76 (1H, s), 4.30 (1H, q, J 6.6 Hz), 1.74 (2H, br s), and 1.42 (3H, d, J 6.6 Hz). m/z ($ES^+$) 258 (M+1).

DESCRIPTION 6

(RS)-2-Methoxy-α-methylbenzenemethanamine Hydrochloride

Sodium cyanoborohydride (2.46 g, 39.1 mmol) was added to a mixture of 1-(2-methoxyphenyl)ethanone (5.87 g, 39.1 mmol), ammonium acetate (30 g, 391 mmol) and 3 Å molecular sieves (20 g) in methanol (200 mL) and the mixture was stirred at room temperature for 3 days. The mixture was filtered and the solvent was evaporated under reduced pressure. The residue was dissolved in aqueous sodium hydroxide (1M) and the mixture was extracted with ethyl acetate. The combined organic fractions were washed with water, dried ($MgSO_4$), and the solvent was evaporated under reduced pressure. The residue was dissolved in diethyl ether and ethereal hydrogen chloride (1M, 50 mL) was added. The solid was collected, washing with diethyl ether, and dried in vacuo to give the title compound as a colorless solid (6.82 g, 93%). m/z ($ES^+$) 135 (M+1-$NH_3$).

DESCRIPTION 7

(RS)-α-Ethyl-3,5-bis(trifluoromethyl) benzenemethanamine Hydrochloride

Prepared from 1-[3,5-bis(trifluoromethyl)phenyl]propanone according to the method of Description 6. m/z ($ES^+$) 272 (M+1), 255 (M+1-$NH_3$).

DESCRIPTION 8

Methyl 3,5-Bis(trifluoromethyl)benzeneacetate

Sulfuric acid (conc., 1 mL) was added to a solution of 3,5-bis(trifluoromethyl) benzeneacetic acid (50.0 g, 0.18 mol) in methanol (400 mL) and the mixture was stirred at room temperature for 1 week. The solvent was evaporated and ethyl acetate (100 mL) and aqueous sodium hydrogen carbonate (saturated, 600 mL) were added. The layers were separated and the aqueous layer was extracted with ethyl acetate (2×300 mL). The combined organic fractions were washed with brine, dried ($MgSO_4$) and the solvent was evaporated under reduced pressure to give the title compound (49.0 g, 93%). $^1H$ NMR (400 MHz, $CDCl_3$) 7.80 (1H, s), 7.75 (2H, s), 3.77 (2H, s), and 3.75 (3H, s).

DESCRIPTION 9

Methyl α,α-Dimethyl-3,5-bis(trifluoromethyl) benzeneacetate

Sodium hydride (60% in mineral oil, 2.1 g, 52.5 mmol) was added in portions to a solution of methyl 3,5-bis (trifluoromethyl)benzeneacetate (Description 8, 5 g, 17.5 mmol) in dimethylformamide (100 mL) and the mixture was stirred for 10 minutes. Iodomethane (5.45 mL, 87.5 mmol) was added and the mixture was stirred at room temperature overnight. Aqueous ammonium chloride (saturated) was added and the mixture was extracted with ethyl acetate. The combined organic fractions were washed with water, dried ($MgSO_4$), and the solvent was evaporated under reduced pressure. The residue was purified by flash column chromatography on silica gel, eluting with isohexane/EtOAc (100:0 increasing to 90:10) to give the title compound as a colorless oil (5.34 g, 97%). $^1H$ NMR (400 MHz, $CDCl_3$) δ 7.78 (3H, s), 3.69 (3H, s), and 1.65 (6H, s).

DESCRIPTION 10

α,α-Dimethyl-3,5-bis(trifluoromethyl)benzeneacetic Acid

Lithium hydroxide monohydrate (2.13 g, 50.6 mmol) was added to a suspension of methyl α,α-dimethyl-3,5-bis (trifluoromethyl)benzeneacetate (Description 9, 5.3 g, 16.88 mmol) in methanol (60 mL), water (20 mL) and tetrahydrofuran (20 mL) and the mixture was degassed and stirred at room temperature for 3 days. The solvent was evaporated under reduced pressure and the residue was suspended in hydrochloric acid (1M). The mixture was extracted with ethyl acetate and the combined organic fractions were dried ($MgSO_4$) and the solvent was evaporated under reduced pressure to give the title compound as a colorless solid (5.05 g, 100%). $^1H$ NMR (400 MHz, $CDCl_3$) δ 7.84 (2H, s), 7.80 (1H, s), and 1.68 (6H, s).

DESCRIPTION 11

α,α-Dimethyl-3,5-bis(trifluoromethyl) benzenemethanamine Hydrochloride

Diphenylphosphoryl azide (0.43 mL, 2 mmol) was added to a solution of α,α-dimethyl-3,5-bis(trifluoromethyl) benzeneacetic acid (Description 10, 0.5 g, 1.67 mmol) and triethylamine (0.6 mL, 4.2 mmol) in toluene (20 mL) and the mixture was stirred at 90° C. for 18 hours. The mixture was cooled, diluted with ethyl acetate and washed with aqueous sodium carbonate (saturated), dried ($MgSO_4$) and the solvent was evaporated under reduced pressure. Hydrochloric acid (5M, 15 mL) was added and the mixture was heated under reflux for 18 hours. The mixture was cooled, basified with aqueous sodium hydroxide (4M) and extracted with ethyl acetate. The combined organic fractions were washed with water, dried ($MgSO_4$), and the solvent was evaporated under reduced pressure. The residue was dissolved in diethyl ether and ethereal hydrogen chloride (1M) was added. The solid was collected, washing with diethyl ether, and dried in vacuo to give the title compound as a colorless solid (100 mg, 20%). m/z ($ES^+$) 272 (M+1), 255 (M+1-$NH_3$).

DESCRIPTION 12

(RS)-Methyl α-Amino-3,5-bis(trifluoromethyl) benzeneacetate Hydrochloride

Palladium on carbon (5%, 220 mg) was added to a solution of methyl α-diazo-3,5-bis(trifluoromethyl) benzeneacetate (WO 9521819, 1.22 g, 3.91 mmol) in methanol/acetic acid (3:1, 33 mL) and the mixture was shaken under an atmosphere of hydrogen (40 psi) for 18 hours. The mixture was filtered through a glass fibre pad and the solvent was evaporated under reduced pressure. Ethyl acetate (100 mL) and aqueous sodium carbonate (10%, 100 mL) were added and the layers were separated. The aqueous fraction was extracted with ethyl acetate (50 mL) and the combined organic fractions were dried ($NA_2SO_4$) and the solvent was evaporated under reduced pressure. The residue was dissolved in ethyl acetate (30 mL) and ethereal hydrogen chloride (1M, 5 mL) was added. The solid was collected, washing with ethyl acetate and ether, and dried in vacuo to give the title compound (432 mg, 33%). m/z ($ES^+$) 302 (M+1).

DESCRIPTION 13

2-(Cyclopropyloxy)-5-(trifluoromethoxy) phenylmethyl Methanesulfonate

Methanesulfonyl chloride (0.31 mL, 0.46 g, 4.0 mmol) was added dropwise to a stirred, cooled (−10° C.) solution of 2-(cyclopropyloxy)-5-(trifluoromethoxy) benzenemethanol (WO9900368, 0.5 g, 2.0 mmol) and triethylamine (0.56 mL, 0.40 g, 4.0 mmol) in dichloromethane (10 mL) and the mixture was stirred at 0° C. for 30 minutes, then at room temperature for 2 hours. Water (50 mL) was added and the mixture was extracted with ethyl acetate (2×50 mL). The combined organic fractions were washed with aqueous citric acid (10%, 20 mL), aqueous sodium hydrogen carbonate (saturated, 50 mL) and brine (50 mL), dried ($MgSO_4$) and the solvent was evaporated under reduced pressure to give the title compound. $^1$H NMR (400 MHz, $CDCl_3$) δ 7.28–7.22 (3H, m), 5.20 (2H, s), 3.80–3.77 (1H, m), 3.01 (3H, s), and 0.85–0.79 (4H, m).

DESCRIPTION 14

4-(4-Fluorophenyl)pyridine

A mixture of 4-fluorobenzeneboronic acid (38.7 g, 276 mmol), 4-bromopyridine hydrochloride (48.9 g, 250 mmol), [1,4-butanediylbis(diphenylphosphine-κP)] dichloropalladium (*Organometallics* 1998, 17, 661; 1.52 g, 2.5 mmol), 1,2-dimethoxyethane (500 mL) and sodium carbonate solution (2M, 440 mL) was degassed with bubbling nitrogen and stirred at 80° C. for 24 hours. The mixture was cooled and extracted with ethyl acetate. The combined organic fractions were dried ($MgSO_4$) and the solvent was evaporated under reduced pressure to give the crude title compound as a brown solid (50.87 g) which was used without further purification. $^1$H NMR (360 MHz, $CDCl_3$) δ 8.65 (2H, m), 7.61 (2H, m), 7.49 (2H, dd, J 1.6, 4.6 Hz), and 7.09 (2H, m).

DESCRIPTION 15

4-(4-Fluorophenyl)-1,2,3,6-tetrahydro-1-(phenylmethyl)pyridine

Benzyl bromide (52.4 mL, 441 mmol) was added to a solution of 4-(4-fluorophenyl)pyridine (Description 14, 50.87 g, 294 mmol) in acetone (500 mL) and the mixture was heated under reflux for 3 days. The mixture was cooled to room temperature and the solid was collected, washed with acetone and diethyl ether and dried in vacuo. The solid was dissolved in methanol (400 mL) and water (100 mL), cooled to 0° C. and sodium borohydride (20.6 g, 542 mmol) was added in portions. The mixture was stirred at room temperature for 1 hour, then heated to reflux for 18 hours. The mixture was cooled and the solvent was evaporated under reduced pressure. Dichloromethane (300 mL) and water (200 mL) were added and the layers were separated. The organic layer was dried ($MgSO_4$) and the solvent was evaporated under reduced pressure to give the title compound as a light brown oil (61.5 g, 78%). m/z ($ES^+$) 268 (M+1).

DESCRIPTION 16

4-(4-Fluorophenyl)piperidine

Palladium hydroxide on carbon (20%, 5 g) was added to a solution of 4-(4-fluorophenyl)-1,2,3,6-tetrahydro-1-(phenylmethyl)pyridine (Description 15, 60 g, 225 mmol) in methanol (500 mL) and the mixture was shaken under an atmosphere of hydrogen (50 psi) for 48 hours. The mixture was filtered through a glass fibre pad, washing with methanol, and the solvent was evaporated under reduced pressure. The residue was dissolved in ethyl acetate and ethereal hydrogen chloride (1M, 300 mL) was added. The solid was collected and recrystallised from 2-propanol to give 4-(4-fluorophenyl)piperidine hydrochloride as a colorless solid (30.5 g, 63%). $^1$H NMR (400 MHz, $CD_3OD$) δ 7.31–7.27 (2H, m), 7.09–7.03 (2H, m), 3.48 (2H, m), 3.30 (2H, td, J 3.0, 13.1 Hz), 2.91 (1H, m), 2.05 (2H, m), and 1.87 (2H, m). m/z ($ES^+$) 180 (M+1).

A sample (1 g, 4.64 mmol) was suspended in ethyl acetate and washed with saturated aqueous sodium carbonate. The organic layer was dried ($MgSO_4$) and the solvent was evaporated under reduced pressure to give the title compound as a colorless oil (825 mg, 99%). $^1$H NMR (400 MHz, $CD_3OD$) δ 7.25–7.21 (2H, m), 7.02–6.97 (2H, m), 3.14 (2H, m), 2.78–2.64 (3H, m), 1.80 (2H, m), and 1.63 (2H, m). m/z ($ES^+$) 180 (M+1).

DESCRIPTION 17

Benzenebutanal 1,1,1-Tris(acetyloxy)-1,1-dihydro-1,2-benziodoxol-3 (1H)-one (1.7 g, 4.0 mmol) was added to a solution of benzenebutanol (0.5 g, 3.3 mmol) in dichloromethane (10 mL) and the mixture was stirred at room temperature for 2 hours. The mixture was filtered through a plug of silica gel, washing with dichloromethane, and the solvent was evaporated under reduced pressure to give the title compound as a colorless oil (466 mg, 95%). $^1$H NMR (400 MHz, CDCl$_3$) δ 9.76 (1H, m), 7.31–27 (2H, m), 7.22–7.16 (3H, m), 2.66 (2H, t, J 73 Hz), 2.45 (2H, t, J 7.3 Hz), 1.97 (2H, quin, J 7.3 Hz).

DESCRIPTION 18

Methyl 4-Oxo-1-phenylcyclohexanecarboxylate

Acetyl chloride (0.46 mL, 0.50 g, 6.4 mmol) was added to a solution of 4-oxo-1-phenylcyclohexanecarboxylic acid (Description 2, 0.94 g, 4.3 mmol) in methanol (5 mL) and the mixture was heated under reflux for 20 hours. The mixture was cooled, poured into aqueous sodium hydrogen carbonate (saturated, 100 mL) and extracted with ethyl acetate (2×50 mL). The combined organic fractions were dried (Na$_2$SO$_4$) and the solvent was evaporated under reduced pressure. The residue was dissolved in tetrahydrofuran (2 mL), acetic acid (6 mL) and water (2 mL) were added and the mixture was stirred at 45° C. for 2 hours. The mixture was cooled, the solvent was evaporated under reduced pressure and aqueous sodium hydrogen carbonate (saturated, 100 mL) was added. The mixture was extracted with ethyl acetate (2×50 mL), the combined organic fractions were dried (Na$_2$SO$_2$) and the solvent was evaporated under reduced pressure to give the tide compound (0.98 g, 98%). $^1$H NMR (250 MHz, CDCl$_3$) δ 7.45–7.26 (5H, m), 3.72 (3H, s), 2.77 (2H, m), 2.61–2.38 (4H, m), and 2.25 (2H, m).

DESCRIPTION 19

Cis-Methyl 4-[4-(4-Fluorophenyl)piperidin-1-yl]-1-phenylcyclohexanecarboxylate,

Cis-4-[4-(4-Fluorophenyl)piperidin-1-yl]-1-phenylcyclohexanecarboxylic Acid and

Trans-Methyl 4-[4-(4-Fluorophenyl)piperidin-1-yl]-1-phenylcyclohexanecaboxylate A solution of sodium cyanoborohydride (0.93 g, 14.9 mmol) and zinc chloride (1.01 g, 7.45 mmol) in methanol (30 mL) was added to a solution of methyl 4oxo-1-phenylcyclohexanecarboxylate (Description 18, 3.45 g, 14.9 mmol) and 4-(4-fluorophenyl)piperidine (Description 16, 3.2 g, 17.9 mmol) in methanol (50 mL) and the mixture was stirred at room temperature for 24 hours. The mixture was poured into water and extracted with ethyl acetate and the combined organic fractions were dried (MgSO$_4$), and the solvent was evaporated under reduced pressure. The residue was recrystallised from ethanol to give cis-methyl 4-[4-(4-fluorophenyl)piperidin-1-yl]-1-phenylcyclohexanecarboxylate (0.9 g, 15%) as a colorless solid. $^1$H NMR (400 MHz, CD$_3$OD) δ 7.38–7.36 (2H, m), 7.33–7.29 (2H, m), 7.26–7.20 (3H, m), 7.02–6.98 (2H, m), 3.66 (3H, s), 3.10 (2H, m), 2.71 (2H, m), 2.56–2.52 (1H, m), 2.43–2.32 (3H, m), 2.05 (2H, m), 1.84 (2H, m), 1.78–1.62 (4H, m), and 1.54–1.48 (2H, m). m/z (ES$^+$) 396 (M+1).

The mother liquors from the recrystallisation were collected and the solvent was evaporated under reduced pressure. Methanol (20 mL) and hydrochloric acid (6M, 200 mL) were added and the mixture was heated under reflux for 3 days. The mixture was cooled and the solvent was evaporated under reduced pressure. The residue was dissolved in methanol (100 mL) and acetyl chloride (0.77 mL, 10.8 mmol) was added slowly. The mixture was heated under reflux for 6 hours, cooled and the solvent was evaporated under reduced pressure. Ethyl acetate and aqueous sodium carbonate (saturated) were added and the layers were separated. The solid which formed in the organic layer was collected and dried in vacuo to give cis-methyl 4-[4-(4-fluorophenyl)piperdin-1-yl]-1-phenylcyclohexanecarboxylic acid as a colorless solid (1.2 g, 21%). m/z (ES$^+$) 382 (M+1).

The mother liquors from the recrystallisation were dried (MgSO$_4$) and the solvent was evaporated under reduced pressure to give trans-methyl 4-[4-(4-fluorophenyl)piperidin-1-yl]-1-phenylcyclohexaecarboxylate as a colorless solid, (1.6 g, 27%).

$^1$H NMR (400 MHz, CD$_3$OD) δ 7.51–7.48 (2H, m), 7.38–7.34 (2H, m), 7.24–7.17 (3H, m), 6.98–6.94 (2H, m), 3.56 (3H, s), 3.00 (2H, m), 2.79 (2H, m), 2.48–2.41 (2H, m), 2.24–2.17 (2H, m), 1.96–1.86 (4H, m), 1.75 (2H, m), 1.70–1.63 (2H, m), and 1.43–1.37 (2H, m). m/z (ES$^+$) 396 (M+1).

DESCRIPTION 20

Trans-4-[4-(4-Fluorophenyl)piperidin-1-yl]-1-phenylcyclohexanecarboxylic Acid Hydrochloride Hydrochloric acid (6M, 100 mL) was added to a suspension of trans-methyl 4-[4-(4-fluorophenyl)piperidin-1-yl]-1-phenylcyclohexanecarboxylate (Description 19, 1.6 g, 4.05 mmol) in methanol (10 mL) and the mixture was heated under reflux for 48 hours. The mixture was cooled and the solvent was evaporated under reduced pressure to give the title compound as a colorless solid (1.5 g, 89%). m/z (E$^+$) 382 (M+1).

DESCRIPTION 21

Trans-4-[4-(4-Fluorophenyl)piperidin-1-yl]-1-phenylcyclohexanemethanol

Diisobutylaluminium hydride (1M in hexanes, 1.95 mL, 1.95 mmol) was added slowly to a cooled (−78° C.) solution of trans-methyl 4-[4-(4-fluorophenyl)piperidin-1-yl]-1-phenylcyclohexanecarboxylate (Description 19, 235 mg, 0.59 mmol) in dichloromethane (10 mL) and hexane (10 mL). The mixture was allowed to warm to room temperature and stirred for 18 hours. The mixture was poured into aqueous ammonium chloride (saturated) and extracted with dichloromethane. The combined organic fractions were dried (MgSO$_4$) and the solvent was evaporated under reduced pressure to give the title compound as a pale yellow foam (230 mg, 100%). m/z (ES$^+$) 368 (m+1).

DESCRIPTION 22

(RS)-α-Methyl-8-phenyl-1,4-dioxaspiro[4.5]decane-8-methanol

A solution of 8-phenyl-1,4-dioxaspiro[4.5]decane-8-carboxaldehyde (*J. Med. Chem.* 1975, 18, 593–599; 4 g, 16.2 mmol) in tetrahydrofuran (100 mL) was added dropwise to a solution of methyl magnesium bromide (3.0M in ether, 8.1 mL, 24.3 mmol) in tetrahydrofuran (50 mL) at 0° C. The mixture was allowed to warm to room temperature over 4 hours, then aqueous ammonium chloride (saturated, 75 mL), water (75 mL) and ethyl acetate (100 mL) were added. The layers were separated and the organic fraction was dried (MgSO$_4$) and the solvent was evaporated under reduced pressure to give the title compound as a colorless solid (4.03 g, 96%). $^1$H NMR (360 MHz, CDCl$_3$) δ 0.96 (3H, d, J 6.5 Hz), 1.12 (1H, br s), 1.40–1.66 (4H, m), 1.76–1.86 (2H, m), 2.24–2.28 (1H, m), 2.46–2.51 (1H, m), 3.61–3.64 (1H, m), 3.58–3.96 (4H, m), and 7.21–7.38 (5H, m).

DESCRIPTION 23

(RS)-α-Ethenyl-8-phenyl-1,4-dioxaspiro[4.5]decane-8-methanol

Prepared from 8-phenyl-1,4-dioxaspiro[4.5]decane-8-carboxaldehyde (*J. Med. Chem.* 1975, 18, 593–599) and vinylmagnesium bromide according to the method of Description 22. $^1$H NMR (400 MHz, CDCl$_3$) δ 1.31 (1H, br s), 1.42–1.69 (4H, m), 1.76–1.89 (2H, m), 2.23–2.28 (1H, m), 2.45–2.51 (1H, m), 3.85–3.96 (5H, m), 5.09–5.14 (2H, m), 5.55–5.63 (1H, m), and 7.21–7.39 (5H, m).

DESCRIPTION 24

Trans-4-(4-Oxopiperidin-1-yl)-1-phenylcyclohexanecarboxylic Acid Hydrochloride Sodium acetoxyborohydride (7.0 g, 32.9 mmol) was added to a degassed solution of 4-oxo-1-phenylcyclohexanecarboxylic acid (Description 2, 5.98 g, 27.4 mmol) and 1,4-dioxa-8-azaspiro[4.5]decane (4.32 g, 30.2 mmol) in dichloroethane (125 mL) and the mixture was stirred at room temperature for 20 hours. The solvent was evaporated under reduced pressure, methanol (120 mL) was added and the mixture was stirred at room temperature for 1 hour. The mixture was filtered and cooled to 0° C. Acetyl chloride (10 mL) was added slowly and the mixture was heated under reflux for 20 hours. The mixture was cooled, filtered and the solvent was evaporated under reduced pressure. Aqueous sodium carbonate (saturated, 200 mL) was added and the mixture was extracted with ethyl acetate (2×200 mL). The combined organic fractions were dried (Na$_2$SO$_4$) and the solvent was evaporated under reduced pressure. Hydrochloric acid (5M, 300 mL) was added and the mixture was heated under reflux for 20 hours. The mixture was cooled and the solvent was evaporated under reduced pressure to give the title compound (3.36 g, 36%). m/z (ES$^+$) 302 (M+1).

DESCRIPTION 25

Trans-4-[4(Phenylmethyl)piperazin-1-yl]-1-phenylcyclohexanecarboxylate Acid Hydrochloride Prepared from 4-oxo-1-phenylcyclohexanecarboxylic acid (Description 2) and 1-(phenylmethyl) piperazine according to the method of Description 24. m/z (ES$^+$) 379 (M+1).

DESCRIPTION 26

Cis-(RS)-4-Hydroxy-1-phenyl-N-{1-[3,5-bis(trifluoromethyl)phenyl]ethyl}cyclohexanecarboxamide Sodium borohydride (0.31 g, 8.3 mmol) in ethanol (10 mL) was added dropwise over 10 minutes to a stirred, cooled (0° C.) solution of (RS)-4-oxo-1-phenyl-N-{1-[3,5-bis(trifluoromethyl)phenyl]ethyl}cyclohexanecarboxamide (Example 18, 1.90 g, 4.1 mmol) in ethanol (60 mL). The mixture was stirred at 0° C. for 30 minutes, then hydrochloric acid (2M, 20 mL) was added. The mixture was stirred at room temperature for 10 minutes, then the pH was adjusted to 7.0 with aqueous potassium carbonate (saturated) and the ethanol was evaporated under reduced pressure. Water (50 mL) was added and the mixture was extracted with ethyl acetate (3×50 mL). The combined organic fractions were washed with aqueous sodium hydrogen carbonate (saturated, 2×50 mL) and brine (50 mL), dried (MgSO$_4$) and the solvent was evaporated under reduced pressure. The residue was crystallized from EtOH/H$_2$O (50:50, 30 mL) and the solid was collected and dried in vacuo at 40° C. to give the title compound (1.37 g, 72%). $^1$H NMR (400 MHz, CD$_3$OD) δ 7.76 (1H, s), 7.69 (2H, s), 7.32–7.17 (5H, m), 5.16 (1H, q, J 7.1 Hz), 3.60 (1H, m), 2.62 (2H, m), 1.97–1.47 (6H, m), and 1.43 (3H, d, J 7.1 Hz).

DESCRIPTION 27

Cis-(RS)-4-Methanesulfonyloxy-N-{1-[3,5-bis(trifluoromethyl)phenyl]ethyl}-1-phenylcyclohexanecarboxamide Methanesulfonyl chloride (0.9 mL, 11.6 mmol) was added to a stirred, cooled (0° C.) solution of cis-(RS)-4-hydroxy-1-phenyl-N-{1-[3,5-bis(trifluoromethyl)phenyl]ethyl}cyclohexanecarboxamide (Description 26, 1.33 g, 2.9 mmol) and pyridine (0.94 mL, 11.6 mmol) in dichloromethane (100 mL) and the mixture was stirred at room temperature for 24 hours. The mixture was washed with aqueous citric acid (10%) and aqueous sodium hydroxide (1M), dried (MgSO$_4$), filtered and the solvent was evaporated under reduced pressure to give the title compound as a colorless foam (1.44 g, 95%). $^1$H NMR (400 MHz, CDCl$_3$) δ 7.72 (1H, s), 7.44 (2H, s), 7.42–7.38 (2H, m), 7.35–7.31 (3H, m), 5.41 (1H, d, J 6.9 Hz), 5.07 (1H, m), 4.78 (1H, m), 3.03 (3H, s), 2.60–2.40 (2H, m), 2.14–1.87 (6H, m), and 1.35 (3H, d, J 7.0 Hz).

DESCRIPTION 28

Trans-(RS)-4-Azido-N-{1-[3,5-bis(trifluoromethy)phenyl]ethyl}-1-phenylcyclohexanecarboxamide Sodium azide (621 mg, 9.55 mmol) was added to a solution of cis-(RS)-4-methanesulfonyloxy-N-{1-[3,5-bis(trifluoromethyl)phenyl]ethyl}-1-phenylcyclohexanecarboxamide (Description 27, 1.0 g, 1.91 mmol) in dimethylformamide (15 mL) and the mixture was then stirred at 90° C. for 24 hours. The mixture was cooled, poured into aqueous ammonium chloride (saturated) and extracted with ethyl acetate. The combined organic fractions were washed with aqueous ammonium chloride (saturated) and water, dried (MgSO$_4$), filtered and the solvent was evaporated under reduced pressure to give the title compound as a yellow solid (920 mg, 100%). $^1$H NMR (400 MHz, CDCl$_3$) δ 7.72 (1H, s), 7.45–7.31 (7H, m), 5.34 (1H, d, J 7.0 Hz), 5.03 (1H, m), 3.63 (1H, m), 2.41–2.37 (1H, m), 2.23–2.12 (3H, m), 1.99–1.93 (2H, m), 1.67–1.47 (2H, m), and 1.30 (3H, d, J 7.0 Hz).

DESCRIPTION 29

Trans-(RS)-4-Cyano-N-{1-[3,5-bis(trifluoromethyl)phenyl]ethyl}-1-phenylcyclohexanecarboxamide Tetrabutylammonium cyanide (153 mg, 0.57 mmol) was dried azeotropically by evaporating toluene under reduced pressure, then a solution of cis-(RS)-4methanesulfonyloxy-N-{1-[3,5-bis(trifluoromethyl)phenyl]ethyl}-1-phenylcyclohexanecarboxamide (Description 27, 100 mg, 0.19 mmol) in toluene (10 mL) was added and the mixture was stirred at 70° C. for 9 hours. Further tetrabutylammonium cyanide (153 mg, 0.57 mmol) was added and the mixture was stirred at 70° C. for 24 hours. The mixture was poured into water (50 mL) and extracted with ethyl acetate (2×50 mL). The combined organic fractions were washed with water (50 mL) and brine (50 mL), dried (MgSO$_4$) and the solvent was evaporated under reduced pressure. The residue was purified by flash column chromatography on silica gel, eluting with isohexane/EtOAc (80:20), to give the title compound (50 mg, 56%). $^1$H NMR (360 MHz, CD$_3$OD) δ 7.76 (1H, s), 7.66 (2H, s), 7.36–7.22 (5H, m), 5.12 (1H, q, J 7.0 Hz), 3.00–2.96 (1H, m), 2.48–2.39 (2H, m), 2.29–2.21 (1H, m), 2.04–1.79 (5H, m), and 1.41 (3H, d, J 7.0 Hz).

DESCRIPTION 30

Cis- and Trans-4-[4-(4-Fluorophenyl)piperidin-1-yl]-1-phenylcyclohexanecarbonitrile Prepared as a mixture of cis- and trans-isomers from 4-oxo-1-phenylcyclohexanecarbonitrile and 4-(4-fluorophenyl)piperidine (Description 16) according to the method of Example 55. m/z (ES$^+$) 363 (M+1).

DESCRIPTION 31

Trans-4-[4-(4-Fluorophenyl)piperidin-1-yl]-1-phenylcyclohexanecarbonitrile

Prepared from the mixture of isomers of Description 30 by flash column chromatography on silica gel, eluting with CH$_2$Cl$_2$/MeOH/NH$_3$(Aq.) (98:2:0.2). m/z (ES$^+$) 363 (M+1).

DESCRIPTION 32

Trans-4-[4-(4-Fluorophenyl)piperidin-1-yl]-1-phenylcyclohexanemethanamine

Lithium aluminium hydride (1M in ether, 0.69 mL, 0.69 mmol) was added to a solution of trans-4-[4-(4-fluorophenyl)piperidin-1-yl]-1-phenylcyclohexanecarbonitrile (Description 31, 250 mg, 0.69 mmol) in ether (10 mL) and the mixture was stirred at room temperature for 1 hour. Water (0.5 mL), aqueous sodium hydroxide (1M, 1 mL) and water (1.5 mL) were added and the mixture was stirred at room temperature for 10 minutes. The mixture was filtered, washing with ether, and the layers were separated. The organic layer was washed with brine (10 mL), dried (MgSO$_4$) and the solvent was evaporated under reduced pressure to give the title compound (243 mg, 96%). m/z (ES$^+$) 367 (M+1).

DESCRIPTION 33

2-({(2-[3,5-Bis(trifluoromethyl)phenyl]ethyl}thio)benzothiazole

Tributylphosphine (3.46 mL, 2.81 g, 13.9 mmol) was added over 30 minutes to a mixture of 3,5-bis(trifluoromethyl)benzeneethanol (3.26 g, 12.6 mmol) and 2,2'-dithiobis(benzothiazole) (4.20 g, 12.6 mmol) in tetrahydrofuran (120 mL) and the mixture was stirred at room temperature for 2 hours. The solvent was evaporated under reduced pressure and water (150 mL) was added. The mixture was extracted with ether (2×150 mL) and the combined organic fractions were dried (Na$_2$SO$_4$) and the solvent was evaporated under reduced pressure. The residue was purified by flash column chromatography on silica gel, eluting with isohexane/EtOAc (90:10) to give the title compound (3.87 g, 75%). m/z (ES$^+$) 408 (M+1).

DESCRIPTION 34

2-({(2-[3,5-Bis(trifluoromethyl)phenyl]ethyl}sulfonyl)benzothiazole

Oxone (8.58 g, 14.0 mmol) was added to a mixture of 2-({(2-[3,5-bis(trifluoromethyl)phenyl]ethyl}thio)benzothiazole (Description 33, 2.47 g, 6.1 mmol) and wet alumina (7 g) in chloroform (100 mL) and the mixture was heated under reflux for 1 hour. The mixture was cooled, filtered and the solvent was evaporated under reduced pressure to give the title compound (2.62 g, 99%). m/z (ES$^+$) 440 (M+1).

DESCRIPTION 35

(E)-8-Phenyl-8-{3-[3,5-bis(trifluoromethyl)phenyl]prop-1-enyl}-1,4-dioxaspiro[4.5]decane Lithium hexamethyldisilazide (1M in tetrahydrofuran, 7.0 mL, 7.0 mmol) was added over 10 minutes to a cooled (−78° C.) solution of 8-phenyl-1,4-dioxaspiro[4,5]decane-8-carboxaldehyde (J. Med. Chem. 1975, 18, 593–599, 1.68 g, 6.8 mmol) and 2-({(2-[3,5-bis(trifluoromethyl)phenyl]ethyl}sulfonyl)benzothiazole (Description 34, 2.99 g, 6.8 mmol) in tetrahydrofuran (15 mL) and the mixture was stirred at −78° C. for 1 hour, then allowed to warm to room temperature. Aqueous ammonium chloride (saturated, 10 mL) was added and the mixture was stirred at room temperature for 30 minutes. Water (5 mL) was added and the mixture was extracted with ethyl acetate (3×30 mL). The combined organic fractions were washed with brine (50 mL), dried (MgSO$_4$) and the solvent was evaporated under reduced pressure. The residue was purified by flash column chromatography on silica gel, eluting with isohexane/EtOAc (90:10) to give the tide compound as a pale yellow oil (2.43 g, 92%).

$^1$H NMR (400 MHz, CDCl$_3$) δ 7.70 (1H, s), 7.56 (2H, s), 7.36–7.18 (5H, m), 5.65 (1H, d, J 15.3 Hz), 5.41 (1H, dt, J$_d$ 15.3, J$_t$ 7.0 Hz), 3.94 (4H, m), 3.45 (2H, d, J 7.0 Hz), 2.22 (2H, m), 1.99 (2H, m), and 1.75–1.61 (4H, m).

DESCRIPTION 36

Trans-(RS)-4-Methyl-3-piperidinol Hydrochloride

A slurry of palladium on carbon (10%, 600 mg) in ethanol (10 mL) was added to a solution of trans-(RS)-4-methyl-1-(phenylmethyl)-3-piperidinol (Tetrahedron 1970, 26, 5519–5527, 6 g, 29.2 mmol) and hydrochloric acid (2M, 10 mL) in ethanol (100 mL) and the mixture was shaken under hydrogen (50 psi) for 42 hours. The mixture was filtered through Celite™ and the solvent was evaporated under reduced pressure. Toluene (50 mL) was added and evaporated under reduced pressure to give the title compound as a colorless solid (4.4 g, 99%). m/z (ES$^+$) 115 (M+1).

DESCRIPTION 37

Trans-(RS)-1,1-Dimethylethyl 3-Hydroxy-4-methylpiperidinecarboxylate

Di-tert-butyl dicarbonate (4.32 g, 20 mmol) was added to a solution of trans-(RS)-4methyl-3-piperidinol hydrochloride (Description 36, 2.93 g, 19.4 mmol) and triethylamine (4.1 mL, 29 mmol) in dichloromethane (150 mL) and the mixture was stirred at room temperature for 16 hours. N,N-Dimethylethylenediamine (506 μL) was added and the mixture was stirred at room temperature for 16 hours. The mixture was washed with aqueous citric acid (10%, 100 mL), dried (MgSO$_4$), and the solvent was evaporated under reduced pressure to give the title compound as a colorless oil (4.0 g, 96%). m/z (ES$^+$) 159 (M+1).

DESCRIPTION 38

(RS)-1,1-Dimethylethyl 4-Methyl-3-oxopiperidinecarboxylate 1,1,1-Tris(acetyloxy)-1,1-dihydro-1,2-benziodoxol-3 (1H)-one (4.17 g, 0.13 mmol) was added to a solution of trans-(RS)-1,1-dimethylethyl 3-hydroxy-4-methylpiperidinecarboxylate (Description 37, 2 g, 9.3 mmol) in dichloromethane (60 mL) and the mixture was stirred at room temperature for 60 minutes. Aqueous sodium bisulfite (10%, 50 mL) was added) and the mixture was stirred at room temperature for 5 minutes. Saturated aqueous sodium hydrogen carbonate (50 mL) was added and the layers were separated. The organic fraction was dried (MgSO$_4$) and the solvent was evaporated under reduced pressure to give the title compound (1.96 g, 99%). m/z (ES$^+$) 157 (M+1).

DESCRIPTION 39

(RS)-3,3-Difluoro-4-methylpiperidine Hydrochloride

Diethylaminosulphur trifluoride (1.18 mL, 8.97 mmol) was added to a stirred, cooled (0° C.) solution of (RS)-1,1-dimethylethyl 4-methyl-3-oxopiperidinecarboxylate (Description 38, 500 mg, 2.24 mmol) in dichloromethane and the mixture was stirred at room temperature for 16 hours. Ice (5 g) and water (5 mL) were added and the mixture was stirred at room temperature for 20 minutes. The layers were separated and the aqueous layer was extracted with dichloromethane (2×50 mL). The combined organic fractions were washed with brine (50 mL), dried (MgSO$_4$) and the solvent was evaporated under reduced pressure. The residue was suspended in diethyl ether (50 mL) and treated with methanolic hydrogen chloride (1M, 3 mL). The mixture was stirred at room temperature for 30 minutes, then the solvent was evaporated under reduced pressure to give the title compound as a solid (303 mg, 78%). m/z (ES$^+$) 136 (M+1).

DESCRIPTION 40

1-(1,1-Dimethylethyl) 4-Ethyl 4-(2-Propenyl)-1,4-piperidinedicarboxylate

A solution of 1-(1,1-dimethylethyl) 4-ethyl 1,4-piperidinedicarboxylate (25.0 g, 97 mmol) in tetrahydrofuran (100 mL) was added slowly to a stirred, cooled (−78° C.) solution of potassium hexamethyldisilazide (29.0 g, 145 mmol) in tetrahydrofuran (150 mL), maintaining the internal temperature below −65° C. The mixture was stirred at −78° C. for 30 minutes, then 3-bromopropene (12.6 mL, 145 mmol) was added dropwise over 10 minutes. The mixture was stirred at −78° C. for 1 hour, then saturated aqueous ammonium chloride (400 mL) and water (100 mL) were added and the mixture was warmed to room temperature. The mixture was extracted with ethyl acetate (3×400 mL) and the combined organic fractions were washed with aqueous citric acid (10%, 2×250 mL), saturated aqueous sodium hydrogen carbonate (400 mL) and brine (200 mL), dried (MgSO$_4$) and the solvent was evaporated under reduced pressure to give the title compound (29.3 g, 100%). $^1$H NMR (400 MHz, CDCl$_3$) δ 5.75–5.60 (1H, m), 5.10–5.00 (2H, m), 4.16 (2H, q, J 7 Hz), 3.92–3.78 (2H, m), 2.90 (2H, br t, J 14 Hz), 2.26 (2H, d, J 7 Hz), 2.08 (2H, br d, J 14 Hz), 1.45 (9H, s), 1.45–1.30 (2H, m), and 1.26 (3H, t, J 7 Hz).

DESCRIPTION 41

1,1-Dimethylethyl 1-Oxo-2-oxa-8-azaspiro[4.5]decane-8-carboxylate 1-(1,1-Dimethylethyl) 4-ethyl 4-(2-propenyl)-1,4-piperidinedicarboxylate (Description 40, 20.0 g, 67.2 mmol) was dissolved in methanol (300 mL) and dichloromethane (300 mL) and cooled to −78° C. Oxygen was bubbled through the solution for 10 minutes, then ozone for 75 minutes, to give a persistant blue coloration. Oxygen was bubbled through the solution for 10 minutes, then nitrogen for 10 minutes. Sodium borohydride (5.1 g, 135 mmol) was added and the mixture was stirred at −78° C. for 1 hour. Further sodium borohydride (5.1 g, 135 mmol) was added and the mixture was stirred at room temperature for 16 hours. Acetone (75 mL) was added and the mixture was stirred at room temperature for 10 minutes. Water (50 mL) was added and the organic solvent was evaporated under reduced pressure. Saturated aqueous ammonium chloride (500 mL) was added and the mixture was extracted with ethyl acetate (2×500 mL). The combined organic fractions were washed with aqueous citric acid (10%, 500 mL), saturated aqueous sodium hydrogen carbonate (500 mL) and brine (200 mL), dried (Na$_2$SO$_4$) and the solvent was evaporated under reduced pressure to give the title compound (15.0 g, 88%). $^1$H NMR (400 MHz, CDCl$_3$) δ 4.31 (2H, t, J 7 Hz), 3.97–3.87 (2H, m), 3.17–3.07 (2H, m), 2.20 (2H, t, J 7 Hz), 1.92–1.82 (2H, m), 1.60–1.45 (2H, m), and 1.45 (9H, s).

DESCRIPTION 42

1,1-Dimethylethyl 4-(2-Hydroxyethyl)-4-hydroxymethyl)-1-piperidinecarboxylate Diisobutylaluminium hydride (1.0M in dichloromethane, 3.60 mL, 3.60 mmol) was added over 10 minutes to a stirred, cooled (−78° C.) solution of 1,1-dimethylethyl 1-oxo-2-oxa-8-azaspiro[4.5]decane-8-carboxylate (Description 41, 400 mg, 1.57 mmol) in dichloromethane (4 mL) and the mixture stirred at −78° C. for 3 hours, then at 0° C. for 2 hours. Water (1.6 mL) was added very slowly at 0° C. and the mixture was warmed to room temperature and stirred overnight. The mixture was filtered through Hyflo™, washing with dichloromethane, and the solvent was evaporated under reduced pressure. The residue was purified by flash column chromatography on silica gel, eluting with ethyl acetate, to give the title compound (255 mg, 63%). m/z (ES$^+$) 260 (M+1).

DESCRIPTION 43

1,1-Dimethylethyl 2-Oxa-8-azaspiro[4.5]decane-8-carboxylate

Diethyl azodicarboxylate (183 μl, 1.16 mmol) in tetrahydrofuran (0.5 mL) was added dropwise to a stirred, cooled (0° C.) solution of 1,1-dimethylethyl 4-(2-hydroxyethyl)-4-(hydroxymethyl)-1-piperidinecarboxylate (Description 42, 250 mg, 0.96 mmol) and triphenylphosphine (303 mg, 1.16 mmol) in tetrahydrofuran (10 mL) and the mixture was stirred at 0° C. for 90 minutes then at room temperature overnight. The mixture was cooled to 0° C. and further triphenylphosphine (126 mg, 0.48 mmol) and diethyl azodicarboxylate (76 μl, 0.48 mmol) were added. The mixture was stirred at room temperature for 2.5 hours, then the solvent was evaporated under reduced pressure and the residue was purified by flash column chromatography on silica gel, eluting with isohexane/EtOAc (80:20), to give the title compound as a colorless oil (150 mg, 65%). m/z (ES$^+$) 186 (M+1-C$_4$H$_8$).

DESCRIPTION 44

2-Oxa-8-azaspiro[4.5]decane

Methanolic hydrogen chloride (3M, 3 mL) was added to a stirred, cooled (0° C.) solution of 1,1-dimethylethyl 2-oxa-8-azaspiro[4.5]decane-8-carboxylate (Description 43, 150 mg, 0.62 mmol) in methanol and the mixture was stirred at room temperature for 24 hours. The solvent was evaporated under reduced pressure and the residue was dissolved in methanol and passed through Amberlyst 26 ion exchange resin, eluting with methanol. The solvent was evaporated under reduced pressure and the residue was dissolved in dichloromethane, dried (Na$_2$SO$_4$) and the solvent was evaporated under reduced pressure to give the title compound (77 mg, 88%). m/z (ES$^+$) 142 (M+1).

EXAMPLE 1

1-{[(1,4-Dioxa-8-phenylspiro[4.5]decan-8-yl)methoxy]methyl}-2-methoxybenzene

Sodium hydride (60% dispersion in mineral oil, 720 mg, 30.0 mmol) was added to a solution of 8-phenyl-1,4-dioxaspiro[4.5]decane-8-methanol (*J. Org. Chem.* 1974, 39, 2311–2313, 1.5 g, 6.0 mmol) in dimethylformamide (20 mL) and the mixture was stirred at room temperature for 1 hour. 1-(Chloromethyl)-2-methoxybenzene (816 mg, 6.0 mmol) was added and the mixture was stirred overnight at 50° C. The mixture was cooled, poured into water (50 mL) and extracted with ether (2×50 mL). The combined organic fractions were washed with water (3×50 mL) and brine (50 mL), dried (MgSO$_4$) and the solvent was evaporated under reduced pressure. The residue was purified by flash column chromatography on silica gel, eluting with isohexane/EtOAc (90:10), to give the title compound as a colorless solid (930 mg, 42%). $^1$H NMR (400 MHz, CDCl$_3$) δ 7.43–7.40 (2H, m), 7.33–7.29 (2H, m), 7.21–7.13 (3H, m), 6.68 (1H, td, J 0.6, 7.4 Hz), 6.78 (1H, d, J 8.2 Hz), 4.41 (2H, s), 3.95–3.86 (4H, m), 3.74 (3H, m), 3.41 (2H, s), 2.26 (2H, dd, J 3.2, 15.0 Hz), 1.98 (2H, dd, J 3.6, 13.0 Hz), and 1.68–1.53 (4H, m).

EXAMPLE 2

1-({[4-Oxo-1-phenylcyclohexyl]methoxy}methyl)-2-methoxybenzene

Prepared from 1-{[(1,4-dioxa-8-phenylspiro[4.5]decan-8-yl)methoxy]methyl}-2-methoxybenzene (Example 1) according to the method of Example 10. $^1$H NMR (400 MHz, CDCl$_3$) δ 7.50–7.47 (2H, m), 7.41–7.37 (2H, m), 7.30–7.15 (3H, m), 6.89 (1H, td, J 0.7, 27.4 Hz), 6.81 (1H, d, J 8.2 Hz), 4.44 (2H, s), 3.76 (3H, s), 3.46 (2H, s), 2.56–2.51 (2H, m), and 2.34–2.17 (6H, m).

EXAMPLE 3

1-{[(1,4-Dioxa-8-phenylspiro[4.5]decan-8-yl)methoxy]methyl}-2-(cyclopropoxy)-5-(trifluoromethoxy)benzene Prepared from 8-phenyl-1,4-dioxaspiro[4.5]decane-8-methanol (*J. Org. Chem.* 1974, 39, 2311–2313) and 2-(cyclopropyloxy)-5-(trifluoromethoxy)phenylmethyl methanesulfonate (Description 13) according to the method of Example 1. $^1$H NMR (400 MHz, CDCl$_3$) δ 7.42 (2H, dd, J 8.0, 1.0 Hz), 7.32 (2H, t, J 8.0 Hz), 7.23–7.18 (1H, m), 7.12–7.09 (1H, m), 7.03–7.01 (2H, m), 4.31 (2H, s), 3.97–3.88 (4H, m), 3.68–3.63 (1H, m), 3.40 (2H, s), 2.29 (2H, d, J 14.0 Hz), 1.94 (2H, dt, J$_d$ 4.0, J$_t$ 14.0 Hz), 1.67–1.53 (4H, m), and 0.77–0.66 (4H, m).

EXAMPLE 4

1-({[4-Oxo-1-phenylcyclohexyl]methoxy}methyl)-2-(cyclopropoxy)-5-(trifluoromethoxy)benzene Prepared from 1-{[(1,4-dioxa-8-phenylspiro[4.5]decan-8-yl)methoxy]methyl}-2-(cyclopropoxy)-5-(trifluoromethoxy)benzene (Example 3) according to the method of Example 10. $^1$H NMR (400 MHz, CDCl$_3$) δ 7.49 (2H, d, J 7.6 Hz), 7.41 (2H, t, J 7.6 Hz), 7.29 (1H, t, J 7.6 Hz), 7.13 (1H, d, J 8.8 Hz), 7.06–7.00 (2H, m), 4.34 (2H, s), 3.69–3.65 (1H, m), 3.45 (2H, s), 2.61–2.56 (2H, m), 2.38–2.32 (4H, m), 2.17–2.09 (2H, m), and 0.79–0.66 (4H, m).

EXAMPLE 5

(RS)-1-[(α-Methyl-8-phenyl-1,4-dioxaspiro[4.5]decane-8-methoxy)methyl]-3,5-bis(trifluoromethyl)benzene Sodium hydride (60% suspension in mineral oil, 700 mg, 30 mmol) was added in portions to a solution of (RS)-α-methyl-8-phenyl-1,4-dioxaspiro[4.5]decane-8-methanol (Description 22, 4 g, 15.3 mmol) in dimethylformamide (30 mL) and the mixture was stirred at room temperature for 1 hour. 1-(Bromomethyl)-3,5-bis(trifluoromethyl)benzene (2.8 mL, 15.3 mmol) was added and the mixture was stirred at 95° C. for 2.5 hours. The mixture was cooled, poured into water (500 mL) and extracted with diethyl ether (2×500 mL). The combined organic fractions were dried (MgSO$_4$) and the solvent was evaporated under reduced pressure. The residue was purified by flash column chromatography on silica gel, eluting with isohexane/EtOAc (90:10) to give the tide compound as a pale oil (4.1 g, 55%). $^1$H NMR (360 MHz, CDCl$_3$) δ 0.98 (3H, d, J 6.5 Hz), 1.48–1.65 (4H, m), 1.87–1.97 (2H, m), 2.24–2.28 (1H, m), 2.43–2.50 (1H, m), 3.43 (1H, q, J 6.1 Hz), 3.86–3.96 (4H, m), 4.33 (1H, d, J 12.6 Hz), 4.61 (1H, d, J 12.6 Hz), 7.19–7.41 (5H, m), 7.69 (2H, s), and 7.75 (1H, s).

EXAMPLE 6

(RS)-1-[(α-Methyl-4-oxo-1-phenylcyclohexanemethoxy)methyl]-3,5-bis(trifluoromethyl)benzene Prepared from (RS)-1-[(α-methyl-8-phenyl-1,4-dioxaspiro[4.5]decane-8-methoxy)methyl]-3,5-bis(trifluoromethyl)benzene (Example 5) according to the method of Example 10. $^1$H NMR (360 MHz, CDCl$_3$) δ 1.03 (3H, d, J 6.5 Hz), 1.98–2.15 (2H, m), 2.23–2.33 (4H, m), 2.53–2.58 (1H, m), 2.70–2.78 (1H m), 3.50 (1H, q, J 6.1 Hz), 4.34 (1H, d, J 12.6 Hz), 4.63 (1H, d, J 12.6 Hz), 7.28–7.49 (5H, m), 7.67 (2H, s), and 7.77 (1H, s).

EXAMPLE 7

(RS)-1-[(α-Ethenyl-8-phenyl-1,4-dioxaspiro[4.5]decane-8-methoxy)methyl]-3,5-bis(trifluoromethyl)benzene Prepared from (RS)-α-ethenyl-8-phenyl-1,4-dioxaspiro[4.5]decane-8-methanol (Description 23) and 1-(bromomethyl)-3,5-bis(trifluoromethyl)benzene according to the method of Example 5. $^1$H NMR (360 MHz, CDCl$_3$) δ 1.46–1.62 (4H, m), 1.76–1.90 (2H, m), 2.26–2.32 (1H, m), 2.45–2.54 (1H, m), 3.58 (1H, d, J 8.3 Hz), 3.85–3.95 (4H, m), 4.24 (1H, d, J 12.6 Hz), 4.53 (1H, d, J 12.6 Hz), 5.12–5.29 (2H, m), 5.40–5.50 (1H, m), 7.20–7.40 (5H, m), 7.61 (2H, s), and 7.73 (1H, s).

EXAMPLE 8

(RS)-1-[(α-Ethenyl-4-oxo-1-phenylcyclohexanemethoxy)methyl]-3,5-bis(trifluoromethyl)benzene Prepared from (RS)-1-[(α-ethenyl-8-phenyl-1,4-dioxaspiro[4.5]decane-8-methoxy)methyl]-3,5-bis(trifluoromethyl)benzene (Example 7) according to the method of Example 10. $^1$H NMR (360 MHz, CDCl$_3$) δ 1.92–2.04 (2H, m), 2.22–2.41 (4H, m), 2.58–2.65 (1H, m), 2.77–2.83 (1H, m), 3.63 (1H, d, J 8.4 Hz), 4.26 (2H, d, J 12.8 Hz), 4.56 (1H, d, j 12.8 Hz), 5.17 (1H, d, J 17.2 Hz), 5.29–5.34 (1H, m), 5.45–5.54 (1H, m), 7.29–7.49 (5H, m), 7.59 (2H, s), and 7.75 (1H, s).

EXAMPLE 9

(1,4-Dioxa-8-phenylspiro[4.5]decan-8-yl)methyl 3,5-Bis(trifluoromethyl)benzoate 3,5-Bis(trifluoromethyl)benzoyl chloride (115 μl, 0.64 mmol) was added to a solution of 8-phenyl-1,4-dioxaspiro[4.5]decane-8-methanol (*J. Org. Chem.* 1974, 39, 2311–2313, 150 mg, 0.6 mmol) in dichloromethane (3 mL) and the mixture was stirred at room temperature for 16 hours. Triethylamine (83 μl, 0.6 mmol) and 4-dimethylamino pyridine (1 crystal) were added and the mixture was stirred at room temperature for 1 hour. 3,5-Bis(trifluoromethyl)benzoyl chloride (57 μl, 0.32 mmol) was added and the mixture was stirred at room temperature for 1 hour. The mixture was diluted with water (10 mL) and extracted with dichloromethane (3×10 mL). The combined organic fractions were washed with brine, dried (MgSO$_4$) and the solvent was evaporated under reduced pressure. The residue was purified by flash column chromatography on silica gel, eluting with isohexane/EtOAc (5:1), to give the title compound as a colorless oil (231 mg, 78%) contaminated with about 10% of (4-oxo-1-phenylcyclohexyl}methyl 3,5-bis(trifluoromethyl)benzoate. $^1$H NMR (360 MHz, CDCl$_3$) δ 1.55–1.73 (5H, m), 1.97 (2H, dt, J 3.7, 13.7 Hz), 2.39 (2H, m), 3.89–3.98 (4H, m), 7.23–7.27 (1H, m), 7.35–7.7.39 (2H, m), 7.45–7.47 (2H, m), 8.02 (1H, s), and 8.31 (2H, s).

EXAMPLE 10

(4-Oxo-1-phenylcyclohexyl}methyl 3,5-Bis(trifluoromethyl)benzoate

Hydrochloric acid (2M, 2 mL, 4 mmol) was added to a solution of (1,4-dioxa-8-phenylspiro[4.5]decan-8-yl)methyl 3,5-bis(trifluoromethyl)benzoate (Example 9, 220 mg, 0.45 mmol) in acetone and the mixture was heated under reflux for 30 minutes. The mixture was cooled and the solvent was evaporated under reduced pressure. Aqueous sodium carbonate (saturated) was added and the mixture was extracted with ethyl acetate (3×20 mL). The combined organic fractions were washed with brine, dried (MgSO$_4$) and the solvent was evaporated under reduced pressure to give the title compound as a colorless solid (190 mg, 95%). $^1$H NMR (360 MHz, CDCl$_3$) δ 2.04–2.13 (2H, m), 2.37–2.42 (4H, m), 2.66–2.76 (2H, m), 4.37 (2H, s), 7.34 (1H, t, J 7.3 Hz), 7.46 (2H, t, J 7.7 Hz), 7.53–7.56 (2H, m), 8.04 (1H, s), and 8.32 (2H, s).

EXAMPLE 11

1-{1-[(1,4-Dioxa-8-phenylspiro[4.5]decan-8-yl)methoxy]ethenyl]}-3,5-bis(trifluoromethyl)benzene A solution of (1,4-dioxa-8-phenylspiro[4.5]decan-8-yl)methyl 3,5-bis(trifluoromethyl)benzoate (Example 9, 500 mg, 1.0 mmol) in toluene (10 mL) was degassed with a stream of nitrogen for 15 minutes. Dimethyltitanocene (0.2M in toluene, 10 mL, 2 mmol) was added and the mixture was degassed for a further 10 minutes. The mixture was heated at 90° C. in the dark for 12 hours, cooled, degassed for 10 minutes, and further dimethyltitanocene (0.2M in toluene, 5 mL, 1 mmol) was added. The mixture was heated at 90° C. in the dark for 15 hours, cooled, and sodium bicarbonate (3.1 g), methanol (50 mL) and water (1.9 mL) were added. The mixture was stirred at 40° C. for 2 hours, cooled, filtered through a bed of Celite™ and the solvent was evaporated under reduced pressure. The residue was diluted with water and extracted with ethyl acetate (2×50 mL). The combined organic fractions were washed with brine, dried (MgSO$_4$) and the solvent was evaporated under reduced pressure. The residue was purified by flash column chromatography on silica gel, eluting with CH$_2$Cl$_2$/isohexane (50:50), to give the title compound as a colorless gum (272 mg, 55%). $^1$H NMR (360 MHz, CDCl$_3$) δ 1.59–1.72 (4H, m), 1.96–2.04 (2H, m), 2.41(2H, br s, J 13.7 Hz), 3.77 (2H, s), 3.89–3.98 (4H, m), 4.27 (1H, d, J 3.3 Hz), 4.69 (1H, d, J 3.3 Hz), 7.23–7.27 (1H, m), 7.36–7.40 (2H, m), 7.47–7.50 (2H, m), 7.75 (1H, s), and 7.85 (2H, s).

EXAMPLE 12

(RS)-1-{1-[(1,4-Dioxa-8-phenylspiro[4.5]decan-8-yl)methoxy]ethyl]}-3,5-bis(trifluoromethyl)benzene Palladium on carbon (5%, 20 mg) was carefully added as an aqueous slurry to a solution of 1-{1-[(1,4-dioxa-8-phenylspiro[4.5]decan-8-yl)methoxy]ethenyl]}-3,5-bis(trifluoromethyl)benzene (Description34, 265 mg, 0.5 mmol) in ethanol (20 mL) and ethyl acetate (2 mL) and the mixture was shaken under an atmosphere of hydrogen (50 psi) for 3 hours. The mixture was filtered and the solvent was evaporated under reduced pressure to give the title compound as a colorless gum (225 mg, 85%). $^1$H NMR (360 MHz, CDCl$_3$) δ 1.30 (3H, d, J 6.5 Hz) 1.54–1.64 (4H, m), 1.86–1.97 (2H, m), 2.21–2.30 (2H, m), 3.19 (1H, d, J 8.7 Hz), 3.27 (1H, d, J 8.7 Hz), 3.87–3.97 (4H, m), 4.24 (1H, q, J 6.5 Hz), 7.19–7.37 (5H, m), 7.50 (2H, s), and 7.71 (1H, s).

EXAMPLE 13

(RS)-1-{1-[(4-Oxo-1-phenylcyclohexyl)methoxy]ethyl}-3,5-bis(trifluoromethyl)benzene Prepared from (RS)-1-{1-[(1,4-dioxa-8-phenylspiro[4.5]decan-8-yl)methoxy]ethyl]}-3,5-bis(trifluoromethyl)benzene (Example 12) according to the method of Example 10. $^1$H NMR (360 MHz, CDCl$_3$) δ 1.34 (3H, d, J 6.5 Hz) 2.03–2.15 (2H, m), 2.29–2.36 (4H, m), 2.51–2.60 (2H, m), 3.23 (1H, d, J 9.0 Hz), 3.31 (1H, d, J 9.0 Hz), 4.29 (1H, q, J 6.5 Hz), 7.27–7.31 (1H, m), 7.37–7.45 (4H, m), 7.51 (2H, s), and 7.73 (1H, s).

EXAMPLE 14

(RS)-β-[(1,4-Dioxa-8-phenylspiro[4.5]decan-8-yl)
methoxy]-3,5-bis(trifluoromethyl) benzeneethanol Borane tetrahydrofuran complex (1M in THF, 1.2 mL, 1.2 mmol) was added to a cooled (0 C) solution of 1-{1-[(1,4-dioxa-8-phenylspiro[4.5]decan-8-yl)methoxy]ethenyl]}-3,5-bis(trifluoromethyl)benzene (Description 34, 280 mg, 0.6 mmol) in tetrahydrofuran (5 mL), and the mixture was stirred at room temperature for 48 hours. Aqueous sodium hydroxide (4M, 2 mL) followed by aqueous hydrogen peroxide (30%, 2 mL) were added and the mixture was stirred at room temperature for 1 hour. Water (20 mL) was added and the mixture was extracted with ethyl acetate (2×30 mL). The combined organic fractions were washed with brine, dried (MgSO$_4$) and the solvent was evaporated under reduced pressure to give the crude title compound as a colorless gum (263 mg), which was used without further purification.

EXAMPLE 15

(RS)-β-[(4-Oxo-1-phenylcyclohexyl)methoxy]-3,5-bis(trifluoromethyl)benzeneethanol Prepared from (RS)-β-[(1,4-dioxa-8-phenylspiro[4.5]decan-8-yl)methoxy]-3,5-bis(trifluoromethyl)benzeneethanol (Example 14) according to the method of Example 10. $^1$H NMR (360 MHz, CDCl$_3$) δ 1.75–1.79 (1H, m), 2.01–2.09 (2H, m), 2.32–2.37 (4H, m), 2.56–2.69 (2H, m), 3.37 (1H, d, J 8.8 Hz), 3.41 (1H, d, J 8.8 Hz), 3.53–3.57 (2H, m), 4.30–4.33 (1H, m), 7.31–7.35 (1H, m), 7.41–7.48 (4H, m), 7.52 (2H, s), and 7.79 (1H, s).

EXAMPLE 16

3,5-Bis(trifluoromethyl)phenylmethyl 4-Oxo-1-phenylcyclohexanecarboxylate

Oxalyl chloride (4.8 mL, 55 mmol) was added to a solution of 4-oxo-1-phenylcyclohexanecarboxylic acid (Description 2, 6 g, 27 mmol) and dimethylformamide (1 drop) in toluene (150 mL) and the mixture was stirred at room temperature for 2 hours. The solvent was evaporated under reduced pressure and toluene was added. The solvent was evaporated under reduced pressure and the residue was dissolved in toluene (100 mL). 3,5-Bis(trifluoromethyl)benzenemethanol (6.25 g, 26 mmol) and 4-dimethylaminopyridine (3.62 g, 30 mmol) were added and the mixture was heated under reflux for 24 hours. The solvent was evaporated under reduced pressure and the residue was partitioned between ethyl acetate (100 mL) and hydrochloric acid (2M, 100 mL). The organic layer was dried (MgSO$_4$) and the solvent was evaporated under reduced pressure. The residue was purified by flash column chromatography on silica gel, eluting with isohexane/CH$_2$Cl$_2$ (60:40 increasing to 50:50) to give the title compound (4.5 g, 40%). $^1$H NMR (360 MHz, CDCl$_3$) δ 2.33–2.53 (6H, m), 2.72–2.77 (2H, m), 5.23 (2H, s), 7.28–7.41 (5H, m), 7.51 (2H, s), and 7.77 (1H, s).

EXAMPLE 17

4-Oxo-1-phenyl-N-{[3,5-bis(trifluoromethyl)phenyl]
methyl}cyclohexanecarboxamide Prepared from 4-oxo-1-phenylcyclohexanecarboxylic acid (Description 2) and 3,5-bis(trifluoromethyl)benzylamine according to the method of Example 177. m/z (ES$^+$) 444 (M+1).

EXAMPLE 18

(RS)-4-Oxo-1-phenol-N-{1-[3,5-bis(trifluoromethyl)
phenyl]ethyl}cyclohexanecarboxamide Bis(2-oxo-3-oxazolidinyl)phosphinic chloride (2.18 g, 8.6 mmol) was added to a cooled (0° C.) solution of 4-oxo-1-phenylcyclohexanecarboxylic acid (Description 2, 1.33 g, 6.1 mmol) and triethylamine (2.55 mL, 1.85 g, 18.3 mmol) in dichloromethane (20 mL) and the mixture was stirred at room temperature for 20 minutes (RS)-α-methyl-3,5-bis(trifluoromethyl)benzenemethanamine (Description 5, 1.57 g, 6.1 mmol) in dichloromethane (10 mL) was added and the mixture was stirred at room temperature for 26 hours. The solvent was evaporated under reduced pressure and hydrochloric acid (2M, 50 mL) was added. The mixture was extracted with ethyl acetate (3×50 mL) and the combined organic fractions were washed with hydrochloric acid (2M, 2×50 mL), aqueous sodium hydrogen carbonate (saturated, 2×50 mL) and brine (50 mL), dried (MgSO$_4$) and the solvent was evaporated under reduced pressure. The residue was purified by flash column chromatography on silica gel, eluting with isohexane/EtOAc (65:35), to give the title compound as a colorless foam (1.96 g, 70%). m/z (ES$^+$) 458 (M+1).

EXAMPLE 19

N-[(8-Phenyl-1,4-dioxaspiro[4.5]decan-8-yl)
methyl]-3,5-bis(trifluoromethyl)
benzenemethanamine Sodium triacetoxyborohydride (4.77 g, 22.5 mmol) was added to a solution of 8-phenyl-1,4-dioxaspiro[4.5]decane-8-carboxaldehyde (J. Med. Chem. 1975, 18, 593–599). (1.1 g, 4.5 mmol) and 3,5-bis(trifluoromethyl)benzenemethanamine (1.1 g, 4.5 mmol) in dichloroethane (50 mL) and the mixture was stirred at room temperature overnight. The mixture was poured into saturated aqueous sodium hydrogen carbonate (50 mL) and extracted with ethyl acetate (2×50 mL). The combined organic fractions were washed with brine (50 mL), dried (MgSO$_4$) and the solvent was evaporated under reduced pressure. The residue was purified by flash column chromatography on silica gel, eluting with isohexane/EtOAc (75:25), to give the title compound as a yellow oil (1.0 g, 47%). m/z (ES$^+$) 473 (M+1).

EXAMPLE 20

N-[(8-Phenyl-1,4-dioxaspiro[4.5]decan-8-yl)
methyl]-N-{[3,5-bis(trifluoromethyl)phenyl]
methyl}acetamide Acetic anhydride (2 mL) was added to a solution of N-[(8-phenyl-1,4-dioxaspiro[4.5]decan-8-yl)methyl]-3,5-bis(trifluoromethyl)benzenemethanamine (Example 19, 291 mg, 0.61 mmol) in pyridine (5 mL) and the mixture was stirred at room temperature for 1 hour. The solvent was evaporated under reduced pressure and the residue was dissolved in ethyl acetate (25 mL). The mixture was washed with aqueous copper sulphate (5%, 2×25 mL) and brine (25 mL), dried (MgSO$_4$) and the solvent was evaporated under reduced pressure to give the title compound (316 mg, 100%). m/z (ES$^+$) 516 (M+1).

EXAMPLE 21

N-[(4-Oxo-1-phenylcyclohexyl)methyl]-N-{[3,5-bis
(trifluoromethyl)phenyl]methyl}acetamide Prepared from N-[(8-phenyl-1,4-dioxaspiro[4.5]decan-8-yl)methyl]-N-{[3,5-bis(trifluoromethyl)phenyl]

methyl}acetamide (Example 20) according to the method of Example 10. $^1$H NMR (400 MHz, CDCl$_3$) mixture of two rotamers; major rotamer δ 7.76 (1H, s), 7.50–7.39 (5H, m), 7.20 (2H, s), 3.71 (2H, s), 3.56 (2H, s), 2.75–2.10 (8H, m), and 2.07 (3H, s); minor rotamer δ 7.72 (1H, s), 7.50–7.39 (5H, m), 7.31 (2H, s), 4.24 (2H, s), 3.43 (2H, s), 2.75–2.10 (8H, m), and 1.83 (3H, s).

EXAMPLE 22

(E)-4-Phenyl-4-{3-[3,5-bis(trifluoromethyl)phenyl] prop-1-enyl}cyclohexanone

Prepared from 8-phenyl-8-{3-[3,5-bis(trifluoromethyl) phenyl]prop-1-enyl}1,4-dioxaspiro[4.5]decane (Description 35) according to the method of Example 10. $^1$H NMR (400 MHz, CDCl$_3$) δ 7.71 (1H, s), 7.62 (2H, s), 7.46–7.28 (5H, m), 5.75 (1H, d, J 15.4 Hz), 5.49 (1H, dt, J$_t$ 15.4, J$_d$ 7.1 Hz), 3.49 (2H, d, J 7.1 Hz), 2.46 (6H, m), and 2.20 (2H, m).

EXAMPLE 23

(RS)-1-(8-Phenyl-1,4-dioxaspiro[4.5]decan-8-yl)-3-[3,5-bis(trifluoromethyl)phenyl]propan-2-yl Ethanoate and (RS)-1-(8-Phenyl-1,4-dioxaspiro[4.5]decan-8-yl)-3-[3,5-bis(trifluoromethyl)phenyl]propan-1-yl Ethanoate Borane-tetrahydrofuran complex (1.0M in tetrahydrofuran, 12 mL, 12 mmol) was added over 10 minutes to a solution of (E)-8-phenyl-8-{3-[3,5-bis (trifluoromethyl)phenyl]prop-1-enyl}1,4-dioxaspiro[4.5] decane (Description 35, 1.88 g, 4 mmol) and the mixture was stirred at room temperature for 4.5 hours. Water (2 mL) then aqueous sodium hydroxide (4M, 20 mL) and aqueous hydrogen peroxide (30 w/v %, 20 mL) were added and the mixture was stirred at room temperature for 30 minutes. Water (150 mL) was added and the mixture was extracted with ether (2×150 mL). The combined organic fractions were dried (MgSO$_4$) and the solvent was evaporated under reduced pressure. The residue was dissolved in pyridine (10 mL) and 4-dimethylaminopyridine (10 mg) and acetic anhydride (5 mL) were added. The mixture was stirred at room temperature for 4 hours, then water (150 mL) was added. The mixture was extracted with ethyl acetate (2×150 mL) and the combined organic fractions were washed with water (2×150 mL) and aqueous copper sulfate (5%, 2×100 mL), dried (MgSO$_4$) and the solvent was evaporated under reduced pressure. The residue was purified by flash column chromatography on silica gel, eluting with CH$_2$Cl$_2$/EtOAc (99:1 increasing to 95:5), to give:
(RS)-1-(8-phenyl-1,4-dioxaspiro[4.5]decan-8-yl)-3-[3,5-bis (trifluoromethyl)phenyl]propan-2-yl ethanoate (803 mg, 38%); $^1$H NMR (360 MHz, CDCl$_3$) δ 7.67 (1H, s), 7.36 (2H, s), 7.28–7.13 (5H, m), 4.87 (1H, m), 3.90 (4H, m), 2.68 (1H, dd, J 13.7, 6.7 Hz), 2.45 (1H, dd, J 13.7, 6.2 Hz), 2.23 (2H, m), 1.96 (1H, dd, J 14.7, 7.4 Hz), 1.80–1.45 (7H, m), and 1.72 (3H, m); and
(RS)-1-(8-phenyl-1,4-dioxaspiro[4.5]decan-8-yl)-3-[3,5-bis (trifluoromethyl)phenyl]propan-1-yl ethanoate (425 mg, 20%); $^1$H NMR (360 MHz, CDCl$_3$) δ 7.66 (1H, s), 7.44 (2H, s), 7.35–7.20 (5H, m), 4.98 (1H, dd, J 10.1, 2.1 Hz), 3.89 (4H, m), 2.51 (2H, m), 2.24 (2H, m), 2.06 (3H, s), and 1.95–1.40 (8H, m).

EXAMPLE 24

(RS)-1-(8-Phenyl-1,4-dioxaspiro[4.5]decan-8-yl)-3–3,5-bis(trifluoromethyl)phenyl]propan-2-ol Potassium carbonate (2.5 g) was added to a solution of (RS)-1-(8-phenyl-1,4-dioxaspiro[4.5]decan-8-yl)-3-[3,5-bis (trifluoromethyl)phenyl]propan-2-yl ethanoate (Example 23, 700 mg, 1.3 mmol) in methanol (20 mL) and water (3 mL) and the mixture was stirred at room temperature for 4 days. The methanol was evaporated under reduced pressure, water (50 mL) was added and the mixture was extracted with ethyl acetate (3×75 mL). The combined organic fractions were dried (MgSO$_4$) and the solvent was evaporated under reduced pressure to give the title compound as a colorless oil (626 mg, 97%). $^1$H NMR (400 MHz, CDCl$_3$) δ 7.68 (1H, s), 7.49 (2H, s), 7.34 (4H, m), 7.22 (1H, m), 3.91 (4H, m), 3.75 (1H, m), 2.66 (1H, dd, J 13.8, 8.2 Hz), 2.56 (1H, dd, J 13.8, 4.5 Hz), 2.33 (4H, m), and 1.89–1.49 (4H, m).

EXAMPLE 25

(RS)-4-{2-Hydroxy-3-[3,5-bis(trifluoromethyl) phenyl]propyl}-4-phenylcyclohexanone Prepared from (RS)-1-(8-phenyl-1,4-dioxaspiro[4.5] decan-8-yl)-3-[3,5-bis(trifluoromethyl)phenyl]propan-2-ol (Example 24) according to the method of Example 10. $^1$H NMR (400 MHz, CDCl$_3$) δ 7.70 (1H, s), 7.48 (2H, s), 7.42 (3H, m), 7.29 (2H, m), 3.72 (1H, m), 2.76–2.56 (4H, m), and 2.03–1.77 (4H, m).

EXAMPLE 26

Trans-(RS)-1-({4-[4-(4-Fluorophenyl)piperidin-1-yl]-α-methyl-1-phenylcyclohexanemethoxy}methyl)-3,5-bis (trifluoromethyl)benzene Prepared from (RS)-1-[(α-methyl-4-oxo-1-phenylcyclohexanemethoxy)methyl]-3,5-bis (trifluoromethyl)benzene (Example 6) and 4-(4-fluorophenyl)piperidine (Description 16) according to the method of Example 55. The product was purified by preparative thin layer chromatography on silica gel, eluting with CH$_2$Cl$_2$/MeOH/Et$_3$N(Aq.) (95:5:1). m/z (ES$^+$) 608 (M+1).

EXAMPLE 27

Cis-(RS)-1-({α-Ethenyl-4-[4-(4-fluorophenyl) piperidin-1-yl]-1-phenylcyclohexanemethoxy}methyl)-3,5-bis (trifuoromethyl)benzene and Trans-(RS)-1-({α-Ethenyl-4-[4-(4-fluorophenyl) piperidin-1-yl]-1-phenylcyclohexanemethoxy}methyl)-3,5-bis (trifluoromethyl)benzene Prepared from (RS)-1-[(α-ethenyl-4-oxo-1-phenylcyclohexanemethoxy)methyl]-3,5-bis (trifluoromethyl)benzene (Example 8) and 4-(4fluorophenyl)piperidine (Description 16) according to the method of Example 55. The product was purified by preparative thin layer chromatography on silica gel, eluting with CH$_2$Cl$_2$/MeOH/NH$_3$(Aq.) (95:5:1): trans-(RS)-1-({4-[4-(4-fluorophenyl)piperidin-1-yl]-α-ethenyl-1-phenylcyclohexanemethoxy}methyl)-3,5-bis (trifluoromethyl)benzene; $^1$H NMR (400 MHz, CDCl$_3$) δ 1.21–1.41 (2H, m), 1.50–1.90 (8H, m), 2.20–2.26 (2H, m), 2.35–2.45 (3H, m), 2.63–2.68 (1H, m), 2.90–2.93 (2H, m), 3.37 (1H, d, J 8.4 Hz), 4.23 (1H, d, J 12.6 Hz), 4.53 (1H, d, J 12.6 Hz), 5.17 (1H, d, J 18.8 Hz), 5.25–5.29 (1H, m), 5.42–5.51 (1H, m), 6.91–6.99 (2H, m), 7.10–7.42 (7H, m), 7.61 (2H, s), and 7.74 (1H, s); m/z (ES$^+$) 620 (M+1);

cis-(RS)-1-({4-[4-(4-fluorophenyl)piperidin-1-yl]-α-ethenyl-1-phenylcyclohexanemethoxy}methyl)-3,5-bis(trifluoromethyl)benzene; $^1$H NMR (400 MHz, CDCl$_3$) δ 1.44–1.68 (10H, m), 2.10–2.31 (4H, m), 2.42–2.50 (1H, m), 2.75–2.83 (1H, m), 3.05–3.15 (2H, m), 4.07–4.11 (1H, m), 4.38 (1H, d, J 13.2 Hz), 4.61 (1H, d, J 13.2 Hz), 5.18–5.28 (3H, m), 6.95–6.99 (2H, m), 7.16–7.44 (7H, m), 7.74 (2H, s), and 7.76 (1H, s); m/z (ES$^+$) 620 (M+1).

EXAMPLE 28

Trans-(RS)-4-[4-(4-Fluorophenyl)piperidin-1-yl]-1-phenyl-α-[3,5-bis(trifluoromethyl)phenylmethoxy]cyclohexaneethanol Ozone was bubbled through a stirred, cooled (–78° C.) solution of trans-(RS)-1-({4-[4-(4-fluorophenyl)piperidin-1-yl]-α-ethenyl-1-phenylcyclohexanemethoxy}methyl)-3,5-bis(trifluoromethyl)benzene (Example 27, 240 mg, 0.39 mmol) in dichloromethane (50 mL) and methanol (20 mL) for 5 minutes. Sodium borohydride (140 mg, 3.9 mmol) and methanol (50 mL) were added and the mixture was allowed to warm to room temperature. The solvent was evaporated under reduced pressure and ethyl acetate (50 mL) and aqueous sodium bicarbonate (saturated, 50 mL) were added. The layers were separated and the organic fraction was dried (MgSO$_4$) and the solvent was evaporated under reduced pressure. The residue was purified by flash column chromatography on silica gel, eluting with EtOAc/MeOH (90:10) to give the title compound (52 mg, 21%). m/z (ES$^+$) 624 (M+1).

EXAMPLE 29

Trans-(RS)-1-({α-Ethyl-4-[4-(4-fluorophenyl)piperidin-1-yl]-1-phenylcyclohexanemethoxy}methyl)-3,5-bis(trifluoromethyl)benzene A slurry of palladium on carbon (10%, 20 mg) in methanol (10 mL) was added to a solution of trans-(RS)-1-({α-ethenyl-4-[4-(4-fluorophenyl)piperidin-1-yl]-1-phenylcyclohexanemethoxy}methyl)-3,5-bis(trifluoromethyl)benzene (Example 27, 90 mg, 0.14 mmol) in methanol (15 mL) and the mixture was shaken under an atmosphere of hydrogen (50 psi) for 16 hours. The mixture was filtered through Celite™ and the solvent was evaporated under reduced pressure to give the tide compound as a colorless oil (88 mg, 98%). m/z (ES$^+$) 622 (M+1).

EXAMPLE 30

Trans-1-[({4-[4-(4-Fluorophenyl)piperidin-1-yl]-1-phenylcyclohexyl}methoxy)methyl]-2-methoxybenzene A solution of sodium cyanoborohydride (83 mg, 1.3 mmol) and zinc chloride (90 mg, 0.66 mmol) in methanol (10 mL) and added to a solution of 1-({[4-oxo-1-phenylcyclohexyl]methoxy}methyl)-2-methoxybenzene (Example 2, 400 mg, 1.3 mmol) and 4-(4-fluorophenyl)piperidine (Description 16, 256 mg, 1.43 mmol) in methanol (10 mL) and the mixture was stirred at room temperature for 24 hours. The mixture was poured into saturated aqueous sodium hydrogen carbonate (20 mL) and extracted with ethyl acetate (2×20 mL). The combined organic fractions were washed with brine (20 mL), dried (MgSO$_4$) and the solvent was evaporated under reduced pressure. The residue was purified by preparative thin layer chromatography on silica gel, eluting with CH$_2$Cl$_2$/MeOH/NH$_3$(Aq.) (98:2:0.2), to give the title compound. m/z (ES$^+$) 488 (M+1).

EXAMPLE 31

Trans-1-[({4-[4-(4-Fluorophenyl)piperidin-1-yl]-1-phenylcyclohexyl}methoxy)methyl]-2-(cyclopropoxy)-5-(trifluoromethoxy)benzene Prepared from 1-({[4-oxo-1-phenylcyclohexyl]methoxy}methyl)-2-(cyclopropoxy)-5-(trifluoromethoxy)benzene (Example 4) and 4-(4-fluorophenyl)piperidine (Description 16) according to the method of Example 55. m/z (ES$^+$) 598 (M+1).

EXAMPLE 32

Cis-(RS)-1-[1-({4-[4-(4-Fluorophenyl)piperidin-1-yl]-1-phenylcyclohexyl}methoxy)ethyl]-3,5-bis(trifluoromethyl)benzene and Trans-(RS)-1-[1-({4-[4-(4-Fluorophenyl)piperidin-1-yl]-1-phenylcyclohexyl}methoxy)ethyl]-3,5-bis(trifluoromethyl)benzene Prepared from (RS)-1-{1-[(4-oxo-1-phenylcyclohexyl)methoxy]ethyl}-3,5-bis(trifluoromethyl)benzene (Example 13) and 4-(4-fluorophenyl)piperidine (Description 16) according to the method of Example 55:

Cis-(RS)-1-[1-({4-[4-(4-fluorophenyl)piperidin-1-yl]-1-phenylcyclohexyl}methoxy)ethyl]-3,5-bis(trifluoromethyl)benzene; $^1$H NMR (400 MHz, CDCl$_3$) δ 1.32 (3H, d, J 6.5 Hz), 1.43–1.90 (10H, m), 2.20–2.40 (4H, m), 2.44–2.50 (2H, m), 3.07–3.09 (2H, m), 3.45 (1H, d, J 9.2 Hz), 3.58 (1H, d, J 9.2 Hz), 4.28 (1H, q, J 6.5 Hz), 6.95–7.00 (2H, m), 7.16–7.30 (4H, m), 7.31–7.38 (3H, m), 7.51 (2H, s), and 7.72 (1H, s); m/z (ES$^+$) 608 (M+1);

Trans-(RS)-1-[1-({4-[4-(4-fluorophenyl)piperidin-1-yl]-1-phenylcyclohexyl}methoxy)ethyl]-3,5-bis(trifluoromethyl)benzene; $^1$H NMR (360 MHz, CDCl$_3$) δ 1.32 (3H, d, J 6.5 Hz), 1.42–1.83 (10H, m), 2.10–2.20 (2H, m), 2.32–2.44 (4H, m), 2.90–3.00 (2H, m), 3.10 (1H, d, J 8.9 Hz), 3.16 (1H, d, J 8.9 Hz), 4.23 (1H, q, J 6.5 Hz), 6.93 (2H, t, J 8.6 Hz), 7.10–7.22 (2H, m), 7.25–7.36 (5H, m), 7.52 (2H, s), and 7.72 (1H, s); m/z (ES$^+$) 608 (M+1).

The following compounds were prepared as mixtures of cis- and trans-isomers from (RS)-1-{1-[(4-oxo-1-phenylcyclohexyl)methoxy]ethyl}-3,5-bis(trifluoromethyl)benzene (Example 13) according to the method of Example 55, substituting a suitable amine for piperidine.

Cis-(RS)- & Trans-(RS)-

| Ex. | —NR$_2$ | Formula | M.W. | m/z (ES$^+$) (M + 1). |
|---|---|---|---|---|
| 33 | —N(piperidine) | C28H33F6NO | 513 | 514 |
| 34 | —N(piperidine)-OH | C28H33F6NO2 | 529 | 530 |
| 35 | —N(piperidine)-CO$_2$Et | C31H37F6NO3 | 585 | 586 |
| 36 | —N(morpholine) | C27H31F6NO2 | 515 | 516 |
| 37 | —NH-CH$_2$-cyclopropyl | C27H31F6NO | 499 | 500 |
| 38 | —N(CH$_3$)$_2$ | C25H29F6NO | 473 | 474 |

The following trans-isomers were prepared from the compounds of Examples 33, 34, 37 and 38 by preparative thin layer chromatography on silica gel, eluting with CH$_2$Cl$_2$/MeOH/Et$_3$N (95:5:1).

Trans-(RS)-

| Ex. | —NR$_2$ | Formula | M.W. | m/z (ES$^+$) (M + 1). |
|---|---|---|---|---|
| 39 | —N(piperidine) | C28H33F6NO | 513 | 514 |
| 40 | —N(piperidine)-OH | C28H33F6NO2 | 529 | 530 |
| 41 | —NH-CH$_2$-cyclopropyl | C27H31F6NO | 499 | 500 |
| 42 | —N(CH$_3$)$_2$ | C25H29F6NO | 473 | 474 |

EXAMPLE 43

Cis-(RS)-β-[(4-Hydroxy-1-phenylcyclohexyl) methoxy]-3,5-bis(trifluoromethyl)benzeneethanol and Trans-(RS)-β-[(4-Hydroxy-1-phenylcyclohexyl) methoxy]-3,5-bis(trifluoromethyl)benzeneethanol Sodium borohydride (25 mg, 0.65 mmol) was added to a solution of (RS)-β-[(4-oxo-1-phenylcyclohexyl)methoxy]-3,5-bis(trifluoromethyl)benzeneethanol (Example 15, 75 mg, 0.16 mmol) in ethanol (5 mL) and the mixture was stirred at room temperature for 25 minutes. The solvent was evaporated under reduced pressure and ethyl acetate (50 mL) and hydrochloric acid (2M, 50 mL) were added. The layers were separated and the organic fraction was washed with brine (50 mL), dried (MgSO$_4$) and the solvent was evaporated under reduced pressure. The residue was purified by MPLC column chromatography on silica gel, eluting with CH$_2$Cl$_2$/EtOAc (80:20) to give:
trans-(RS)-β-[(4-hydroxy-1-phenylcyclohexyl)methoxy]-3,5-bis(trifluoromethyl)benzeneethanol (34 mg, 46%); $^1$H NMR (400 MHz, CD$_3$OD) δ 1.21–1.35 (2H, m), 1.62–1.82 (4H, m), 2.31–2.35 (1H, m), 2.47–2.51 (1H, m), 3.24 (1H, d, J 8.8 Hz), 3.36 (1H, d, J 8.8 Hz), 3.49–3.65 (3H, m), 4.31 (1H, t, J 5.4 Hz), 7.16–7.20 (1H, m), 7.28–7.32 (2H, m), 7.40–7.42 (2H, m), 7.64 (2H, s), and 7.80 (1H, s); and
cis-(RS)-β-[(4-hydroxy-1-phenylcyclohexyl)methoxy]-3,5-bis(trifluoromethyl)benzeneethanol (10 mg, 14%); $^1$H NMR (400 MHz, CD$_3$OD) δ 1.49–1.70 (4H, m), 1.80–1.85 (1H, m), 1.91–1.95 (1H, m), 2.07–2.14 (1H, m), 2.20–2.26 (1H, m), 3.37 (1H, d, J 8.8 Hz), 3.49–3.61 (3H, m), 3.69–3.71 (1H, m), 4.34 (1H, t, J 5.6 Hz), 7.15–7.19 (1H, m), 7.26–7.29 (2H, m), 7.38–7.40 (2H, m), 7.65 (2H, s), and 7.80 (1H, s).

EXAMPLE 44

Cis-(RS)-β-({4-[4-(4-Fluorophenyl)piperidin-1-yl]-1-phenylcyclohexyl}methoxy)-3,5-bis (trifluoromethyl)benzeneethanol and Trans-(RS)-β-({4-[4-(4-Fluorophenyl)piperidin-1-yl]-1-phenylcyclohexyl}methoxy)-3,5-bis (trifluoromethyl)benzeneethanol Prepared from (RS)-β-[(4-oxo-1-phenylcyclohexyl) methoxy]-3,5-bis(trifluoromethyl)benzeneethanol (Example 15) and 4-(4-fluorophenyl) piperidine (Description 16) according to the method of Example 55:

Cis-(RS)-β-({4-[4-(4-fluorophenyl)piperidin-1-yl]-1-phenylcyclohexyl}methoxy)-3,5-bis(trifluoromethyl)benzeneethanol; ¹H NMR (360 MHz, CDCl₃) δ 1.46–1.78 (6H, m), 1.80–2.06 (6H, m), 2.20–58 (6H, m), 3.04–3.30 (1H, m), 3.42–3.64 (3H, m), 3.68–3.76 (1H, m), 6.97 (2H, t, J 8.7 Hz), 7.17–7.21 (3H, m), 7.32–7.39 (4H, m), 7.57 (2H, s), and 7.79 (1H, s); m/z (ES⁺) 624 (M+1);

Trans-(RS)-β-({4-[4-(4-fluorophenyl)piperidin-1-yl]-1-phenylcyclohexyl}methoxy)-3,5-bis(trifluoromethyl)benzeneethanol; ¹H NMR (360 MHz, CDCl₃) δ 1.21–1.98 (13H, m), 2.21–2.58 (4H, m), 2.58–2.68 (1H, m), 2.97–3.12 (1H, m), 3.22 (1H, d, J 8.7 Hz), 3.28 (1H, d J 8.7 Hz), 3.51 (1H, m), 4.24–4.30 (1H, m), 6.95 (2H, t, J 8.7 Hz), 7.10–7.15 (2H, m), 7.25 (1H, s), 7.37–7.38 (4H, m), 7.53 (2H, s), and 7.78 (1H, s); m/z (ES⁺) 624 (M+1).

EXAMPLE 45

Cis- and Trans-(RS)-β-{[1-Phenyl-4-(phenylmethylamino)cyclohexyl]methoxy}-3,5-bis(trifluoromethyl)benzeneethanol Sodium triacetoxyborohydride (98 mg, 0.46 mmol) and glacial acetic acid (19 mg, 0.33 mmol) were added to a solution of (RS)-β-[(4-oxo-1-phenylcyclohexyl)methoxy]-3,5-bis(trifluoromethyl)benzeneethanol (Example 15, 156 mg, 0.33 mmol) and benzylamine (35 mg, 0.33 mmol) in dichloroethane (3 mL) and the mixture was stirred at room temperature overnight. Aqueous sodium hydrogen carbonate (saturated, 3 mL) and dichloromethane (5 mL) were added and the layers were separated. The organic fraction was poured onto an SCX cartridge (Varian Bond Elut™; 10 mL/500 mg) and the cartridge was washed with methanol (4×2 mL), then eluted with methanolic ammonia (2M, 2×2 mL). The solvent was evaporated under reduced pressure to give the title compound as a colorless solid (151 mg, 83%). ¹H NMR and analytical HPLC showed this to be a 1:1 mixture of trans:cis isomers. m/z (ES⁺) 552 (M+1).

The following compounds were prepared as mixtures of cis- and trans-isomers from (RS)-β-[(4-oxo-1-phenylcyclohexyl)methoxy]-3,5-bis(trifluoromethyl)benzeneethanol (Example 15) according to the method of Example 45, substituting a suitable amine for benzylamine.

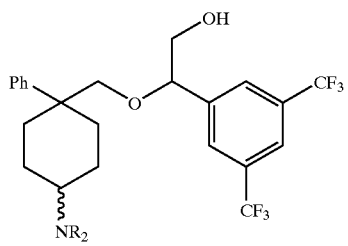

Cis-(RS)- & Trans-(RS)-

| Ex. | —NR₂ | Formula | M.W. | m/z (ES⁺) (M + 1). |
|---|---|---|---|---|
| 46 | —N(morpholine) | C27H31F6NO3 | 531 | 532 |
| 47 | —NH-CH₂-CH₂-Ph | C31H33F6NO2 | 565 | 566 |
| 48 | —NH-CH₂-CH₂-CH₂-Ph | C32H35F6NO2 | 579 | 580 |
| 49 | —NH-CH₂-cyclopropyl | C27H31F6NO2 | 515 | 516 |
| 50 | —NH-(CH₂)₄-Ph | C33H137F6NO2 | 593 | 594 |
| 51 | —NH-CH₂-(2-pyridyl) | C29H30F6N2O2 | 552 | 553 |
| 52 | —NH-CH₂-(3-pyridyl) | C29H30F6N2O2 | 552 | 553 |
| 53 | —NH-CH₂-(4-pyridyl) | C29H30F6N2O2 | 552 | 553 |
| 54 | —NH-CH₂-(2-furyl) | C28H29F6NO3 | 541 | 542 |

EXAMPLE 55

Cis- and Trans-(RS)-β-[(1-Phenyl-4-(piperidin-1-yl)cyclohexyl)methoxy]-3,5-bis(trifluoromethyl)benzeneethanol A mixture of sodium cyanoborohydride (6.8 mg, 0.11 mmol) and zinc chloride (7.3 mg, 0.05 mmol) in methanol (2 mL) was added to a solution of (RS)-β-[(4-oxo-1-phenylcyclohexyl)methoxy]-3,5-bis(trifluoromethyl)benzeneethanol (Example 15, 25 mg, 0.05 mmol) and piperidine (16 μl, 0.05 mmol) in methanol (2 mL) and the mixture was stirred at room temperature overnight. The solvent was evaporated under reduced pressure and aqueous sodium hydrogen carbonate (saturated, 3 mL) and dichloromethane (5 mL) were added. The layers were separated and the organic fraction was poured onto an SCX cartridge (Varian Bond Elut™; 10 mL/500 mg). The cartridge was washed with methanol (4×2 mL), then eluted with methanolic ammonia (2M, 2×2 mL). The solvent was evaporated under reduced pressure to give the title compound as a colorless solid (20 mg, 70%). $^1$H NMR and analytical HPLC showed this to be a 1:1 mixture of trans:cis isomers. m/z (ES$^+$) 530 (M+1).

The following compounds were prepared as mixtures of cis- and trans-isomers from (RS)-β-[(4-oxo-1-phenylcyclohexyl)methoxy]-3,5-bis(trifluoromethyl)benzeneethanol (Example 15) according to the method of Example 55, substituting a suitable amine for piperidine.

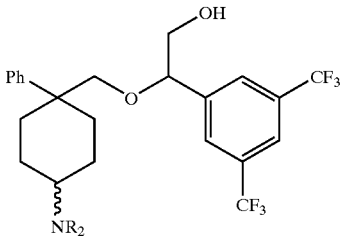

| Ex. | —NR$_2$ | Cis-(RS)- & Trans-(RS)- Formula | M.W. | m/z (ES$^+$) (M + 1). |
|---|---|---|---|---|
| 56 | —N(piperidinyl)-OH | C28H33F6NO3 | 545 | 546 |
| 57 | —N(piperidinyl)-CO$_2$Et | C31H37F6NO4 | 601 | 602 |
| 58 | —N(piperidinyl with 3-OH) | C28H33F6NO3 | 545 | 546 |
| 59 | —N(Me)CH$_2$Ph | C31H33F6NO2 | 565 | 566 |
| 60 | —N(Et)CH$_2$(4-pyridyl) | C31H34F6N2O2 | 580 | 581 |
| 61 | —N(piperazinyl)-(4-F-phenyl) | C33H35F7N2O2 | 624 | 625 |
| 62 | —N(pyrrolidinyl) | C27H31F6NO2 | 515 | 516 |
| 63 | —NH(iPr) | C24H27F6NO2 | 475 | 476 |
| 64 | —N(piperidinyl)-NMe$_2$ | C30H38F6N2O2 | 572 | 573 |
| 65 | —N(4-methylpiperidinyl) | C29H35F6NO2 | 543 | 544 |

-continued

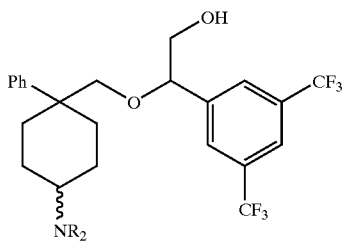

| Ex. | —NR₂ | Cis-(RS)- & Trans-(RS)- Formula | M.W. | m/z (ES⁺) (M + 1) |
|---|---|---|---|---|
| 66 | 2-methyl-1,2,3,4-tetrahydroisoquinoline | C32H33F6NO2 | 577 | 578 |
| 67 | 3-methylpiperidine (N-methyl) | C29H35F6NO2 | 543 | 544 |
| 68 | 4-(1,2-benzisothiazol-3-yl)piperazine (N-methyl) | C34H35F6N3O2S | 663 | 664 |
| 69 | azepane (N-methyl) | C29H35F6NO2 | 543 | 544 |
| 70 | 2-methylpyrrolidine (N-methyl) | C28H33F6NO2 | 529 | 530 |
| 71 | thiomorpholine (N-methyl) | C27H31F6NO2S | 547 | 548 |
| 72 | 2-methylpiperidine (N-methyl) | C29H35F6NO2 | 543 | 544 |
| 73 | 2-azabicyclo[2.2.1]heptane (N-methyl) | C29H33F6NO2 | 541 | 542 |
| 74 | —NH—CH2—CO2Me | C26H29F6NO4 | 533 | 534 |
| 75 | 4-cyclohexylpiperazine (N-methyl) | C33H42F6N2O2 | 612 | 613 |

-continued

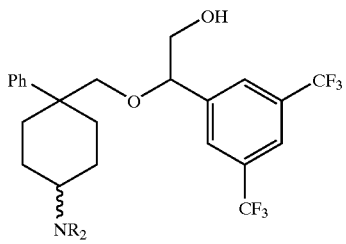

| Ex. | —NR₂ | Cis-(RS)- & Trans-(RS)- Formula | M.W. | m/z (ES⁺) (M + 1) |
|---|---|---|---|---|
| 76 | (3,3-dimethylpiperidin-1-yl) | C30H37F6NO2 | 557 | 558 |
| 77 | (3-hydroxymethylpiperidin-1-yl) | C29H35F6NO3 | 559 | 560 |
| 78 | (2,6-dimethylmorpholin-4-yl) | C29H35F6NO3 | 559 | 560 |
| 79 | (cyclopropylamino) | C26H29F6NO2 | 501 | 502 |

The following isomers were prepared from the compounds of Examples 55, 56 and 46 by MPLC chromatography on silica gel, eluting with CH₂Cl₂/MeOH/Et₃N (95:5:0.2).

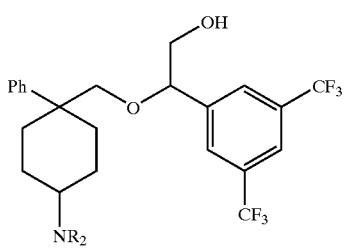

| Ex. | —NR₂ | Stereochemistry | Formula | M.W. | m/z (ES⁺) (M + 1) |
|---|---|---|---|---|---|
| 80 | piperidin-1-yl | Cis-(RS)- | C28H33F6NO2 | 529 | 530 |
| 81 | piperidin-1-yl | Trans-(RS)- | C28H33F6NO2 | 529 | 530 |

-continued

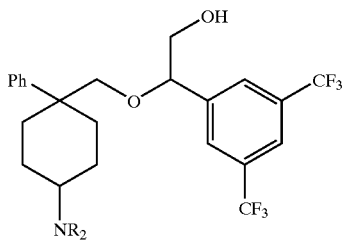

| Ex. | —NR₂ | Stereochemistry | Formula | M.W. | m/z (ES⁺) (M + 1) |
|---|---|---|---|---|---|
| 82 | —N⟨⟩—OH (piperidinyl-OH) | Cis-(RS)- | C28H33F6NO3 | 545 | 546 |
| 83 | —N⟨⟩—OH (piperidinyl-OH) | Trans-(RS)- | C28H33F6NO3 | 545 | 546 |
| 84 | —N⟨⟩O (morpholinyl) | Trans-(RS)- | C27H31F6NO3 | 531 | 532 |

EXAMPLE 85

Trans-(RS)-β-{[1-Phenyl-4-(phenylmethylamino) cyclohexyl]methoxy}-3,5-bis(trifluoromethyl) benzeneethanol Hydrochloride and Cis-(RS)-β-{[1-Phenyl-4-(phenylmethylamino) cyclohexyl]methoxy}-3,5-bis(trifluoromethyl) benzeneethanol Hydrochloride Benzylamine (1.07 mL, 9.8 mmol) was added to a mixture of (RS)-β-[(4-oxo-1-phenylcyclohexyl)methoxy]-3,5-bis (trifluoromethyl)benzeneethanol (Example 15, 1.5 g, 3.2 mmol) and dry alumina (1 g) in ethanol (35 mL) and the mixture was heated under reflux overnight. The mixture was cooled, filtered and cooled to −78° C. Sodium borohydride (1.23 g, 32.6 mmol) was added in portions over 2 hours, then aqueous sodium hydrogen carbonate (saturated, 20 mL) was added and the mixture was warmed to room temperature. The solvent was evaporated under reduced pressure and ethyl acetate (50 mL) and water (50 mL) were added. The layers were separated and the organic fraction was dried (MgSO₄) and the solvent was evaporated under reduced pressure. The residue was purified by flash column chromatography on silica gel, eluting with CH₂Cl₂/MeOH/Et₃N (98:2:1) to give a 5:1 mixture of trans:cis isomers (1.48 g), which was dissolved in ethyl acetate:hexane (3:1, 13 mL) and treated with ethereal hydrogen chloride (1M, 2.7 mL). The solid was collected and dried in vacuo to give: trans(RS)-β-{[1-phenyl-4-(phenylmethylamino)cyclohexyl] methoxy}-3,5-bis(trifluoromethyl)benzeneethanol hydrochloride (1.3 g, 72%). ¹H NMR (400 MHz, CD₃OD) δ 1.43–1.54 (2H, m), 1.73–1.82 (2H, m), 2.05–2.18 (2H, m), 2.50–2.58 (1H, m), 2.67–2.71 (1H, m), 2.82–2.88 (1H, m), 3.24 (1H, d, J 8.6 Hz), 3.37 (1H, d, J 8.6 Hz), 3.53–3.64 (2H, m), 4.13 (2H, s), 4.34 (1H, t, J 5.0 Hz), 7.20–7.24 (1H, m), 7.33–7.45 (9H, m), 7.65 (2H, s), and 7.81 (1H, s). m/z (ES⁺) 552 (M+1).

The mother liquors from the recrystallisation were collected and the solvent was evaporated under reduced pressure. The residue was crystallised from ethanol/water (70:30) and the solid was collected and dried in vacuo to give:

cis-(RS)-β-{[1-phenyl-4-(phenylmethylamino)cyclohexyl] methoxy}-3,5-bis(trifluoromethyl)benzeneethanol hydrochloride (50 mg, 3%). ¹H NMR (400 MHz, CD₃OD) δ 1.39–1.70 (4H, m), 1.81–1.90 (2H, m), 2.15–2.18 (1H, m), 2.36–2.39 (1H, m), 2.56–2.60 (1H, m), 3.48–3.61 (3H, m), 3.84 (1H, d, J 8.6 Hz), 3.77 (2H, s), 4.37 (1H, t, J 5.0 Hz), 7.18–7.48 (10H, m), 7.64 (2H, s), and 7.80 (1H, s). m/z (ES⁺) 552 (M+1).

EXAMPLE 86

Trans-(RS)-β-{[1-Phenyl-4-(phenylmethylamino) cyclohexyl]methoxy}-3,5-bis(trifluoromethyl) benzeneethanol A sample of trans-(RS)-β-{[1-phenyl-4-(phenylmethylamino)cyclohexyl]methoxy}-3,5-bis (trifluoromethyl)benzeneethanol hydrochloride (Example 85) was suspended in aqueous sodium hydrogen carbonate (saturated) and the mixture was extracted with ethyl acetate (3×). The combined organic fractions were dried (MgSO₄) and the solvent was evaporated under reduced pressure to give the title compound. ¹H NMR (400 MHz, CD₃OD) δ 1.17–1.29 (2H, m), 1.58–1.68 (2H, m), 1.83–1.89 (2H, m), 2.36–2.40 (1H, m), 2.53–2.65 (2H, m), 3.21 (1H, d, J 8.0 Hz), 3.33 (1H, d, J 8.0 Hz), 3.51 (1H, dd, J 10.8, 4.8 Hz), 3.61 (1H, dd, J 10.8, 5.6 Hz), 3.72 (2H, s), 4.30 (1H, t, J 5.2 Hz), 7.15–7.30 (8H, m), 7.40–7.42 (2H, m), 7.63 (2H, s), and 7.79 (1H, s).

EXAMPLE 87

Trans-(RS)-β-[(4-Amino-1-phenylcyclohexyl) methoxy]-3,5-bis(trifluoromethyl)benzeneethanol A slurry of palladium on carbon (5%, 20 mg) in methanol (10 mL) was added to a solution of trans-(RS)-β-{[1-phenyl-4-(phenylmethylamino)cyclohexyl]methoxy}-3,5-bis (trifluoromethyl)benzeneethanol hydrochloride (Example 85, 79 mg, 0.13 mmol) in ethanol (4 mL) and the mixture was shaken under an atmosphere of hydrogen (50 psi) for 16 hours. The mixture was filtered through Celite™, washing with ethanol, and the solvent was evaporated under reduced pressure. The residue was crystallised from Et₂O/EtOAc (2:1, 1 mL) and the solid was collected and dried in vacuo to give the title compound as a colorless solid (25 mg, 37%). m/z (ES⁺) 462 (M+1).

EXAMPLE 88

Cis-(RS)-β-[(4-Amino-1-phenylcyclohexyl)methoxy]-3,5-bis(trifluoromethyl)benzeneethanol Prepared from cis-(RS)-β-{[1-phenyl-4-(phenylmethylamino)cyclohexyl]methoxy}-3,5-bis(trifluoromethyl)benzeneethanol hydrochloride (Example 85) according to the method of Example 87. m/z (ES⁺) 462 (M+1).

EXAMPLE 89

Trans-(RS)-β-({4-[N-Methyl(phenylmethyl)amino]-1-phenylcyclohexyl}methoxy)-3,5-bis(trifluoromethyl)benzeneethanol Prepared from trans-(RS)-β-{[1-phenyl-4-(phenylmethylamino)cyclohexyl]methoxy}-3,5-bis(trifluoromethyl)benzeneethanol (Example 86) according to the method of Example 212. m/z (ES⁺) 566 (M+1).

EXAMPLE 90

Trans-(RS)-β-[(4-Methylamino-1-phenylcyclohexyl)methoxy]-3,5-bis(trifluoromethyl)benzeneethanol Prepared from trans-(RS)-β-({4-[N-methyl(phenylmethyl)amino]-1-phenylcyclohexyl}methoxy)-3,5-bis(trifluoromethyl)benzeneethanol (Example 89) according to the method of Example 87. m/z (ES⁺) 476 (M+1).

EXAMPLE 91

Trans-(RS)-β-[(4-{N-[2-(Dimethylamino)acetyl]amino}-1-phenylcyclohexyl)methoxy]-3,5-bis(trifluoromethyl)benzeneethanol Triethylamine (25 μL, 0.18 mmol) was added to a mixture of trans-(RS)-β-[(4-amino-1-phenylcyclohexyl)methoxy]-3,5-bis(trifluoromethyl)benzeneethanol (Example 87, 30 mg, 0.06 mmol), N,N-dimethylglycine (18 mg, 0.15 mmol), 1-hydroxybenzotriazole (8 mg, 0.06 mmol) and 1-(dimethylaminopropyl)-3-ethylcarbodiimide hydrochloride (15 mg, 0.08 mmol) in dry dichloromethane (3 mL) and the mixture was stirred at room temperature overnight. Aqueous sodium hydroxide (0.05M, 3 mL) and dichloromethane (5 mL) were added and the layers were separated. The aqueous layer was extracted with dichloromethane (3×3 mL) and the combined organic fractions were poured onto an SCX cartridge (Varian Bond Elut™; 10 mL/500 mg). The cartridge was washed with methanol (4×2 mL), then eluted with methanolic ammonia (2M, 2×2 mL) and the solvent was evaporated under reduced pressure. The residue was purified by column chromatography on a short column of silica gel, eluting with CH₂Cl₂/MeOH/Et₂N (100:0:1 increasing to 90:10:1), to give the title compound as a colorless solid (12 mg, 36%). m/z (ES⁺) 547 (M+1).

The following compounds were prepared from trans-(RS)-β-[(4-amino-1-phenylcyclohexyl)methoxy]-3,5-bis(trifluoromethyl)benzeneethanol (Example 87) or trans-(RS)-β-[(4-methylamino-1-phenylcyclohexyl)methoxy]-3,5-bis(trifluoromethyl)benzeneethanol (Example 90) according to the method of Example 91, substituting a suitable acid for N,N-dimethylglycine.

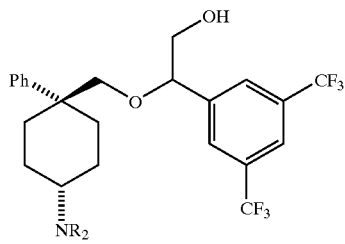

Trans-(RS)-

| Ex. | —NR₂ | Formula | M.W. | m/z (ES⁺) (M + 1) |
|---|---|---|---|---|
| 92 | ![structure] | C26H27F6N5O3 | 571 | 572 |
| 93 | ![structure] | C30H34F6N6O3 | 640 | 641 |
| 94 | ![structure] | C31H38F6N2O3 | 600 | 601 |

-continued
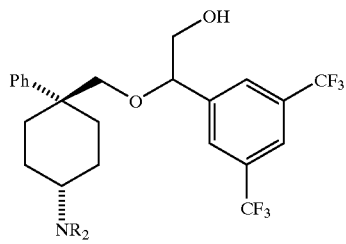
Trans-(RS)-
| Ex. | —NR₂ | Formula | M.W. | m/z (ES⁺) (M + 1) |
|---|---|---|---|---|
| 95 | —N(H)C(O)CH₂CH₂CH₂NMe₂ | C29H36F6N2O3 | 574 | 575 |
| 96 | —N(H)C(O)-(1H-imidazol-4-yl) | C27H27F6N3O3 | 555 | 556 |
| 97[1] | —N(H)C(O)CH₂-(pyrrolidin-1-yl) | C29H34F6N2O3 | 572 | 573 |
| 98 | —N(H)C(O)-(1-Boc-pyrrolidin-2-yl) | C33H40F6N2O5 | 658 | 659 |
| 99 | —N(H)C(O)CH₃ | C25H27F6NO3 | 503 | 504 |
| 100 | —N(Me)C(O)CH₂-(2H-tetrazol-5-yl) | C27H29F6N5O3 | 585 | 586 |
| 101 | —N(Me)C(O)CH₂CH₂-(piperidin-1-yl) | C32H40F6N2O3 | 614 | 615 |
| 102 | —N(Me)C(O)-(1H-imidazol-4-yl) | C28H29F6N3O3 | 569 | 570 |
| 103 | —N(H)C(O)CH₂-(pyrrolidin-1-yl) | C30H36F6N2O3 | 586 | 587 |
[1] 1-Pyrrolidineacetic acid: WO 9519344.

EXAMPLE 104

Trans-(RS,S)-N-(1-{[α-Hydroxymethyl-3,5-bis
(trifluoromethyl)phenylmethoxy]methyl}-1-
phenylcyclohexyl)-2-pyrrolidinecarboxamide Trifluoroacetic acid (4 drops) was added to a solution of trans-(RS,S)-1,1-dimethylethyl 2-[(1-{[α-hydroxymethyl-3,5-bis(trifluoromethyl)phenylmethoxy]methyl}-1-phenyl cyclohexylamino)carbonyl]-1-pyrrolidinecarboxylate (Example 98, 5 mg, 8 μmol) in dichloromethane (3 mL) and the mixture was stirred at room temperature for 5 minutes. Aqueous sodium hydrogen carbonate (saturated, 3 mL) and dichloromethane (5 mL) were added and the layers were separated. The aqueous layer was extracted with dichloromethane (3×3 mL) and the combined organic fractions were poured onto an SCX cartridge (Varian Bond Elut™; 10 mL/500 mg). The cartridge was washed with methanol (4×2 mL), then eluted with methanolic ammonia (2M, 2×2 mL) and the solvent was evaporated under reduced pressure to give the tide compound as a colorless solid (3 mg, 70%). m/z (ES$^+$) 559 (M+1).

EXAMPLE 105

Cis- and Trans-(RS)-β-[(1-Phenyl-4-
dimethylaminocyclohexyl)methoxy]-3,5-bis
(trifluoromethyl)benzeneethanol A slurry of palladium on carbon (5%, 20 mg) in methanol (10 mL) was added to a solution of (RS)-β-{[1-phenyl-4-(phenylmethylamino)cyclohexyl]methoxy}-3,5-bis (trifluoromethyl)benzeneethanol (1:1 mixture of cis- and trans-isomers, Example 45, 140 mg, 0,25 mmol) in methanol (4 mL) and the mixture was shaken under an atmosphere of hydrogen (50 psi) for 16 hours. The mixture was filtered through Celite™ and a slurry of palladium hydroxide (20%, 50 mg) in methanol (10 mL), aqueous formaldehyde (37%, 2 mL) and acetic acid (35 mg) were added. The mixture was shaken under an atmosphere of hydrogen (50 psi) for 16 hours, filtered through Celite™, washing with methanol, and the solvent was evaporated under reduced pressure to give the title compound as an oil (90 mg, 72%). $^1$H NMR and analytical HPLC showed this to be a 1:2 mixture of trans- and cis-isomers. m/z (ES$^+$) 490 (M+1).

EXAMPLE 106

Trans-(RS)-β-[(4-Cyclopropylmethylamino-1-
phenylcyclohexyl)methoxy]-3,5-bis(trifluoromethyl)
benzeneethanol Hydrochloride Prepared from trans-(RS)-β-[(4-amino-1-phenylcyclohexyl)methoxy]-3,5-bis(trifluoromethyl) benzeneethanol (Example 87) and cyclopropane carboxaldehyde according to the method of Example 55. m/z (ES$^+$) 516 (M+1).

EXAMPLE 107

1,2-Dihydro-5-{[N-(1-{[α-Hydroxymethyl-3,5-bis
(trifluoromethyl)phenylmethoxy]methyl}-1-
phenylcyclohex-4-yl)methylamino]methyl}-3H-1,2,
4-triazol-3-one Methyl 2-(2-chloro-1-iminoethyl)hydrazinecarboxylic acid (*J. Med. Chem.* 1996, 39, 2907–2914; 8 mg, 0.05 mmol) was added to a mixture of trans-(RS)-β-[(4-methylamino-1-phenylcyclohexyl)methoxy]-3,5-bis (trifluoromethyl)benzeneethanol Example 90, 23 mg, 0.04 mmol) and potassium carbonate (30 mg, 0.22 mmol) in dimethylformamide (1 mL) and the mixture was stirred at room temperature for 72 hours. The mixture was poured into water (10 mL) and extracted with ethyl acetate (2×20 mL). The combined organic fractions were dried (MgSO$_4$) and the solvent was evaporated under reduced pressure. The residue was dissolved in toluene (10 mL) and the mixture was stirred under reflux for 16 hours. The solvent was evaporated under reduced pressure and the residue was purified by flash column chromatography on silica gel, eluting with CH$_2$Cl$_2$/MeOH/Et$_3$N (100:0:1 increasing to 90:10:1), to give the title compound as a colorless oil (8 mg, 32%). m/z (ES$^+$) 573 (M+1).

EXAMPLE 108

Cis-(RS)-Methyl 1-1-{[α-Hydroxymethyl-3,5-bis
(trifluoromethyl)phenylmethoxy]methyl}-1-
phenylcyclohex-4-yl)piperidine-4-carboxylate and Trans-(RS)-Methyl 1-(1-{[α-Hydroxymethyl-3,5-bis
(trifluoromethyl)phenylmethoxy]methyl}-1-
phenylcyclohex-4-yl)piperidine-4-carboxylate A mixture of sodium cyanoborohydride (83 mg, 1.3 mmol) and zinc chloride (90 mg, 0.65 mmol) in methanol (2 mL) was added to a solution of (RS)-β-[(4-oxo-1-phenylcyclohexyl)methoxy]-3,5-bis(trifluoromethyl) benzeneethanol (Example 15, 300 mg, 0.65 mmol) and ethyl 4-piperidinecarboxylate (307 mg, 1.96 mmol) in methanol (30 mL) and the mixture was stirred at room temperature overnight. The solvent was evaporated under reduced pressure and aqueous sodium hydrogen carbonate (saturated, 3 mL) and dichloromethane (3 mL) were added. The layers were separated and the organic fraction was poured onto an SCX cartridge (Varian Bond Elut™; 10 mL/500 mg). The cartridge was washed with methanol (4×2 mL), then eluted with methanolic ammonia (2M, 2×2 mL) and the solvent was evaporated under reduced pressure. The residue was dissolved in methanol (5 mL) and sodium (catalytic) was added. The mixture was stirred at room temperature for 1 hour, then the solvent was evaporated under reduced pressure and ethyl acetate (50 mL) and water (50 mL) were added. The layers were separated and the organic fraction was dried (MgSO$_4$) and and the solvent was evaporated under reduced pressure. The residue was purified by MPLC chromatography on silica gel, eluting with CH$_2$Cl$_2$/MeOH/Et$_3$N (95:5:0.2) to give:
cis-(RS)-methyl 1-(1-{[α-hydroxymethyl-3,5-bis (trifluoromethyl)phenylmethoxy]methyl}-1-phenyl cyclohex-4-yl)piperidine-4-carboxylate as a colorless solid (130 mg, 33%); $^1$H NMR (360 MHz, CD$_3$OD) δ 1.45–1.94 (10H, m), 2.16–2.36 (6H, m), 2.90–2.95 (2H, m), 3.47 (3H, s), 3.42–3.53 (3H, m), 3.69 (1H, d, J 8.8 Hz), 4.30–4.32 (1H, m), 7.22–7.26 (1H, m), 7.32–7.39 (4H, m), 7.56 (2H, s), and 7.78 (1H, s); m/z (ES$^+$) 588 (M+1); and
trans-(RS)-methyl 1-(1-{[α-hydroxymethyl-3,5-bis (trifluoromethyl)phenylmethoxy]methyl}-1-phenyl cyclohex-4-yl)piperidine-4-carboxylate as a colorless solid (97 mg, 25%); $^1$H NMR (360 MHz, CD$_3$OD) δ 1.27–1.33 (2H, m), 1.60–1.68 (4H, m), 1.77–1.83 (4H, m) 2.12–216 (2H, m), 2.24–2.27 (1H, m), 2.39–2.44 (2H, m), 2.56–2.61 (1H, m), 2.78–2.82 (2H, m), 3.21 (1H, d, J 8.8 Hz), 3.33 (1H, d, J 8.8 Hz), 3.52 (1H, dd, J 11.5, 5.0 Hz), 3.61 (3H, s), 3.58–3.63 (1H, m), 4.31 (1H, t, J 5.8 Hz), 7.16–7.20 (1H, m), 7.28–7.33 (2H, m), 7.39–7.41 (2H, m), 7.64 (2H, s), and 7.80 (1H, s); m/z (ES$^+$) 588 (M+1).

EXAMPLE 109

Trans-(RS)-1-(1-{[α-Hydroxymethyl-3,5-bis
(trifluoromethyl)phenylmethoxy]methyl}-1-
phenylcyclohex-4-yl)piperidine-4-methanol A solution of diisobutylaluminium hydride (1.0M in toluene, 0.35 mL, 0.35 mmol) was added to a cooled (0° C.)

solution of trans-(RS)-methyl 1-(1-{[α-hydroxymethyl-3,5-bis(trifluoromethyl)phenylmethoxy]methyl}-1-phenyl cyclohex-4-yl)piperidine-4-carboxylate (Example 108, 50 mg, 0.08 mmol) in toluene (5 mL). The solution was allowed to warm to room temperature and stirred for 16 hours. Methanol (2 mL), then water (2 mL) and ethyl acetate (5 mL) were added and the layers were separated. The organic fraction was dried (MgSO$_4$) and the solvent was evaporated under reduced pressure to give the tide compound as a colorless solid (40 mg, 84%). m/z (ES$^+$) 560 (M+1).

EXAMPLE 110

Trans-(RS)-1-(1-{[α-Hydroxymethyl-3,5-bis(trifluoromethyl)phenylmethoxy]methyl}-1-phenylcyclohex-4-yl)piperidine-4-carboxylic Acid Potassium hydroxide (38 mg, 0.68 mmol) was added to a solution of trans-(RS)-methyl 1-(1-{[α-hydroxymethyl-3,5-bis(trifluoromethyl)phenylmethoxy]methyl}-1-phenyl cyclohex-4-yl)piperidine-4-carboxylate (Example 108, 50 mg, 0.08 mmol) in methanol (5 mL) and the mixture was stirred at room temperature for 16 hours. The solvent was evaporated under reduced pressure and water (2 mL) was added. The mixture was neutralised with hydrochloric acid (2M) and extracted with ethyl acetate (2×5 mL). The combined organic fractions were dried (MgSO$_4$) and the solvent was evaporated under reduced pressure to give the title compound as a colorless solid (28 mg, 56%). m/z (ES$^+$) 574 (M+1).

EXAMPLE 111

Trans-(RS)-1-(1-{[α-Hydroxymethyl-3,5-bis(trifluoromethyl)phenylmethoxy]methyl}-1-phenylcyclohex-4-yl)-α,α-dimethylpiperidine-4-methanol A solution of trans-(RS)-methyl 1-(1-{[α-hydroxymethyl-3,5-bis(trifluoromethyl)phenylmethoxy]methyl}-1-phenylcyclohex-4-yl)piperidine-4-carboxylate (Example 108, 21 mg, 0.04 mmol) in tetrahydrofuran (5 mL) was added dropwise to a cooled (0° C.) solution of methyl magnesium bromide (3.0M in ether, 0.05 mL, 0.15 mmol) in tetrahydrofuran (5 mL). The solution was allowed to warm to room temperature and stirred for 4 hours. Aqueous ammonium chloride (saturated, 7 mL), then water (7 mL) and ethyl acetate (10 mL) were added and the layers were separated. The organic fraction was dried (MgSO$_4$) and the solvent was evaporated under reduced pressure to give the title compound as a colorless solid (13 mg, 62%). m/z (ES$^+$) 588 (M+1).

EXAMPLE 112

Trans-(RS)-1-(1-{[α-Hydroxymethyl-3,5-bis(trifluoromethyl)phenylmethoxyl]methyl}-1-1-phenylcyclohex-4-yl)-N,N-dimethylpiperidine-4-carboxamide Prepared from trans-(RS)-1-(1-{[α-hydroxymethyl-3,5-bis(trifluoromethyl)phenylmethoxy]methyl}-1-phenyl cyclohex-4-yl)piperidine-4-carboxylic acid (Example 110) and dimethylamine hydrochloride according to the method of Example 182. m/z (ES$^+$) 601 (M+1).

EXAMPLE 113

(RS)-Methyl (1-(1-{[α-Hydroxymethyl-3,5-bis(trifluoromethyl)phenylmethoxy]methyl}-1-phenylcyclohex-4-ylidene)acetate Methyl (triphenylphosphoranylidene)acetate (261 mg, 0.78 mmol) was added to a solution of (RS)-β-[(4-oxo-1-phenylcyclohexyl)methoxy]-3,5-bis(trifluoromethyl) benzeneethanol (Example 15, 300 mg, 0.65 mmol) in dichloromethane (5 mL) and the mixture was stirred at 40° C. for 16 hours. Additional methyl (triphenylphosphoranylidene) acetate (217 mg, 0.65 mmol) was added and the mixture was stirred at 40° C. for 16 hours. The mixture was cooled and the solvent was evaporated under reduced pressure. The residue was purified by flash column chromatography on silica gel, eluting with isohexane/EtOAc (80:20), to give the title compound as a colorless oil (290 mg, 86%). $^1$H NMR (360 MHz, CDCl$_3$) δ 1.72–1.86 (3H, m), 2.18–2.29 (3H, m), 2.33–2.56 (2H, m), 3.21 (1H, d, J 8.8 Hz), 3.36 (1H, d, J 8.8 Hz), 3.49–3.52 (3H, m), 3.67 (3H, s), 4.25–4.32 (1H, m), 5.62 (1H, s), 7.26–7.27 (1H, m), 7.48–7.41 (4H, m), 7.53 (2H, s), and 7.77 (1H, s).

EXAMPLE 114

Cis- and Trans-(RS)-Methyl (1-(1-{[α-Hydroxymethyl-3,5-bis(trifluoromethyl)phenylmethoxy]methyl}-1-phenylcyclohex-4-yl) acetate A slurry of palladium on carbon (5%, 10 mg) in methanol (1 mL) was added to a solution of (RS)-methyl (1-(1-{[α-hydroxymethyl-3,5-bis(trifluoromethyl)phenylmethoxy] methyl}-1-phenyl cyclohex-4-ylidene)acetate (Example 113, 100 mg, 0.19 mmol) in methanol (5 mL) and the mixture was shaken under an atmosphere of hydrogen (40 psi) for 1 hour. The mixture was filtered through Celite™ and the solvent was evaporated under reduced pressure to give the title compound as an oil (87 mg, 87%). $^1$H NMR and analytical HPLC showed this to be a 1:1 mixture of trans- and cis-isomers. $^1$H NMR (400 MHz, CDCl$_3$) δ 1.04–1.35 (2H, m), 1.54–1.87 (6H, m), 2.07–2.50 (3H, m), 3.20–3.29 (2H, m), 3.43–3.51 (2H, m), 3.62 and 3.68 (Total 3H, each s), 4.24–4.32 (1H, m), 7.22–7.43 (5H, m), 7.54 (2H, m), and 7.78 (1H, m).

EXAMPLE 115

Cis-(RS)-1-[2-(1-(1-{[α-Hydroxymethyl-3,5-bis(trifluoromethyl)phenylmethoxy]methyl}-1-phenylcyclohex-4-yl)ethyl]pyrrolidine and Trans-(RS)-1-[2-(1-(1-{[α-Hydroxymethyl-3,5-bis(trifluoromethyl)phenylmethoxy]methyl}-1-phenylcyclohex-4-yl)ethyl]pyrrolidine A solution of diisobutylaluminium hydride (1.0M in hexane, 0.33 mL, 0.33 mmol) was added dropwise to a cooled (−78° C.) solution of (RS)-methyl (1-(1-{[α-hydroxymethyl-3,5-bis(trifluoromethyl)phenylmethoxy] methyl}-1-phenyl cyclohex-4-yl)acetate Example 114, 1:1 mixture of trans- and cis-isomers, 87 mg, 0.17 mmol) in isohexane/dichloromethane (3:1, 12 mL). The mixture was stirred at −78° C. for 4 hours, then methanol (2 mL), water (2 mL) and ethyl acetate (5 mL) were added. The layers were separated and the organic fraction was dried (MgSO$_4$) and the solvent was evaporated under reduced pressure. The residue was dissolved in methanol (3 mL) and pyrrolidine (0.14 mL, 1.7 mmol) and a mixture of sodium cyanoborohydride (42 mg, 0.66 mmol) and zinc chloride (46 mg, 0.33 mmol) in methanol (5 mL) were added. The mixture was stirred at room temperature overnight, and the solvent was evaporated under reduced pressure. Aqueous sodium hydrogen carbonate (saturated, 3 mL) and dichloromethane (3 mL) were added and the layers were separated. The organic fraction was poured onto an SCX cartridge (Varian Bond Elut™; 10 mL/500 mg) and the cartridge was washed with methanol (4×2 mL), then eluted with methanolic ammonia (2M, 2×2 mL). The solvent was evaporated under reduced pressure. The residue was purified by MPLC column chromatography on silica gel, eluting with $CH_2Cl_2/MeOH/Et_3N$ (98:2:0.2) to give:
cis-(RS)-1-[2-(1-(1-{[α-hydroxymethyl-3,5-bis(trifluoromethyl)phenylmethoxy]methyl}-1-phenylcyclohex-4-yl)ethyl]pyrrolidine (13 mg, 14%) as a colorless solid; $^1H$ NMR (360 MHz, $CD_3OD$) δ 1.23–1.45 (3H, m), 1.57–1.74 (6H, m), 2.00–2.08 (4H, m), 2.14–2.20 (1H, m), 2.31–2.35 (1H, m), 3.00–3.22 (6H, m), 3.44–3.60 (3H, m), 3.76 (1H, d, J 8.8 Hz), 4.37 (1H, t, J 5.6 Hz), 7.14–7.18 (1H, m), 7.24–7.28 (2H, m), 7.37–7.39 (2H, m), 7.65 (2H, s), and 7.81 (1H, s); m/z ($ES^+$) 544 (M+1); and
trans-(RS)-1-[2-(1-(1-{[α-hydroxymethyl-3,5-bis(trifluoromethyl)phenylmethoxy]methyl}-1-phenylcyclohex-4-yl)ethyl]pyrrolidine (10 mg, 11%) as a colorless solid; $^1H$ NMR (360 MHz, $CD_3OD$) δ 1.01–1.11 (2H, m), 1.46–1.50 (3H, m), 1.60–1.71 (4H, m), 2.01–2.09 (4H, m), 2.36–2.41 (1H, m), 2.51–2.56 (1H, m), 3.03–3.35 (7H, m), 3.35 (1H, d, J 8.8 Hz), 3.47 (1H, dd, J 10.8, 7.2 Hz), 3.51 (1H, dd, J 7.2, 4.3 Hz), 4.31 (1H, t, J 5.8 Hz), 7.16–7.20 (1H, m), 7.24–7.31 (2H, m), 7.37–7.40 (2H, m), 7.64 (2H, s), 7.80 (1H, s); m/z ($ES^+$) 544 (M+1).

EXAMPLE 116

Trans-(RS)-Methyl α-({4-[4-(4-Fluorophenyl)piperidin-1-yl]-1-phenylcyclohexyl}methoxy)-3,5-bis(trifluoromethyl)benzeneacetate Methyl α-diazo-3,5-bis(trifluoromethyl)benzeneacetate (WO 95/21819, 97 mg, 0.31 mmol) in dichloromethane (1 mL) was added over 15 minutes to a mixture of trans-4-[4-(4-fluorophenyl)piperidin-1-yl]-1-phenylcyclohexanemethanol (Description 21, 98 mg, 0.27 mmol) and rhodium acetate dimer (1 mg) in dichloromethane (1 mL) and the mixture was stirred at room temperature for 1 hour, then at 40° C. for 1 hour. The mixture was cooled and further methyl α-diazo-3,5-bis(trifluoromethyl)benzeneacetate (110 mg, 0.35 mmol) in dichloromethane (1 mL) was added. The mixture was stirred at room temperature for 0.5 hour, then at 40° C. for 0.5 hour. The mixture was cooled, divided into four portions and poured onto four SCX cartridges (Varian Bond Elut™; 10 mL/500 mg). Each cartridge was washed with methanol (4×1 mL), then eluted with methanolic ammonia (2M, 4×1 mL). The solvent was evaporated under reduced pressure and the residue was purified by flash column chromatography on silica gel, eluting with $CH_2Cl_2/MeOH/NH_3(Aq.)$ (97.5:2.5:0.25) to give the title compound (61 mg, 35%). m/z ($ES^+$) 652 (M+1).

EXAMPLE 117

Trans-3,5-Bis(trifluoromethyl)phenylmethyl 4-[4-(4-Fluorophenyl)piperidin-1-yl]-1-phenylcyclohexanecarboxylate Prepared from 3,5-bis(trifluoromethyl)phenylmethyl 4-oxo-1-phenylcyclohexanecarboxylate (Example 16) and 4-(4-fluorophenyl)piperidine (Description 16) according to the method of Example 55. The product was purified by preparative thin layer chromatography on silica gel, eluting with $CH_2Cl_2/MeOH/Et_3N(Aq.)$ (95:5:1). m/z ($ES^+$) 608 (M+1).

EXAMPLE 118

Trans-(RS)-1-[3,5-Bis(trifluoromethyl)phenyl]ethyl 4-[4-(4-Fluorophenyl)piperidin-1-yl]-1-phenylcyclohexanecarboxylate Oxalyl chloride (31 μl, 0.36 mmol) was added to a mixture of trans-4-[4-(4-fluorophenyl)piperidin-1-yl]-1-phenylcyclohexanecarboxylic acid hydrochloride (Description 20, 50 mg, 0.12 mmol) and dimethylformamide (1 drop) in dichloromethane (2 mL) and the mixture was stirred at room temperature for 2 hours. The solvent was evaporated under reduced pressure and the residue was dissolved in dichloroethane (2 mL). (RS)-α-Methyl-3,5-bis(trifluoromethyl)benzenemethanol (93 mg, 0.36 mmol), triethylamine (59 μl, 0.42 mmol) and 4-dimethylaminopyridine (1 mg) were added and the mixture was stirred at room temperature for 2 hours. The solvent was evaporated under reduced pressure and aqueous sodium carbonate (10%, 25 mL) and ethyl acetate (25 mL) were added. The layers were separated and the aqueous layer was extracted with ethyl acetate (25 mL). The combined organic fractions were washed with brine (25 mL), dried ($MgSO_4$) and the solvent was evaporated under reduced pressure. The residue was purified by flash column chromatography on silica gel, eluting with isohexane/EtOAc (90:10 increasing to 0:100), to give the title compound (39 mg, 52%). m/z ($ES^+$) 622 (M+1).

EXAMPLE 119

Trans-(RS)-2-Hydroxy-2-[3,5-bis(trifluoromethyl)phenyl]ethyl 4-[4-(4-Fluorophenyl)piperidin-1-yl]-1-phenylcyclohexanecarboxylate Oxalyl chloride (50 μl) was added to a mixture of trans-4-[4-(4-fluorophenyl)piperidin-1-yl]-1-phenylcyclohexanecarboxylic acid hydrochloride (Description 20, 63 mg, 0.15 mmol) and dimethylformamide (1 drop) in dichloromethane (2 mL) and the mixture was stirred at room temperature for 1 hour. The solvent was evaporated under reduced pressure and the residue was dissolved in dichloroethane (4 mL). Triethylamine (100 μl, 0.72 mmol), (RS)-1-[3,5-bis(trifluoromethyl)phenyl]-1,2-ethanediol (Description 3, 110 mg, 0.40 mmol) and 4-dimethylaminopyridine (1 mg) were added and the mixture was stirred at room temperature for 2 hours. Dichloromethane (20 mL) and aqueous sodium carbonate (10%, 20 mL) were added and the layers were separated. The aqueous fraction was extracted with dichloromethane (10 mL), then with ethyl acetate (10 mL). The combined organic layers were dried ($Na_2SO_4$) and the solvent was evaporated under reduced pressure. The residue was purified by flash column chromatography on silica gel, eluting with $CH_2Cl_2/MeOH/NH_3(Aq.)$ (95:5:0.5 increasing to 90:10:1) to give the title compound. m/z ($ES^+$) 638 (M+1).

EXAMPLE 120

Trans-(RS)-α-({[2-(Trimethylsilyl)ethoxy]methoxy}methyl)-[3,5-bis(trifluoromethy)phenyl]methyl 4-[4-(4-Fluorophenyl)piperidin-1-yl]-1-phenylcyclohexanecarboxylate Prepared from trans-4-[4-(4-fluorophenyl)piperidin-1-yl]-1-phenylcyclohexanecarboxylic acid hydrochloride (Description 20) and (RS)-1-[3,5-bis(trifluoromethyl)-α-{[2-(trimethylsilyl)ethoxy]methoxymethyl}benzenemethanol (Description 4) according to the method of Example 119. m/z ($ES^+$) 768 (M+1).

EXAMPLE 121

Trans-(RS)-α-(Hydroxymethyl)-[3,5-bis(trifluoromethyl)phenyl]methyl 4-[4-(4-Fluorophenyl)piperidin-1-yl]-1-(phenyl)cyclohexanecarboxylate Trifluoroacetic acid (0.5 mL) was added to a solution of trans-(RS)-α-({[2-(trimethylsilyl)ethoxy]methoxy}methyl)-[3,5-bis(trifluoromethyl)phenyl]methyl 4-[4-(4-fluorophenyl)piperidin-1-yl]-1-(phenyl)cyclohexanecarboxylate (Example 120, 37 mg, 48 μmmol) in dichloromethane (2 mL) and the mixture was stirred at room temperature for 1 hour. The solvent was evaporated under reduced pressure and the residue was purified by flash column chromatography on silica gel, eluting with $CH_2Cl_2$/MeOH/$NH_3$(Aq.) (95:5:0.5) to give the title compound (19 mg, 62%). m/z ($ES^+$) 638 (M+1).

EXAMPLE 122

Trans-(RS)-Methyl α-({4-[4-(Fluorophenyl)piperidin-1-yl]-1-phenylcyclohexyl}carbonyloxy)-3,5-bis(trifluoromethyl)benzeneacetate Methyl α-diazo-3,5-bis(trifluoromethyl)benzeneacetate (WO 95/21819, 200 mg, 0.64 mmol) in dichloromethane (2 mL) was added to a mixture of trans-4-[4-(4-fluorophenyl)piperidin-1-yl]-1-phenylcyclohexanecarboxylic acid hydrochloride (Description 20, 103 mg, 0.25 mmol) and rhodium acetate dimer (4 mg) in dichloromethane (2 mL) and the mixture was stirred at room temperature for 1 hour. Further methyl α-diazo-3,5-bis(trifluoromethyl)benzeneacetate (100 mg, 0.32 mmol) in dichloromethane (1 mL) was added and the mixture was stirred at room temperature for 1 hour. Further methyl α-diazo-3,5-bis(trifluoromethyl)benzeneacetate (50 mg, 0.16 mmol) in dichloromethane (1 mL) was added and the mixture was stirred at room temperature for 1 hour. The solvent was evaporated under reduced pressure and the residue was purified by flash column chromatography on silica gel, eluting with $CH_2Cl_2$/MeOH (97.5:2.5) to give the title compound (18 mg, 11%). m/z ($ES^+$) 666 (M+1).

EXAMPLE 123

Cis-{4-[4-(4-Fluorophenyl)piperidin-1-yl]-1-phenylcyclohexyl}methyl 3,5-Bis(trifluoromethyl)benzoate and Trans-{4-[4-(4-Fluorophenyl)piperidin-1-yl]-1-phenylcyclohexyl}methyl 3,5-Bis(trifluoromethyl)benzoate Sodium triacetoxyborohydride (420 mg, 2 mmol) was added to a mixture of (4-oxo-1-phenylcyclohexyl)methyl 3,5-bis(trifluoromethyl)benzoate (Example 10, 180 mg, 0.4 mmol), 4-(4-fluorophenyl)piperidine (Description 16, 72 mg, 0.4 mmol), and acetic acid (114 μl, 2 mmol) in 1,2-dichloroethane and the mixture was stirred at room temperature for 70 hours. Saturated aqueous sodium hydrogen carbonate (30 mL) was added and the mixture was extracted with ethyl acetate (3×20 mL). The combined organic fractions were washed with brine, dried ($MgSO_4$) and the solvent was evaporated under reduced pressure. The residue was purified by preparative thin layer chromatography, eluting with isohexane/EtOAc (50:50) to give:
cis-{4-[4-(4-fluorophenyl)piperidin-1-yl]-1-phenylcyclohexyl}methyl 3,5-bis(trifluoromethyl)benzoate (7.8 mg, 3%); $^1$H NMR (360 MHz, $CDCl_3$) δ 1.69–1.93 (10H, m), 2.24–2.60 (6H, m), 3.15 (2H, br d, J 10.6 Hz), 4.60 (2H, s), 6.98 (2H, t, J 8.7 Hz), 7.16–7.26 (3H, m), 7.34–7.38 (2H, m), 7.43–7.45 (2H, m), 8.00 (1H, s), and 8.23 (2H, s); m/z ($ES^+$) 608 (M+1); and trans-{4-[4-(4-fluorophenyl)piperidin-1-yl]-1-phenylcyclohexyl}methyl 3,5-bis(trifluoromethyl)benzoate (9 mg, 4%); $^1$H NMR (360 MHz, $CDCl_3$) δ 1.34–1.44 (2H, m), 1.60–178 (6H, m), 1.86–1.88 (2H, m), 2.14–2.20 (2H, m), 2.36–2.52 (2H, m), 2.58 (2H, br d, J 12.4 Hz), 2.95 (2H, d, J 11.4 Hz), 4.23 (2H, s), 6.94 (2H, t, J 8.7 Hz), 7.11–7.15 (2H, m), 7.22–7.26 (1H, m), 7.36–7.40 (2H, m), 7.45–7.47 (2H, m), 8.03 (1H, s), and 8.32 (2H, s); m/z ($ES^+$) 608 (M+1).

EXAMPLE 124

Cis-1-Phenyl-4-(4phenylpiperidin-1-yl)-N-{[3,5-bis(trifluoromethyl)phenyl]methyl}cyclohexanecarboxamide and Trans-1-Phenyl-4-(4-phenylpiperidin-1-yl)-N-{[3,5-bis(trifluoromethyl)phenyl]methyl}cyclohexanecarboxamide Prepared as a mixture of cis- and trans-isomers from 4-oxo-1-phenyl-N-{[3,5-bis(trifluoromethyl)phenyl]methyl}cyclohexanecarboxamide (Example 17) and 4-phenylpiperidine according to the method of Example 45. The isomers were separated by HPLC purification [YMC R&D CR; isohexane/EtOH (60:40)]:

cis-1-phenyl-4-(4-phenylpiperidin-1-yl)-N-{[3,5-bis(trifluoromethyl)phenyl]methyl}cyclohexanecarboxamide; $^1$H NMR (360 MHz, $CD_3OD$) δ 7.79 (1H, s) 7.69 (2H, s), 7.38–7.18 (10H, m), 4.47 (2H, s), 3.15 (2H, m), 3.05–2.40 (6H, m), 2.06 (2H, m), and 1.97–1.78 (9H, m); m/z ($ES^+$) 589 (M+1);

trans-1-phenyl-4-(4-phenylpiperidin-1-yl)-N-{[3,5-bis(trifluoromethyl)phenyl]methyl}cyclohexancarboxamide; $^1$H NMR (360 MHz, $CD_3OD$) δ 7.74 (1H, s) 7.55 (2H, s), 7.53–7.14 (10H, m), 4.39 (2H, s), 3.06 (2H, m), 2.80 (2H, m), 2.53 (2H, m), 2.32 (2H, m), and 1.99–1.29 (11H, m); m/z ($ES^+$) 589 (M+1).

The following compounds were prepared as mixtures of cis- and trans-isomers from (RS)-4-oxo-1-phenyl-N-{1-[3,5-bis(trifluoromethyl)phenyl]ethyl}cyclohexanecarboxamide (Example 18) according to the method of Example 55, substituting a suitable amine for piperidine.

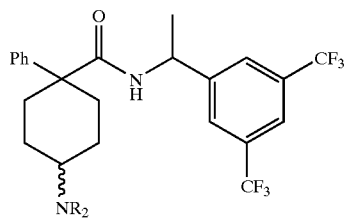
Cis-(RS) & Trans-(RS)
| Ex. | —NR₂ | Formula | M.W. | m/z (ES⁺) (M + 1) |
|---|---|---|---|---|
| 125 | —NH—CH₃ | C24H26F6N2O | 472 | 473 |
| 126 | pyrrolidinyl | C27H30F6N2O | 512 | 513 |
| 127 | 3-hydroxypiperidinyl | C28H32F6N2O2 | 542 | 543 |
| 128 | —NH—CH₂-cyclopropyl | C27H30F6N2O | 512 | 513 |
| 129 | 4-(CO₂Et)piperidinyl | C31H36F6N2O3 | 598 | 599 |
| 130 | 3-(OAc)piperidinyl | C30H34F6N2O3 | 584 | 585 |
| 131 | —N(Et)CH₂-(4-pyridyl) | C31H33F6N3O | 577 | 578 |
| 132 | morpholinyl | C27H30F6N2O2 | 528 | 529 |
| 133 | piperidinyl | C28H32F6N2O | 526 | 527 |
| 134 | 4-OH-4-(CH₂Ph)piperidinyl | C35H38F6N2O2 | 632 | 633 |

-continued
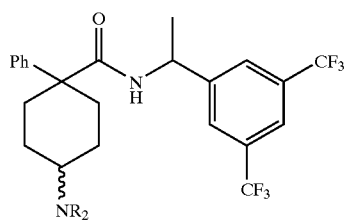
Cis-(RS) & Trans-(RS)
| Ex. | —NR₂ | Formula | M.W. | m/z (ES⁺) (M + 1) |
|---|---|---|---|---|
| 135 | piperidin-1-yl-piperidine | C33H41F6N3O | 609 | 610 |
| 136 | 4-formylpiperazin-1-yl | C28H31F6N3O2 | 555 | 556 |
| 137 | 4-(4-fluorophenyl)piperazin-1-yl | C33H34F7N3O | 621 | 622 |
| 138 | 4-(dimethylamino)piperidin-1-yl | C30H37F6N3O | 569 | 570 |
| 139 | 4-methylpiperidin-1-yl | C29H34F6N2O | 540 | 541 |
| 140 | 1,2,3,4-tetrahydroisoquinolin-2-yl | C32H32F6N2O | 574 | 575 |
| 141 | 3-methylpiperidin-1-yl | C29H34F6N2O | 540 | 541 |
| 142 | 4-(benzo[d]isothiazol-3-yl)piperazin-1-yl | C34H34F6N4OS | 660 | 661 |
| 143 | azepan-1-yl | C29H34F6N2O | 540 | 541 |

-continued
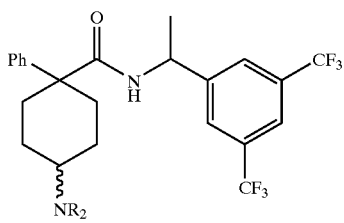
Cis-(RS) & Trans-(RS)
| Ex. | —NR₂ | Formula | M.W. | m/z (ES⁺) (M + 1). |
|---|---|---|---|---|
| 144 | | C28H32F6N2O | 526 | 527 |
| 145 | | C27H30F6N2OS | 544 | 545 |
| 146 | | C29H34F6N2O | 540 | 541 |
| 147 | | C26H28F6N2O3 | 530 | 531 |
| 148 | | C33H41F6N3O | 609 | 610 |
| 149 | | C30H36F6N2O | 554 | 555 |
| 150 | | C29H34F6N2O2 | 556 | 557 |
| 151 | | C29H34F6N2O2 | 556 | 557 |
| 152 | | C26H28F6N2O | 498 | 499 |

The following compounds were prepared from trans-4-[4-(4-fluorophenyl)piperidin-1-yl]-1-phenylcyclohexanecarboxylic acid hydrochloride (Description 20) according to the method of Example 177, substituting a suitable amine for (RS)-α-methyl-3,5-bis(trifluoromethyl)benzenemethanamine hydrochloride.

Trans-

| Ex. | —R | Formula | M.W. | m/z (ES+) (M + 1). |
|---|---|---|---|---|
| 153 | (2-OMe-phenyl)ethyl | C32H37FN2O2 | 500 | 501 |
| 154[1] | (2-OMe-phenyl)isopropyl (±) | C33H39FN2O2 | 514 | 515 |
| 155[2] | 1-(3,5-bis-CF3-phenyl)ethyl (±) | C35H37F7N2O | 634 | 635 |

[1](RS)-2-Methoxy-α-methylbenzenemethanamine Hydrochloride: Description 6.
[2](RS)-α-Ethyl-3,5-bis(trifluoromethyl)benzenemethanamine Hydrochloride: Description 7.

The following compounds were prepared from trans-4-[4-(4-fluorophenyl)piperidin-1-yl]-1-phenylcyclohexanecarboxylic acid hydrochloride (Description 20) according to the method of Example 158, substituting a suitable amine for 3-(methoxy)benzenemethanamine.

Trans-

| Ex. | —R | Formula | M.W. | m/z (ES+) (M + 1). |
|---|---|---|---|---|
| 156[1] | 2-(t-Bu)-3,5-bis-CF3-phenyl-dimethyl | C35H37F7N2O | 634 | 635 |
| 157[2] | CO2Me-CH(3,5-bis-CF3-phenyl) (±) | C35H35F7N2O3 | 664 | 665 |

[1]α,α-Dimethyl-3,5-bis(trifluoromethyl)benzenemethanamine Hydrochloride: Description 11.
[2](RS)-Methyl α-Amino-3,5-bis(trifluoromethyl)benzeneacetate Hydrochloride: Description 12.

EXAMPLE 158

Trans-4-[4-(4-Fluorophenyl)piperidin-1-yl]-N-{[3-(methoxy)phenyl]methyl}-1-phenylcyclohexanecarboxamide Bis(2-oxo-3-oxazolidinyl)phosphinic chloride (40 mg, 0.16 mmol) was added to a solution of trans-4-[4-(4fluorophenyl)piperdin-1-yl]-1-phenylcyclohexanecarboxylic acid hydrochloride (Description 20, 50 mg, 0.13 mmol) and triethylamine (91 μl, 0.65 mmol) in dichloromethane (5 mL) and the mixture was stirred at room temperature for 10 minutes. 3-(Methoxy)benzenemethanamine (18 μl, 0.14 mmol) was added and the mixture was stirred at room temperature overnight. Aqueous sodium carbonate (10%, 20 mL) and ethyl acetate (20 mL) were added and the layers were separated. The aqueous layer was extracted with ethyl acetate (2×20 mL) and the combined organic fractions were washed with brine (20 mL), dried (MgSO4) and the solvent was evaporated under reduced pressure. The residue was dissolved in methanol (0.5 mL) and poured onto an SCX cartridge (Varian Bond Elut™; 10 mL/500 Mg). The cartridge was washed with methanol (2×5 mL), then eluted with methanolic ammonia (2M, 5 mL). The solvent was evaporated under reduced pressure and the residue was purified by flash column chromatography on silica gel, eluting with CH₂Cl₂/MeOH/NH₃(Aq.) (90:4:0.4), to give the title compound (38 mg, 58%). m/z (ES⁺) 501 (M+1).

The following compounds were prepared from trans-4-[4-(4-flourophenyl)piperidin-1-yl]-1-phenylcyclohexanecarboxylic acid (Description 20) according to the method of Examples 158, substituting a suitable amine for 3-(methoxy)benzenemethanamine.

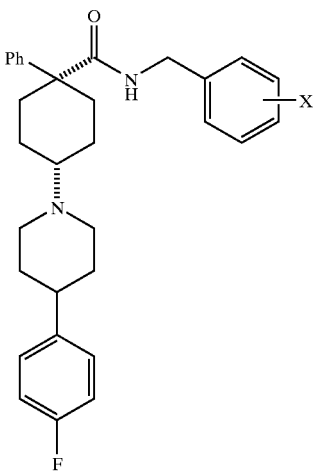

Trans-

| Ex. | —X— | Formula | M.W. | m/z (ES⁺) (M + 1). |
|---|---|---|---|---|
| 159 | 2-Cl | C31H34ClFN2O | 504 | 505 |
|     |      |              | 506 | 507 |
| 160 | 3-Cl | C31H34ClFN2O | 504 | 505 |
|     |      |              | 506 | 507 |
| 161 | 2,3-Cl₂ | C31H33Cl2FN2O | 538 | 539 |
|     |      |              | 540 | 541 |
|     |      |              | 542 | 543 |
| 162 | 2,4-Cl₂ | C31H33Cl2FN2O | 538 | 539 |
|     |      |              | 540 | 541 |
|     |      |              | 542 | 543 |
| 163 | 3-Cl-4-F | C31H33ClF2N2O | 522 | 523 |
|     |      |              | 524 | 525 |
| 164 | 2,4-F₂ | C31H33F3N2O | 506 | 507 |
| 165 | 2,6-F₂ | C31H33F3N2O | 506 | 507 |
| 166 | 3,5-F₂ | C31H33F3N2O | 506 | 507 |
| 167 | 2,3-Me₂ | C33H39FN2O | 498 | 499 |
| 168 | 2-CF₃ | C32H34F4N2O | 538 | 539 |
| 169 | 3-CF₃ | C32H34F4N2O | 538 | 539 |
| 170 | 4-CF₃ | C32H34F4N2O | 538 | 539 |
| 171 | 2,4-(OMe)₂ | C33H39FN2O3 | 530 | 531 |
| 172 | 3,5-(OMe)₂ | C33H39FN2O3 | 530 | 531 |
| 173 | 2,4,6-(OMe)₃ | C34H41FN2O4 | 560 | 561 |
| 174 | 2,6-(OMe)₂ | C33H39FN2O3 | 530 | 531 |
| 175 | 3,4-(OMe)₂ | C33H39FN2O3 | 530 | 531 |
| 176 | 2,5-(OMe)₂ | C33H39FN2O3 | 530 | 531 |

EXAMPLE 177

Trans-(RS)-4-[4-(4-Fluorophenyl)piperidin-1-yl]-N-{1-[3,5-bis(trifluoromethyl)phenyl]ethyl}-1-phenylcyclohexanecarboxamide Triethylamine (0.13 mL, 0.96 mmol) was added to a mixture of trans-4-[4-(4-fluorophenyl)piperidin-1-yl]-1-phenylcyclohexanecarboxylic acid hydrochloride (Description 20, 100 mg, 0.24 mmol), (RS)-α-methyl-3,5-bis(trifluoromethyl) benzenemethanamine hydrochloride (Description 5, 125 mg, 0.43 mmol) and 1-hydroxy benzotriazole (129 mg, 0.96 mmol) in dimethylformamide (10 mL) and the mixture was stirred at room temperature for 10 minutes. 1-(Dimethylaminopropyl)-3-ethylcarbodiimide hydrochloride (184 mg, 0.96 mmol) was added and the mixture was stirred at room temperature for 24 hours. The mixture was poured into water and extracted with ethyl acetate. The combined organic fractions were washed with aqueous sodium carbonate (saturated), dried (MgSO₄) and the solvent was evaporated under reduced pressure. The residue was purified by flash column chromatography on silica gel, eluting with CH₂Cl₂/MeOH/NH₃(Aq.) (90:10:1) to give the title compound as a colorless solid (145 mg, 97%). m/z (ES⁺) 621 (M+1).

EXAMPLE 178

Trans-(R)-4-[4(4-Fluorophenyl)piperidin-1-yl]-N-{1-[3,5-bis(trifluoromethyl)phenyl]ethyl}-1-phenylcyclohexanecarboxamide and Trans-(S)-4-[4-(4-Fluorophenyl)piperidin-1-yl]-N-{1-[3,5-bis(trifluoromethyl)phenyl]ethyl}-1-phenylcyclohexanecarboxamide The mixture of enantiomers of Example 177 was separated by chiral HPLC (Chirobiotic V; MeOH/Et₃N/AcOH; 100:0.1:0.1; 1 mL/min; 260 nm) to give:
trans-(R)-4-[4-(4-fluorophenyl)piperidin-1-yl]-N-{1-[3,5-bis(trifluoromethyl)phenyl]ethyl}-1-phenylcyclohexanecarboxamide; m/z (ES⁺) 621 (M+1); and trans-(S)-4-[4-(4-fluorophenyl)piperidin-1-yl]-N-{1-[3,5-bis(trifluoromethyl)phenyl]ethyl}-1-phenylcyclohexanecarboxamide; m/z (ES⁺) 621 (M+1).

EXAMPLE 179

Cis-(RS)-4-[4-(4-Fluorophenyl)piperidin-1-yl]-N-{1-[3,5-bis(trifluoromethyl)phenyl]ethyl}-1-phenylcyclohexanecarboxamide Hydrochloride Prepared from cis-4-[4-(4-fluorophenyl)piperidin-1-yl]-1-phenylcyclohexanecarboxylic acid (Description 19) and (RS)-α-methyl-3,5-bis(trifluoromethyl) benzenemethanamine hydrochloride (Description 5) according to the method of Example 177. m/z (ES⁺) 621 (M+1).

EXAMPLE 180

Trans-N-Methyl-1-phenyl-4-(4-phenylpiperidin-1-yl)-N-{[3,5-bis(trifluoromethyl)phenyl]methyl}cyclohexanecarboxamide Prepared from 1-phenyl-4-(4-phenylpiperidin-1-yl)-N-{[3,5-bis(trifluoromethyl)phenyl]methyl}cyclohexanecarboxamide (Mixture of cis- and trans-isomers, Example 124) according to the method of Example 156, followed by HPLC purification [YMC R&D CR; isohexane/EtOH (60:40)]. m/z (ES⁺) 603 (M+1).

EXAMPLE 181

Trans-(RS)-4-[4-(4-Fluorophenyl)piperidin-1-yl]-N-methyl-{1-[3,5-bis(trifluoromethyl)phenyl]ethyl}-1-phenylcyclohexanecarboxamide Sodium hydride (60% in mineral oil, 6.5 mg, 0.16 mmol) was added to a solution of trans-(RS)-4-[4-(4-fluorophenyl)piperidin-1-yl]-N-{1-[3,5-bis(trifluoromethyl)phenyl]

ethyl}-1-phenylcyclohexanecarboxamide (Example 177, 50 mg, 0.08 mmol) in dimethylformamide (5 mL) and the mixture was stirred at room temperature for 30 minutes. Iodomethane (15 μl, 0.24 mmol) was added and the mixture was stirred for 1 hour. Aqueous ammonium chloride (saturated) was added and the mixture was extracted with ethyl acetate. The combined organic fractions were washed with water, dried (MgSO$_4$) and the solvent was evaporated under reduced pressure. The residue was purified by preparative HPLC (Hichrom RPB; 250×20 mm; 65% MeCN in 0.1% TFA-H$_2$O; 20 mL/min; 210 nm) to give the title compound as a colorless solid, (20 mg, 39%). m/z (ES$^+$) 635 (M+1).

EXAMPLE 182

Trans-(RS)-4-[4-(4-Fluorophenyl)piperidin-1-yl]-1-phenyl-N-{2-hydroxy-1-[3,5-bis(trifluoromethyl)phenyl]ethyl}cyclohexanecarboxamide Lithium borohydride (12 mg, 0.55 mmol) was added to a solution of trans-(RS)-methyl α-({4-[4-(4-fluorophenyl)piperidin-1-yl]-1-phenylcyclohexyl}carbonylamino)-3,5-bis(trifluoromethyl)benzeneacetate (Example 157, 100 mg, 0.15 mmol) in tetrahydrofuran (4 mL) and the mixture was stirred at room temperature for 1.5 hours. Hydrochloric acid (2M, 1 mL) was added and the mixture was stirred at room temperature for 10 minutes. Potassium carbonate (500 mg) was added and the mixture was extracted with ethyl acetate (2×30 mL). The combined organic fractions were washed with aqueous sodium carbonate (10%, 20 mL) and brine (20 mL), dried (Na$_2$SO$_4$) and the solvent was evaporated under reduced pressure. The residue was purified by flash column chromatography on silica gel, eluting with CH$_2$Cl$_2$/MeOH/NH$_3$(Aq.) (95:5:0.5) to give the title compound (41 mg, 43%). m/z (ES$^+$) 637 (M+1).

EXAMPLE 183

Trans-(RS)-4-(1,4-Dioxa-8-azaspiro[4.5]decane-8-yl)-1-phenyl-N-{1-[3,5-bis(trifluoromethyl)phenyl]ethyl}cyclohexanecarboxamide Sodium triacetoxyborohydride (303 mg, 1.4 mmol) was added to a degassed solution of 4-oxo-1-phenylcyclohexanecarboxylic acid (Description 2, 260 mg, 1.2 mmol) and 1,4-dioxa-8-azaspiro[4.5]decane (0.15 mL, 168 mg, 1.2 mmol) in dichloroethane (5 mL) and the mixture was stirred at room temperature for 20 hours. The solvent was evaporated under reduced pressure and the residue was suspended in dichloromethane. Triethylamine (0.83 mL, 0.60 g, 6 mmol) and bis(2-oxo-3-oxazolidinyl)phosphonic chloride (460 mg, 1.8 mmol) were added. The mixture was stirred at room temperature for 10 minutes, then (RS)-α-methyl-3,5-bis(trifluoromethyl)benzenemethanamine hydrochloride(Description 5, 420 mg, 1.4 mmol) was added and the mixture was stirred at room temperature for 20 hours. Aqueous sodium carbonate was added and the mixture was extracted with dichloromethane. The combined organic fractions were dried (Na$_2$SO$_4$) and the solvent was evaporated under reduced pressure. The residue was purified by flash column chromatography on silica gel, eluting with CH$_2$Cl$_2$/MeOH/NH$_3$(Aq.) (96:4:0.4) to give the title compound (120 mg, 17%). m/z (ES$^+$) 585 (M+1).

EXAMPLE 184

Trans-(RS)-4-(4-Oxopiperidin-1-yl)-1-phenyl-N-{1-[3,5-bis(trifluoromethyl)phenyl]ethyl}cyclohexanecarboxamide Prepared from trans-4-(4-oxopiperidin-1-yl)-1-phenylcyclohexanecarboxylic acid hydrochloride (Description 24) and (RS)-α-methyl-3,5-bis(trifluoromethyl)benzenemethanamine hydrochloride (Description 5) according to the method of Example 158. m/z (ES$^+$) 541 (M+1).

EXAMPLE 185

Trans-(RS)-4-(4-Hydroxypiperidin-1-phenyl-N-{1-[3,5-bis(trifluoromethyl)phenyl]ethyl}cyclohexanecarboxamide Sodium borohydride (22.5 mg, 0.59 mmol) was added to a solution of trans-(RS)-4-(4-oxopiperidin-1-yl)-1-phenyl-N-{1-[3,5-bis(trifluoromethyl)phenyl]ethyl}cyclohexanecarboxamide (Example 184, 319 mg, 0.59 mmol) in ethanol (3 mL) and the mixture was stirred at room temperature for 1 hour. Aqueous ammonium chloride (saturated, 1 mL) and aqueous sodium carbonate (saturated, 10 mL) were added and the mixture was extracted with ethyl acetate (2×15 mL). The combined organic fractions were dried (Na$_2$SO$_4$) and the solvent was evaporated under reduced pressure. The residue was purified by flash column chromatography on silica gel, eluting with CH$_2$Cl$_2$/MeOH/NH$_3$(Aq.) (95:5:0.5 increasing to 85:15:1.5) to give the title compound (250 mg, 78%). m/z (ES$^+$) 543 (M+1).

EXAMPLE 186

Trans-(RS)-4-(But-3-enylamino)-1-phenyl-N-{1-[3,5-bis(trifluoromethyl)phenyl]ethyl}cyclohexanecarboxamide (N-Ethylethanaminato)trifluorosulfur (45 μl, 59 mg, 0.36 mmol) was added dropwise to a cooled (−60° C.) solution of trans-(RS)-4-(4-hydroxypiperidin-1-yl)-1-phenyl-N-{1-[3,5-bis(trifluoromethyl)phenyl]ethyl}cyclohexanecarboxamide (Example 185, 90 mg, 0.16 mmol) in ethyl acetate (5 mL) and the mixture was stirred at −60° C. for 1 hour, then allowed to warm to room temperature. Aqueous sodium hydrogen carbonate (saturated, 10 mL) was added and the mixture was extracted with ethyl acetate (2×20 mL). The combined organic fractions were washed with aqueous sodium carbonate (saturated, 20 mL) and brine (20 mL), dried (Na$_2$SO$_4$) and the solvent was evaporated under reduced pressure. The residue was purified by MPLC chromatography on silica gel, eluting with EtOAc/MeOH (85:15) to give the title compound (45 mg, 53%). m/z (ES$^+$) 513 (M+1).

EXAMPLE 187

Trans-(RS)-4-(4-Hydroxy-4-phenylpiperidin-1-yl)-1-phenyl-N-{1-[3,5-bis(trifluoromethyl)phenyl]ethyl}cyclohexanecarboxamide Phenylmagnesium bromide (1M in tetrahydrofuran, 0.3 mL, 0.3 mmol) was added dropwise to a cooled (0° C.) solution of trans-(RS)-4-(4-oxopiperidin-1-yl)-1-phenyl-N-{1-[3,5-bis(trifluoromethyl)phenyl]ethyl}cyclohexanecarboxamide (Example 184, 53 mg, 0.1 mmol) in tetrahydrofuran (2 mL) and the mixture was stirred at 0° C. for 10 minutes, then at room temperature for 1 hour. Aqueous ammonium chloride (saturated, 0.3 mL) and aqueous sodium carbonate (saturated, 10 mL) were added and the mixture was extracted with ethyl acetate (2×10 mL). The combined organic fractions were dried (Na$_2$SO$_4$) and the solvent was evaporated under reduced pressure. The residue was dissolved in methanol (1 mL) and poured onto an SCX cartridge (Varian Bond Elut™; 10 mL/500 mg). The cartridge was washed with methanol (4×1 mL), then eluted with methanolic ammonia (2M, 4×1 mL). The solvent was evaporated under reduced pressure to give the title compound (45 mg, 75%). m/z (ES$^+$) 619 (M+1).

The following compounds were prepared from trans-(RS)-4-(4-oxopiperidin-1-yl)-1-phenyl-N-{1-[3,5-bis(trifluoromethyl)phenyl]ethyl}cyclohexanecarboxamide (Example 184) according to the method of Example 187, substituting a suitable Grignard reagent for phenylmagnesium bromide.

| Ex. | —NR$_2$ | Formula | M.W. | m/z (ES$^+$) (M + 1). |
|---|---|---|---|---|
| 188 | (4-methyl-4-hydroxypiperidinyl) | C29H34F6N2O2 | 556 | 557 |
| 189 | (4-ethynyl-4-hydroxypiperidinyl) | C30H32F6N2O2 | 566 | 567 |
| 190 | (4-phenyl-4-hydroxypiperidinyl) | C35H38F6N2O2 | 632 | 633 |
| 191 | (4-allyl-4-hydroxypiperidinyl) | C31H36F6N2O2 | 582 | 583 |
| 192 | (4-phenylethynyl-4-hydroxypiperidinyl) | C36H36F6N2O2 | 642 | 643 |

EXAMPLE 193

Trans-(RS)-4-(1,2,3,6-Tetrahydro-4-phenylpyridin-1-yl)-1-phenyl-N-{1-[3,5-bis(trifluoromethyl)phenyl]ethyl}cyclohexanecarboxamide p-Toluenesulfonic acid hydrate (10 mg, 0.05 mmol) was added to a solution of trans-(RS)-4-(4-hydroxy-4-phenylpiperidin-1-yl)-1-phenyl-N-{1-[3,5-bis(trifluoromethyl)phenyl]ethyl}cyclohexanecarboxamide (Example 187, 26 mg, 0.04 mmol) in toluene (8 mL) and the mixture was heated under reflux for 8 hours. The mixture was cooled and aqueous sodium carbonate (saturated, 20 mL) was added. The mixture was extracted with ethyl acetate (2×20 mL) and the combined organic fractions were dried (Na$_2$SO$_4$) and the solvent was evaporated under reduced pressure. The residue was dissolved in methanol (1 mL) and poured onto an SCX cartridge (Varian Bond Elut™; 10 mL/500 mg). The cartridge was washed with methanol (4×1 mL), then eluted with methanolic ammonia (2M, 4×1 mL). The solvent was evaporated under reduced pressure to give the title compound (24 mg, 94%). m/z (ES$^+$) 601 (M+1).

EXAMPLE 194

Trans-(RS)-4-(1,2,3,6-Tetrahydro-4-methylpyridin-1-yl)-1-phenyl-N-{1-[3,5-bis(trifluoromethyl)phenyl]ethyl}cyclohexanecarboxamide Prepared from trans-(RS)-4-(4-hydroxy-4-methylpiperidin-1-yl)-1-phenyl-N-{1-[3,5-bis(trifluoromethyl)phenyl]ethyl}cyclohexanecarboxamide (Example 188) according to the method of Example 193. m/z (ES$^+$) 539 (M+1).

EXAMPLE 195

Trans-(RS)-4-(4-Hydroxy-4-phenylethyl)piperidin-1-yl)-phenyl-N-{1-[3,5-bis(trifluoromethyl)phenyl]ethyl}cyclohexanecarboxamide Palladium on carbon (5%, 5 mg) was added to a solution of trans-(RS)-4-(4-hydroxy-4-(phenylethynyl)piperidin-1-yl)-1-phenyl-N-{1-[3,5-bis(trifluoromethyl)phenyl]ethyl}cyclohexanecarboxamide (Example 192, 23 mg, 0.036 mmol) in ethanol (10 mL) and hydrochloric acid (2M, 1 mL) and the mixture was shaken under an atmosphere of hydrogen (50 psi) for 24 hours. The mixture was filtered through Celite™ and the solvent was evaporated under reduced pressure. Ethyl acetate (10 mL) and aqueous sodium carbonate (10%, 10 mL) were added and the layers were separated. The aqueous fraction was extracted with ethyl acetate (10 mL) and the combined organic fractions were dried (Na$_2$SO$_4$) and the solvent was evaporated under reduced pressure. The residue was dissolved in methanol (1 mL) and poured onto an SCX cartridge (Varian Bond Elut™; 10 mL/500 mg). The cartridge was washed with methanol (4×1 mL), then eluted with methanolic ammonia (2M, 4×1 mL). The solvent was evaporated under reduced pressure to give the tide compound (20 mg, 86%). m/z (ES$^+$) 647 (M+1).

The following compounds were prepared from trans-(RS)-4-(4-oxopiperidin-1-yl)-1-phenyl-N-{1–3,5-bis(trifluoromethyl)phenyl]ethyl}cyclohexanecarboxamide (Example 184) according to the method of Example 55, substituting a suitable amine for piperidine.

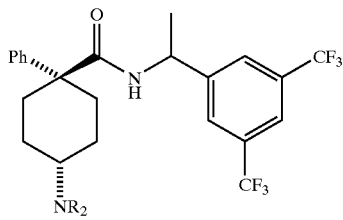

Trans-(RS)

| Ex. | —NR₂ | Formula | M.W. | m/z (ES⁺) (M + 1) |
|---|---|---|---|---|
| 196 | piperidine-N-piperidine-NMe₂ | C35H46F6N4O | 652 | 653 |
| 197 | piperidine-N-piperidine-Me | C34H43F6N3O | 623 | 624 |
| 198 | piperidine-tetrahydroisoquinoline | C37H41F6N3O | 657 | 658 |
| 199 | piperidine-N-piperidine(3-Me) | C34H43F6N3O | 623 | 624 |
| 200 | piperidine-piperazine-benzisothiazole | C39H43F6N5OS | 743 | 744 |
| 201 | piperidine-azepane | C34H43F6N3O | 623 | 624 |
| 202 | piperidine-(2-methyl)pyrrolidine | C33H41F6N3O | 609 | 610 |
| 203 | piperidine-thiomorpholine | C32H39F6N3OS | 627 | 628 |
| 204 | piperidine-azabicyclic | C34H41F6N3O | 621 | 622 |
| 205 | piperidine-NH-CH2-CO2Me | C31H37F6N3O3 | 613 | 614 |
| 206 | piperidine-piperazine-cyclohexyl | C38H50F6N4O | 692 | 693 |

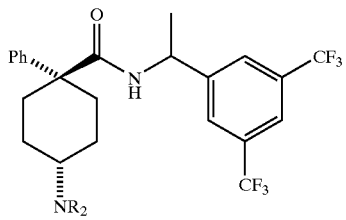

Trans-(RS)

| Ex. | —NR₂ | Formula | M.W. | m/z (ES⁺) (M + 1). |
|---|---|---|---|---|
| 207 | (piperidine-piperidine with gem-dimethyl) | C35H45F6N3O | 637 | 638 |
| 208 | (piperidine-piperidine with CH2OH) | C34H43F6N3O2 | 639 | 640 |
| 209 | (piperidine-dimethylmorpholine) | C34H43F6N3O2 | 639 | 640 |
| 210 | (piperidine-NH-cyclopropyl) | C31H37F6N3O | 581 | 582 |

EXAMPLE 211

Cis-(RS)-4-[(Phenylmethyl)amino]-N-{1-[3,5-bis(trifluoromethyl)phenyl]ethyl}-1-phenylcyclohexanecarboxamide and Trans-(RS)-4-[(Phenylmethyl)amino]-N-{1-[3,5-bis(trifluoromethyl)phenyl]ethyl}-1-phenylcyclohexanecarboxamide Prepared from (RS)-4-oxo-1-phenyl-N-{1-[3,5-bis(trifluoromethyl)phenyl]ethyl}cyclohexanecarboxamide (Example 18) and benzylamine according to the method of Example 45:
Cis-(RS)-4-[(phenylmethyl)amino]-N-{1-[3,5-bis(trifluoromethyl)phenyl]ethyl}-1-phenylcyclohexanecarboxamide; ¹H NMR (400 MHz, CDCl₃) δ 7.70 (1H, s), 7.46 (2H, s), 7.33–7.24 (10H, m), 5.09 (1H, q, J 7.0 Hz), 3.83 (2H, s), 2.58–2.55 (2H, m), 2.43 (1H, br d, J 15.2 Hz), 2.04 (1H, br d, J 11.4 Hz), 1.95–1.87 (2H, m), 1.64–1.42 (3H, m), and 1.37 (3H, d, J 7.0 Hz); m/z (ES⁺) 549 (M+1);
Trans-(RS)-4-[(phenylmethyl)amino]-N-{1-[3,5-bis(trifluoromethyl)phenyl]ethyl}-1-phenylcyclohexanecarboxamide; ¹H NMR (400 MHz, CDCl₃) δ 7.70 (s, 1H), 7.50–7.42 (6H, m), 7.34–7.21 (6H, m), 5.00 (1H, q, J 7.0 Hz), 3.75 (2H, s), 2.72–2.67 (1H, m), 2.48 (1H, br d, J 14.3 Hz, 2.37 (1H, br d, J 14.2 Hz), 2.17–2.06 (2H, m), 1.92–1.88 (2H, m), 1.39–1.16 (2H, m), and 1.27 (3H, d, J 7.0 Hz); m/z (ES⁺) 549 (M+1).

EXAMPLE 212

Trans-(RS)-4-[N-Methyl(phenylmethyl)amino]-N-{1-[3,5-bis(trifluoromethyl)phenyl]ethyl}-1-phenylcyclohexanecarboxamide Sodium cyanoborohydride (275 mg, 4.38 mmol) was added to a solution of trans-(RS)-4-[(phenylmethyl)amino]-N-{1-[3,5-bis(trifluoromethyl)phenyl]ethyl}-1-phenylcyclohexanecarboxamide (Example 211, 1.2 g, 2.19 mmol) and aqueous formaldehyde (37%, 820 μl, 10.94 mmol) in acetonitrile (20 mL) and the mixture was stirred at room temperature for 15 minutes. Acetic acid was added until the pH was neutral. The mixture was stirred at room temperature for 45 minutes, adding further acetic acid to maintain neutral pH. The solvent was evaporated under reduced pressure and aqueous sodium hydroxide (1M, 20 mL) and dichloromethane (20 mL) were added. The layers were separated and the aqueous layer was extracted dichloromethane (2×20 mL). The combined organic fractions were washed with brine (40 mL), dried (Na₂SO₄) and the solvent was evaporated under reduced pressure to give the title compound (1.26 g, 100%). m/z (ES⁺) 563 (M+1).

EXAMPLE 213

Trans-(RS)-4-Methylamino-N-{1-[3,5-bis(trifluoromethyl)phenyl]ethyl}-1-phenylcyclohexanecarboxamide Prepared from trans-(RS)-4-[N-methyl(phenylmethyl)amino]-N-{1-[3,5-bis(trifluoromethyl) phenyl]ethyl}-1-phenylcyclohexanecarboxamide (Example 212) according to the method of Example 229. m/z (ES$^+$) 473 (M+1).

EXAMPLE 214

Trans-(RS)-4-Amino-N-{1-[3,5-bis(trifluoromethyl)phenyl]ethyl}-1-phenylcyclohexanecarboxamide Triphenylphosphine (1.0 g, 3.82 mmol) was added to a solution of trans-(RS)-4-azido-N-{1-[3,5-bis(trifluoromethyl)phenyl]ethyl}-1-phenylcyclohexanecarboxamide (Description 28, 920 mg, 1.90 mmol) in tetrahydrofuran (10 mL) and water (1 mL) and the mixture was heated under reflux for 24 hours. The mixture was cooled and the solvent was evaporated under reduced pressure. The residue was purified by flash column chromatography on silica gel, eluting with $CH_2Cl_2$/MeOH/$NH_3$(Aq.) (80:20:2), to give the title compound as a colorless solid (670 mg, 87%). m/z (ES$^+$) 459 (M+1), 442 (M+1-$NH_3$).

EXAMPLE 215

Trans-(RS)-4-(Dimethylamino)-N-{1-[3,5-bis(trifluoromethyl)phenyl]ethyl}-1-phenylcyclohexanecarboxamide Palladium hydroxide (50 mg) was added to a solution of trans-(RS)-4-amino-N-{1-[3,5-bis(trifluoromethyl)phenyl]ethyl}-1-phenylcyclohexanecarboxamide (Example 214, 50 mg, 0.11 mmol) and aqueous formaldehyde (37%, 2 mL) in methanol (10 mL) and the mixture was shaken under an atmosphere of hydrogen (50 psi) for 18 hours. The mixture was filtered through a glass fibre pad, washing with methanol, and the solvent was evaporated under reduced pressure. The residue was dissolved in ethyl acetate, washed with aqueous sodium carbonate (saturated), dried ($MgSO_4$) and the solvent was evaporated under reduced pressure. The residue was dissolved in ethanol and ethereal hydrogen chloride (1M) was added. The solvent was evaporated under reduced pressure and the residue was crystallised from EtOAc/Et$_2$O (50:50) to give the title compound as a colorless solid (20 mg, 35%). m/z (ES$^+$) 487 (M+1).

EXAMPLE 216

Trans-(RS)-4-[4-(Phenylbutyl)amino]-N-{1-[3,5-bis(trifluoromethyl)phenyl]ethyl}-1-phenylcyclohexanecarboxamide Hydrochloride Prepared from trans-(RS)-4-amino-N-{1-[3,5-bis(trifluoromethyl)phenyl]ethyl}-1-phenylcyclohexanecarboxamide (Example 214) and benzenebutanal (Description 17) according to the method of Example 55. m/z (ES$^+$) 591 (M+1).

The following compounds were prepared from trans-(RS)-4-amino-N-{1-[3,5-bis(trifluoromethyl)phenyl]ethyl}-1-phenylcyclohexanecarboxamide (Example 214) according to the method of Example 45, substituting a suitable aldehyde or ketone for benzylamine.

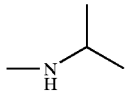

Trans-(RS)

| Ex. | —NR$_2$ | Formula | M.W. | m/z (ES$^+$) (M + 1). |
|---|---|---|---|---|
| 217 | 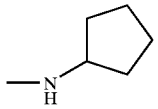 | C26H30F6N2O | 500 | 501 |
| 218 | 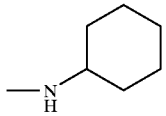 | C28H32F6N2O | 526 | 527 |
| 219 | 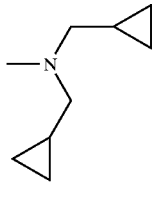 | C29H34F6N2O | 540 | 541 |
| 220 | 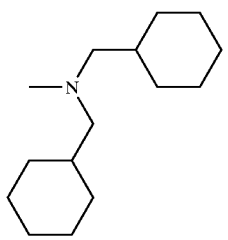 | C31H36F6N2O | 566 | 567 |
| 221 | 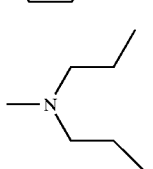 | C37H48F6N2O | 650 | 651 |
| 222 | 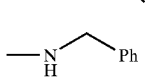 | C29H36F6N2O | 542 | 543 |
| 223 | —NH—CH$_2$—Ph | C30H30F6N2O | 548 | 549 |

EXAMPLE 224

Trans-(RS)-4-[N-Methyl-4-(phenylbutyl)amino]-{1-[3,5-bis(trifluoromethyl)phenyl]ethyl}-1-phenylcyclohexanecarboxamide Prepared from trans-(RS)-4-[4-(phenylbutyl)amino]-N-{1-[3,5-bis(trifluoromethyl)phenyl]ethyl}-1-phenylcyclohexanecarboxamide Hydrochloride (Example 216) according to the method of Example 215. m/z (ES$^+$) 605 (M+1).

EXAMPLE 225

Trans-(RS)-4-Acetylamino-N-{1-[3,5-bis(trifluoromethyl)phenyl]ethyl}-1-phenylcyclohexanecarboxamide Acetic anhydride (0.1 mL, 1.1 mmol) was added to a solution of trans-(RS)-4-amino-N-{1-[3,5-bis(trifluoromethyl)phenyl]ethyl}-1-phenylcyclohexanecarboxamide (Example 214, 50 mg, 0.11 mmol) in dichloromethane (5 mL) and the mixture was stirred at room temperature overnight. The mixture was diluted with dichloromethane (50 mL) and washed with aqueous sodium carbonate (saturated) and water, dried (MgSO$_4$), and the solvent was evaporated under reduced pressure to give the title compound as a colorless foam, (54 mg, 98%). m/z (ES$^+$) 501 (M+1).

EXAMPLE 226

Trans-(RS)-4-[(1-Oxo-4-phenylbutyl)amino]-N-{1-[3,5-bis(trifluoromethyl)phenyl]ethyl{-1-phenylcyclohexanecarboxamide Prepared from trans-(RS)-4-amino-N-{1-[3,5-bis(trifluoromethyl)phenyl]ethyl}-1-phenylcyclohexanecarboxamide (Example 214) and benzenebutanoic acid (27 mg, 0.16 mmol) according to the method of Example 158. m/z (ES$^+$) 605 (M+1).

EXAMPLE 227

Cis- and Trans-(RS)-1-Dimethylethyl 4-[1-({1-[3,5-Bis(trifluoromethyl)phenyl]ethylamino}carbonyl)-1-phenylcyclohexy-4-yl]-1-piperazinecarboxylate Prepared as a mixture of cis- and trans-isomers from (RS)-4-oxo-1-phenyl-N-{1-[3,5-bis(trifluoromethyl)phenyl]ethyl}cyclohexanecarboxamide (Example 18) and 1,1-dimethylethyl 1-piperazinecarboxylate according to the method of Example 45. m/z (ES$^+$) 628 (M+1).

EXAMPLE 228

Trans-(RS)-4-[4-(Phenylmethyl)piperazin-1-yl]-N-{1-[3,5-bis(trifluoromethyl)phenyl]ethyl}-1-phenylcyclohexanecarboxamide Bis(2-oxo-3-oxazolidinyl)phosphinic chloride (1.56 g, 6.12 mmol) was added to a mixture of trans-4-[4-(phenylmethyl)piperazin-1-yl]-1-phenylcyclohexanecarboxylic acid hydrochloride (Description 25, 1.92 g, 5.1 mmol) and triethylamine (3.55 mL, 25.5 mmol) in dichloromethane (200 mL) and the mixture was stirred at room temperature for 15 minutes. (RS)-α-Methyl-3,5-bis(trifluoromethyl) benzenemethanamine hydrochloride (Description 5, 1.64 g, 5.6 mmol) was added and the mixture was stirred at room temperature for 3 days. The solvent was evaporated under reduced pressure and aqueous sodium carbonate (10%, 100 mL) and ethyl acetate (100 mL) were added. The layers were separated and the aqueous layer was extracted with ethyl acetate(100 mL). The combined organic fractions were washed with aqueous sodium carbonate (10%, 100 mL) and brine (20 mL), dried (MgSO$_4$) and the solvent was evaporated under reduced pressure. The residue was dissolved in ethyl acetate (25 mL) and ethereal hydrogen chloride (1M, 10.2 mL) was added. The solid was collected and aqueous sodium carbonate (10%, 100 mL) and ethyl acetate (100 mL) were added. The layers were separated and the aqueous layer was extracted with ethyl acetate (100 mL). The combined organic fractions were washed with aqueous sodium carbonate (10%, 100 mL) and brine (20 mL), dried (MgSO$_4$) and the solvent was evaporated under reduced pressure to give the title compound (1.7 g, 54%). m/z (ES$^+$) 618 (M+1).

EXAMPLE 229

Trans-(RS)-4-(Piperazin-1-yl)-N-{3,5-bis(trifluoromethylphenyl]ethyl}-1-phenylcyclohexanecarboxamide Palladium hydroxide on carbon (20%, 20 mg) was added to a mixture of trans-(RS)-4-[4-(phenylmethyl)piperazin-1-yl]-N-{1-[3,5-bis(trifluoromethyl) phenyl]ethyl}-1-phenylcyclohexanecarboxamide (Example 228, 700 mg, 1.3 mmol), hydrochloric acid (1M, 2.6 mL) and acetic acid (5 mL) in ethyl acetate (50 mL) and the mixture was shaken under an atmosphere of hydrogen (50 psi) for 20 hours. The mixture was filtered through a glass fibre pad, washing with ethyl acetate, and the solvent was evaporated under reduced pressure. The residue was dissolved in dichloromethane (20 mL) and washed with aqueous sodium carbonate (10%, 20 mL) and brine (20 mL), dried (MgSO$_4$) and the solvent was evaporated under reduced pressure. The residue was purified by flash column chromatography on silica gel, eluting with CH$_2$Cl$_2$/MeOH/NH$_3$(Aq.) (90:10:1), to give the title compound. m/z (ES$^+$) 528 (M+1).

The following compounds were prepared from trans-(RS)-4-(piperazin-1-yl)-N-{1-[3,5-bis(trifluoromethyl) phenyl]ethyl}-1-phenylcyclohexanecarboxamide (Example 229) according to the method of Example 45, substituting a suitable aldehyde or ketone for (RS)-β-[(4-oxo-1-phenylcyclohexyl)methoxy]-3,5-bis(trifluoromethyl) benzeneethanol.

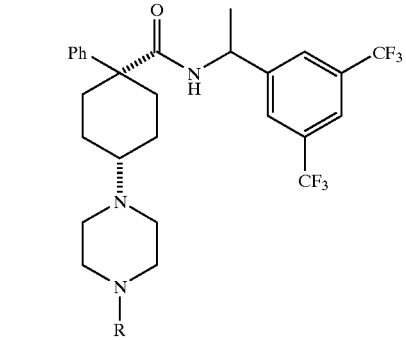

Trans-(RS)

| Ex. | —R | Formula | M.W. | m/z (ES$^+$) (M + 1). |
|---|---|---|---|---|
| 230 |  | C32H35F6N3O2 | 607 | 608 |
| 231 | 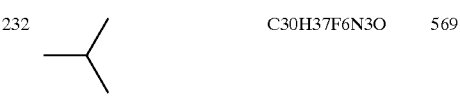 | C31H37F6N3O | 581 | 582 |
| 232 | | C30H37F6N3O | 569 | 570 |

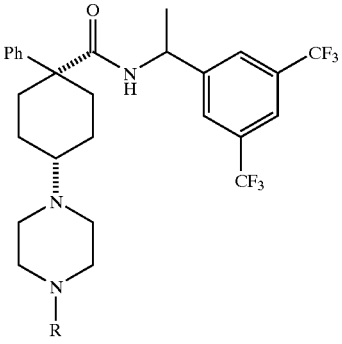

Trans-(RS)

| Ex. | —R | Formula | M.W. | m/z (ES+) (M + 1). |
|---|---|---|---|---|
| 233 | 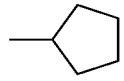 | C32H39F6N3O | 595 | 596 |
| 234 | 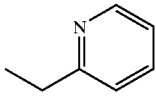 | C36H35F12N3O | 753 | 754 |
| 235 | 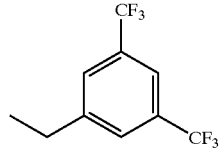 | C35H39F6N3O2 | 647 | 648 |
| 236 | 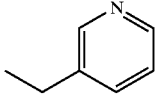 | C34H43F6N3O | 623 | 624 |
| 237 | 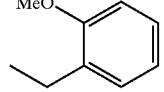 | C33H43F6N3O | 611 | 612 |
| 238 | 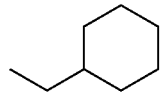 | C31H39F6N3O | 583 | 584 |
| 239 | 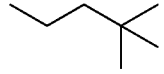 | C32H35F6N3OS | 623 | 624 |
| 240 | 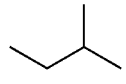 | C32H35F6N3OS | 623 | 624 |
| 241 | 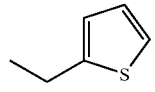 | C35H39F6N3O | 631 | 632 |
| 242 | 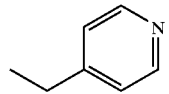 | C31H34F6N4OS | 624 | 625 |
| 243 |  | C33H36F6N4O | 618 | 619 |

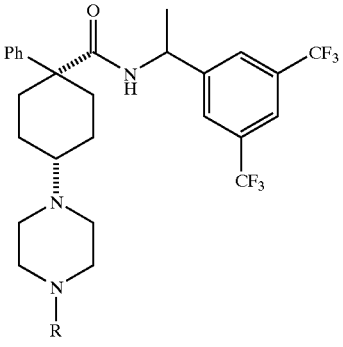

Trans-(RS)

| Ex. | —R | Formula | M.W. | m/z (ES+) (M + 1). |
|---|---|---|---|---|
| 244 |  | C33H36F6N4O | 618 | 619 |
| 245 |  | C33H36F6N4O | 618 | 619 |

EXAMPLE 246

Trans-(RS)-4-(4Methylpiperazin-1-yl)-N-{1-[3,5-bis(trifluoromethyl)phenyl]ethyl}-1-phenylcyclohexanecarboxamide Prepared from trans-(RS)-4-(piperazin-1-yl)-N-{1-[3,5-bis(trifluoromethyl)phenyl]ethyl}-1-phenylcyclohexanecarboxamide (Example 229) according to the method of Example 215. m/z (ES+) 542 (M+1).

EXAMPLE 247

Trans-(RS)-4-(4-Acetylpiperazin-1-yl)-N-{1-[3,5-bis(trifluoromethyl)phenyl]ethyl}-1-phenylcyclohexanecarboxamide Acetyl chloride (100 μl) was added to a solution of trans-(RS)-4-(piperazin-1-yl)-N-{1-[3,5-bis(trifluoromethyl)phenyl]ethyl}-1-phenylcyclohexanecarboxamide (Example 229, 25 mg, 0.05 mmol) in dichloromethane (3 mL) and the mixture was stirred at room temperature for 20 minutes. The solvent was evaporated under reduced pressure and the residue was dissolved in ethyl acetate (20 mL). The mixture was washed with aqueous sodium carbonate (10%, 20 mL) and brine (20 mL), dried (MgSO$_4$) and the solvent was evaporated under reduced pressure to give the title compound (27 mg, 95%). m/z (ES+) 570 (M+1).

The following compounds were prepared from trans-(RS)-4-(piperazin-1-yl)-N-{1-[3,5-bis(trifluoromethyl)phenyl]ethyl}-1-phenylcyclohexanecarboxamide (Example 229) according to the method of Example 247, substituting a suitable acid chloride for acetyl chloride.

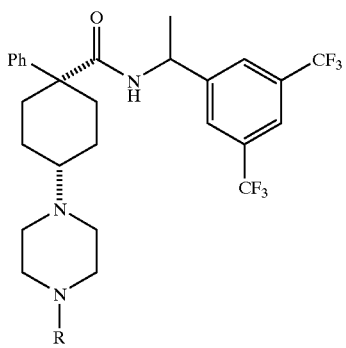

| Ex. | —R | Trans-(RS) Formula | M.W. | m/z (ES+) (M + 1). |
|---|---|---|---|---|
| 248 | 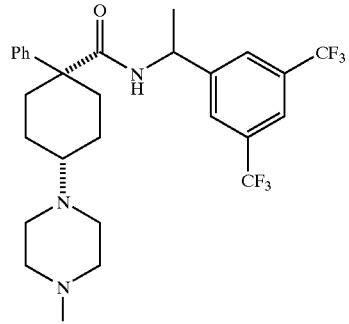 | C30H35F6N3O2 | 583 | 584 |
| 249 |  | C31H37F6N3O2 | 597 | 598 |
| 250 | 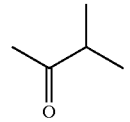 | C34H35F6N3O2 | 631 | 632 |
| 251 |  | C34H41F6N3O2 | 637 | 638 |
| 252 | 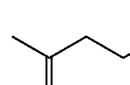 | C31H35F6N3O2 | 595 | 596 |
| 253 |  | C35H37F6N3O2 | 645 | 646 |

The following compounds were prepared from trans-(RS)-4-(piperazin-1-yl)-N-{1-[3,5-bis(trifluoromethyl)phenyl]ethyl}-1-phenylcyclohexanecarboxamide (Example 229) according to the method of Example 158, substituting a suitable acid for trans-4-[4-(4-fluorophenyl)piperidin-1-yl]-1-phenylcyclohexanecarboxylic acid hydrochloride.

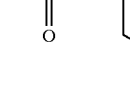

| Ex. | —R | Trans-(RS) Formula | M.W. | m/z (ES+) (M + 1). |
|---|---|---|---|---|
| 254 |  | C31H37F6N3O2 | 597 | 598 |
| 255 | 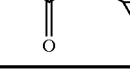 | C36H45F6N3O2 | 665 | 666 |
| 256 |  | C35H43F6N3O2 | 651 | 652 |
| 257 |  | C32H37F6N3O2 | 609 | 610 |

EXAMPLE 258

Trans-(RS)-4-(Aminomethyl)-N-{1-[3,5-bis(trifluoromethyl)phenyl]ethyl}-1-phenylcyclohexanecarboxamide Raney nickel (10 mg) was added to a solution of trans-(RS)-4-cyano-N-{1-[3,5-bis(trifluoromethyl) phenyl]ethyl}-1-phenylcyclohexanecarboxamide (Description 29, 50 mg, 0.11 mmol) in methanolic ammonia (2M, 50 mL) and the mixture was shaken under an atmosphere of hydrogen (45 psi) for 4 hours. Further Raney nickel (10 mg) was added and the mixture was shaken under an atmosphere of hydrogen (45 psi) for 2 hours. The mixture was filtered through a glass fibre pad, washing with methanol, and the solvent was evaporated under reduced pressure. The residue was purified by flash column chromatography on silica gel, eluting with CH$_2$Cl$_2$/MeOH/NH$_3$(Aq.) (95:5:0.5), to give the title compound. m/z (ES+) 473 (M+1).

EXAMPLE 259

Trans-(RS)-4-(N,N-Dimethylaminomethyl)-N-{1-[3,5-bis(trifluoromethyl)phenyl]ethyl}-1-phenylcyclohexanecarboxamide Prepared from trans-(RS)-4-(aminomethyl)-N-{1-[3,5-bis(trifluoromethyl) phenyl]ethyl}-1- phenylcyclohexanecarboxamide (Example 258) according to the method of Example 214. m/z (ES$^+$) 501 (M+1).

EXAMPLE 260

Trans-(RS)-4-[(Piperidin-1-yl)methyl]-N-{1-[3,5-bis(trifluoromethyl)phenyl]ethyl)-1-phenylcyclohexanecarboxamide 1,5-Dibromopentane (14 µl, 0.106 mmol) was added to a mixture of trans-(RS)-4-(aminomethyl)-N-{1-[3,5-bis(trifluoromethyl) phenyl]ethyl}-1-phenylcyclohexanecarboxamide (Example 258, 50 mg, 0.106 mmol), potassium carbonate (23 mg, 0.212 mmol) and sodium iodide (8 mg, 0.053 mmol) in dimethylformamide (10 mL) and the mixture was stirred at 100° C. for 5 h, then at room temperature overnight. Ether (25 mL) and water (25 mL) were added and the layers were separated. The aqueous layer was extracted with ether (25 mL) and the combined organic fractions were washed with water (25 mL) and brine (25 mL), dried (MgSO$_4$) and the solvent was evaporated under reduced pressure. The residue was purified by flash column chromatography on silica gel, eluting with CH$_2$Cl$_2$/MeOH/NH$_3$(Aq.) (95:5:0.5), and the residue was dissolved in methanol (0.5 mL) and poured onto an SCX cartridge (Varian Bond Elut™; 10 mL/500 mg). The cartridge was washed with methanol (2×5 mL), then eluted with methanolic ammonia (2M, 5 mL). The solvent was evaporated under reduced pressure to give the title compound (20 mg, 35%). m/z (ES$^+$) 541 (M+1).

EXAMPLE 261

Trans-(RS)-4-[(Morpholin-4-yl)methyl]-N-{1-[3,5-bis(trifluoromethyl)phenyl]ethyl}-1-phenylcyclohexanecarboxamide Prepared from trans-(RS)-4-(aminomethyl)-N-{1-[3,5-bis(trifluoromethyl) phenyl]ethyl}-1-phenylcyclohexanecarboxamide (Example 258) according to the method of Example 260, substituting bis(2-bromoethyl)ether for 1,5-dibromopentane. m/z (ES$^+$) 543 (M+1).

EXAMPLE 262

Trans-(RS)-4-({N-[2-(Dimethylamino)acetyl]}aminomethyl)-N-{1-[3,5-bis(trifluoromethyl)phenyl]ethyl}-1-phenylcyclohexanecarboxamide 1-(Dimethylaminopropyl)-3-ethylcarbodiimide hydrochloride (26 mg, 0.138 mmol) was added to a mixture of N,N-dimethylglycine (13 mg, 0.127 mmol), triethylamine (44 µl, 0.318 mmol) and 1-hydroxybenzotriazole (14 mg, 0.106 mmol) in dichloromethane (5 mL) and the mixture was stirred at room temperature for 10 minutes. A solution of trans-(RS)-4-(aminomethyl)-N-{1-[3,5-bis(trifluoromethyl) phenyl]ethyl}-1-phenylcyclohexanecarboxamide (Example 258, 50 mg, 0.106 mmol) in dichloromethane (6 mL) was added and the mixture was stirred at room temperature overnight Water (25 mL) was added and the mixture was extracted with ethyl acetate (2×25 mL). The combined organic fractions were washed with brine (25 mL), dried (MgSO$_4$) and the solvent was evaporated under reduced pressure. The residue was purified by flash column chromatography on silica gel, eluting with CH$_2$Cl$_2$/MeOH/NH$_3$(Aq.) (95:5:0.5) to give the title compound (50 mg, 85%). m/z (ES$^+$) 558 (M+1).

EXAMPLE 263

Trans-(RS)-4-(1H-1,2,3-Triazol-1-yl)-N-{1-[3,5-bis(trifluoromethyl)phenyl]ethyl}-1-phenylcyclohexanecarboxamide (Trimethylsilyl)acetylene (0.3 mL, 2.0 mmol) was added to a solution of trans-(RS)-4-azido-N-{1-[3,5-bis(trifluoromethyl)phenyl]ethyl}-1-phenylcyclohexanecarboxamide (Description 28, 50 mg, 0.1 mmol) in toluene and the mixture was stirred at 80° C. for 48 hours. The mixture was cooled, the solvent was evaporated under reduced pressure and the residue was purified by flash column chromatography on silica gel, eluting with isohexane/EtOAc (60:40). The residue was dissolved in tetrahydrofuran (5 mL) and acetic acid (68 µl, 1.16 mmol) and tetrabutylammonium fluoride (1M solution in tetrahydrofuran, 0.35 mL, 0.35 mmol) were added. The mixture was stirred at room temperature for 3 days and the solvent was evaporated under reduced pressure. Ethyl acetate and aqueous sodium carbonate (saturated) were added and the layers were separated. The organic layer was dried (MgSO$_4$) and the solvent evaporated under reduced pressure. The residue was purified by flash column chromatography on silica gel, eluting with isohexane/EtOAc (50:50), to give the title compound as a colourless foam (30 mg, 59%). m/z (ES$^+$) 511 (M+1), 442 (M+1-C$_2$H$_3$N$_3$).

EXAMPLE 264

Trans-N-({4-[4-(4-Fluorophenyl)piperidin-1-yl]-1-phenylcyclohexl}methyl)-3,5-bis(trifluoromethyl)benzenecarboxamide 3,5-Bis(trifluoromethyl)benzoyl chloride (54 µl, 0.3 mmol) was added dropwise to a solution of trans-4-[4-(4-fluorophenyl)piperidin-1-yl]-1-phenylcyclohexanemethanamine (Description 32, 100 mg, 0.27 mmol) in dichloromethane (5 mL) and the mixture was stirred at room temperature for 90 minutes. Water (5 mL) and saturated aqueous sodium hydrogen carbonate (2 mL) were added and the layers were separated. The aqueous layer was extracted with ethyl acetate (20 mL) and the combined organic fractions were washed with brine (10 mL), dried (MgSO$_4$) and the solvent was evaporated under reduced pressure. The residue was dissolved in methanol (0.5 mL) and poured onto an SCX cartridge (Varian Bond Elut™; 10 mL/500 mg). The cartridge was washed with methanol (2×5 mL), then eluted with methanolic ammonia (2M, 5 mL). The solvent was evaporated under reduced pressure to give the title compound (105 mg, 64%). m/z (ES$^+$) 607 (M+1).

EXAMPLE 265

Trans-N-({4-[4-(4-Fluorophenyl)piperidin-1-yl]-1-phenylcyclohexyl}methyl)-2-(methoxy)benzenemethanamine Sodium triacetoxyborohydride (286 mg, 1.35 mmol) was added to a solution of trans-4-[4-(4-fluorophenyl)piperidin-1-yl]-1-phenylcyclohexanemethanamine (Description 32, 100 mg, 0.27 mmol) and 2-methoxybenzaldehyde (33 µl, 0.27 mmol) in dichloroethane (10 mL) and the mixture was stirred at room temperature for 24 hours. Water (10 mL) and saturated aqueous sodium hydrogen carbonate (20 mL) were added and the mixture was extracted with ethyl acetate (2×20 mL). The combined organic fractions were washed with brine (10 mL), dried (MgSO$_4$) and the solvent was evaporated under reduced pressure. The residue was dissolved in methanol (0.5 mL) and poured onto an SCX cartridge (Varian Bond Elut™; 10 mL/500 mg). The cartridge was washed with methanol (2×5 mL), then eluted with methanolic ammonia (2M, 5 mL). The solvent was evaporated under reduced pressure and the residue was purified by flash column chromatography on silica gel, eluting with CH$_2$Cl$_2$/MeOH/NH$_3$(Aq.) (95:5:0.5), to give the title compound (25 mg, 19%). m/z (ES$^+$) 487 (M+1).

EXAMPLE 266

Cis-N-({4-[4-(4-Fluorophenyl)piperidin-1-yl]-1-phenylcyclohexyl}methyl)-3,5-bis(trifluoromethyl)benzenemethanamine and Trans-N-({4-[4-(4-Fluorophenyl)piperidin-1-yl]-1-phenylcyclohexyl}methyl)-3,5-bis(trifluoromethyl)benzenemethanamine Palladium on activated carbon (5%) was added to a solution of 4-[4-(4-fluorophenyl)piperidin-1-yl]-1-phenylcyclohexanecarbonitrile (mixture of cis- and trans-isomers, Description 30, 180 mg, 0.5 mmol) and hydrochloric acid (conc., 5 mL) in methanol (15 mL) and the mixture was shaken under an atmosphere of hydrogen (50 psi) for 65 hours. Additional palladium on activated carbon (5%) was added and the mixture was shaken under an atmosphere of hydrogen (50 psi) for 24 hours. The mixture was filtered through a glass fibre pad, washing with methanol, and the solvent was evaporated under reduced pressure. The residue was dissolved in ethyl acetate (10 mL) and saturated aqueous sodium hydrogen carbonate (10 mL) was added. The mixture was filtered and the layers were separated. The organic layer was washed with brine (10 mL), dried ($MgSO_4$) and the solvent was evaporated under reduced pressure. The residue was dissolved in methanol (10 mL) and 3,5-bis(trifluoromethyl) benzaldehyde (42 mg, 0.17 mmol) and a mixture of sodium cyanoborohydride (11 mg, 0.17 mmol) and zinc chloride (12 mg, 0.085 mmol) in methanol (10 mL) were added. The mixture was stirred at room temperature overnight, poured into saturated aqueous sodium hydrogen carbonate (10 mL) and extracted with ethyl acetate (2×10 mL). The combined organic fractions were washed with brine (10 mL), dried ($MgSO_4$) and the solvent was evaporated under reduced pressure. The residue was purified by preparative HPLC (ABZ+; 250×10.0 mm id; 34% MeCN in 0.1% TFA-$H_2O$; 5 ml/min; 210 nm) to give: cis-N-({4-[4-(4-fluorophenyl)piperidin-1-yl]-1-phenylcyclohexyl}methyl)-3,5-bis(trifluoromethyl)benzenemethanamine; $^1$H NMR (400 MHz, $CDCl_3$) δ 7.73 (1H, s), 7.70 (2H, s), 7.38–7.33 (4H, m), 7.25–7.16 (3H, m), 6.97 (2H, t, J 8.7 Hz), 3.77 (2H, s), 3.08–3.00 (2H, m), 2.79 (2H, s), 2.52–2.41 (1H, m), 2.36 (2H, d, J 12.8 Hz), 2.30–2.17 (2H, M), 1.89–1.38 (8H, m), and 0.90–0.81 (2H, m); m/z ($ES^+$) 593 (M+1); trans-N-({4-[4-(4-fluorophenyl)piperidin-1-yl]-1-phenylcyclohexyl}methyl)-3,5-bis(trifluoromethyl)benzenemethanamine; $^1$H NMR (400 MHz, $CDCl_3$) δ 7.71 (1H, s), 7.65 (2H, s), 7.39–7.34 (4H, m), 7.24–7.19 (1H, m), 7.15–7.11 (2H, m), 6.96–6.92 (2H, m), 3.71 (2H, m), 2.93 (2H, br d, J 11.5 Hz), 2.58 (2H, br d, J 12.4 Hz), 2.51 (2H, s), 2.40–2.35 (2H, m), 2.18–2.12 (2H, m), 1.81–1.74 (4H, m), 1.69–1.59 (2H, m), 1.48–1.40 (2H, m), and 1.35–1.26 (2H, m). m/z ($ES^+$) 593 (M+1).

EXAMPLE 267

Trans-N-({4-[4-(4-Fluorophenyl)piperidin-1-yl]-1-phenylcyclohexyl}methyl)-N-methyl-3,5-bis(trifluoromethyl)benzenemethanamine Formaldehyde (37% w/v in water, 2 mL), palladium hydroxide on carbon (20%, 10 mg) and acetic acid (24 μl, 0.42 mmol) were added to a solution of trans-N-({4-[4-(4-fluorophenyl)piperidin-1-yl]-1-phenylcyclohexyl}methyl)-3,5-bis(trifluoromethyl) benzenemethanamine (Example 266, 102 mg, 0.17 mmol) in methanol (10 mL) and the mixture was shaken under an atmosphere of hydrogen (50 psi) for 2.5 hours. Additional palladium hydroxide on carbon (20%, 10 mg) was added and and the mixture was shaken under an atmosphere of hydrogen (50 psi) for 1 hour. The mixture was filtered through a glass fibre pad, washing with methanol, and the solvent was evaporated under reduced pressure. The residue was dissolved in methanol (0.5 mL) and poured onto an SCX cartridge (Varian Bond Elut™; 10 ml/500 mg). The cartridge was washed with methanol (2×5 mL), then eluted with methanolic ammonia (2M, 5 mL). The solvent was evaporated under reduced pressure to give the title compound. m/z ($ES^+$) 607 (M+1).

EXAMPLE 268

Cis- and Trans-N-({4-[4-(4-Fluorophenyl)piperidin-1-yl]-1-phenylcyclohexyl}methyl)-N-{[3,5-bis(trifluoromethyl)phenyl]methyl}acetamide Prepared as a mixture of cis- and trans-isomers from N-[(4-oxo-1-phenylcyclohexyl)methyl]-N-{[3,5-bis(trifluoromethyl)phenyl]methyl}acetamide (Example 21) and 4-(4-fluorophenyl)piperidine (Description 16) according to the method of Example 55. m/z ($ES^+$) 635 (M+1).

EXAMPLE 269

Trans-(RS)-N-({[4-[4-(4-Fluorophenyl)piperidin-1-yl]-1-phenylcyclohexyl}methyl)-α-methyl-3,5-bis(trifluoromethyl)benzenemethanamine Borane-tetrahydrofuran complex (1M in tetrahydrofuran, 0.2 mL) was added to a solution of trans-(RS)-4-[4-(4-fluorophenyl)piperidin-1-yl]-N-{1-[3,5-bis(trifluoromethyl)phenyl]ethyl}-1-phenylcyclohexanecarboxamide (Example 177, 20 mg, 0.032 mmol) in tetrahydrofuran (5 mL) and the mixture was heated under reflux for 24 hours. The mixture was cooled and methanol (10 mL) was added. The mixture was heated under reflux for 1 hour, cooled and the solvent was evaporated under reduced pressure. The residue was dissolved in ethyl acetate and washed with water, aqueous sodium carbonate (saturated) and water, dried ($MgSO_4$), and the solvent was evaporated under reduced pressure. The residue was purified by flash column chromatography on silica gel eluting with $CH_2Cl_2$/MeOH/$NH_3$(Aq.) (95:5:0.5). The residue was dissolved in diethyl ether and ethereal hydrogen chloride (1M) was added. The solvent was evaporated under reduced pressure to give the title compound as a colorless solid (20 mg, 97%). m/z ($ES^+$) 607 (M+1).

EXAMPLE 270

Trans-(RS)-α-({4-[4-(4-Fluorophenyl)piperidin-1-yl]-1-phenylcyclohexyl}methylamino)-3,5-bis(trifluoromethyl)benzeneethanol and Trans-(RS)-α-({4-[4-(4-Fluorophenyl)piperidin-1-yl]-1-phenylcyclohexyl}methylamino)-3,5-bis(trifluoromethyl)benzeneethanamine A solution of trans-(RS)-methyl α-({4-[4-(4-fluorophenyl)piperidin-1-yl]-1-phenylcyclohexyl}carbonylamino)-3,5-bis(trifluoromethyl)benzeneacetate (Example 157, 0.25 mmol) in methanol (1.5 mL) was poured onto an SCX cartridge (Varian Bond Elut™; 10 mL/500 mg). The cartridge was washed with methanol (4×1 mL), then eluted with methanolic ammonia (2M, 4×1 mL). The solvent was evaporated under reduced pressure and the residue was dissolved in tetrahydrofuran (4 mL) and toluene (2 mL) and lithium borohydride (10 mg, 0.46 mmol) was added. The mixture was stirred at room temperature for 30 minutes, then at 50° C. for 30 minutes. The mixture was cooled and hydrochloric acid (2M) and ethyl acetate were added. The layers were separated, the organic fraction was dried ($Na_2SO_4$) and the solvent was evaporated under reduced pressure. The residue was dissolved in tetrahydrofuran (2 mL) and borane-tetrahydrofuran complex (1M in tetrahydrofuran, 1 mL) was added. The mixture was stirred at 60° C. for 1 hour, then further borane-tetrahydrofuran complex (1M in tetrahydrofuran, 1 mL) was added and the mixture was stirred at 60° C. for 1 hour. The mixture was cooled and aqueous sodium carbonate (10%, 20 mL) and ethyl acetate (20 mL) were added. The layers were separated and the aqueous fraction was extracted with ethyl acetate (10 mL). The combined organic fractions were dried ($Na_2SO_4$) and the solvent was evaporated under reduced pressure. The residue was dissolved in methanol (3 mL) and heated under reflux for 3 hours. The mixture was cooled and the solvent was evaporated under reduced pressure. The residue was dissolved in dichloromethane, filtered and the solvent was evaporated under reduced pressure. The residue was purified by preparative thin layer chromatography on silica gel, eluting with $CH_2Cl_2$/MeOH/$NH_3$(Aq.) (95:5:0.5) to give: trans-(RS)-α-({4-[4-(4-fluorophenyl)piperidin-1-yl]-1-phenylcyclohexyl}methylamino)-3,5-bis(trifluoromethyl) benzeneethanol (25 mg, 16%); $^1$H NMR (400 MHz, $CDCl_3$) δ 7.75 (1H, s), 7.52 (2H, s), 7.40–7.30 (4H, m), 7.27–7.17 (1H, m), 7.20–7.10 (2H, m), 6.95 (2H, t, J 8.0 Hz), 3.65 (1H, dd, J 8.2, 4.2 Hz), 3.57 (1H, dd, J 10.7, 4.2 Hz), 3.31 (1H, dd, J 10.7, 8.2 Hz), 2.95 (2H, br d, J 11.0 Hz), 2.55 (2H, br d, J 11.0 Hz), 2.50–2.30 (2H, m), 2.46 (1H, d, J 11.0 Hz), 2.36 (1H, d, J 11.0 Hz), 2.20 (2H, br t, J 11.0 Hz), 2.10–1.60 (6H, m), and 1.55–1.20 (4H, m); m/z ($ES^+$) 623 (M+1); and trans-(RS)-α-({4-[4-(4-fluorophenyl)piperidin-1-yl]-1-phenylcyclohexyl}methylamino)-3,5-bis(trifluoromethyl) benzeneethanamine; $^1$H NMR (360 MHz, $CDCl_3$) δ 7.74 (1H, s), 7.60 (2H, s), 7.40–7.30 (4H, m), 7.27–7.17 (1H, m), 7.18–7.08 (2H, m), 6.94 (2H, t, J 8.0 Hz), 3.45 (1H, dd, J 7.6, 4.8 Hz), 2.96 (2H, br d, J 10 Hz), 2.77 (1H, dd, J 12.0, 4.8 Hz), 2.57 (1H, dd, J 12.0, 7.6 Hz), and 2.55–1.40 (20H, m). m/z ($ES^+$) 622 (M+1).

EXAMPLE 271

Cis- and Trans-(E)-4-(4-Fluorophenyl)-1-(4-phenyl-4-[3,5-bis(trifluoromethyl)phenyl]-prop-1-enyl}cyclohexyl)piperidine Prepared as a mixture of cis- and trans-isomers from (E)-4-phenyl-4-{3-[3,5-bis(trifluoromethyl)phenyl]prop-1-enyl}cyclohexanone Example 22) and 4-(4-fluorophenyl)piperidine (Description 16) according to the method of Example 45. m/z ($ES^+$) 590 (M+1).

EXAMPLE 272

Cis- and Trans-(E)-4-(4-Fluorophenyl)-1-(4-phenyl-4-{3-[3,5-bis(trifluoromethyl)phenyl] propyl}cyclohexyl)piperidine Prepared as a mixture of cis- and trans-isomers from (E)-4-(4-fluorophenyl)-1-(4-phenyl-4-{3-[3,5-bis (trifluoromethyl)phenyl]prop-1-enyl}cyclohexyl) piperidine (mixture of cis- and trans-isomers, Example 271) according to the method of Description 16. m/z ($ES^+$) 592 (M+1).

EXAMPLE 273

Cis- and Trans-(RS)-4-(4-Fluorophenyl)-1-(4-{2-hydroxy-3-[3,5-bis(trifluoromethyl)phenyl]propyl}-4-phenylcyclohexyl)piperidine Prepared as a mixture of cis- and trans-isomers from (RS)-4-{2-hydroxy-3-[3,5-bis(trifluoromethyl)phenyl]propyl}-4-phenylcyclohexanone (Example 25) and 4-(4-fluorophenyl)piperidine (Description 16) according to the method of Example 45. m/z ($ES^+$) 608 (M+1).

EXAMPLE 274

Cis- and Trans-(RS)-4-(4-Fluorophenyl)-1-(4-{2-oxo-3-[3,5-bis(trifluoromethyl)phenyl] propyl}phenylcyclohexyl)piperidine Prepared as a mixture of cis- and trans-isomers from (RS)-4-(4-fluorophenyl)-1-(4-{2-hydroxy-3-[3,5-bis (trifluoromethyl)phenyl]propyl}-4-phenylcyclohexyl) piperidine (mixture of cis- and trans-isomers, Example 273) according to the method of Description 17. m/z ($ES^+$) 606 (M+1).

EXAMPLE 275

1-{[(1,4-Dioxa-8-phenylspiro[4.5]decan-8-yl) methoxy]methyl}-3,5-bis(trifluoromethyl) benzene Prepared from 8-phenyl-1,4-dioxaspiro[4.5]decane-8-methanol (*J. Org. Chem.* 1974, 39, 2311–2313) and 1-(bromomethyl)-3,5-bis(trifluoromethyl)benzene according to the method of Example 1. $^1$H NMR (360 MHz, $CDCl_3$) δ 1.53–1.65 (4H, m), 1.88–1.96 (2H, m), 2.28–2.32 (2H, m), 3.42 (2H, s), 3.88–3.97 (4H, m), 4.42 (2H, s), 7.20–7.42 (5H, m), 7.55 (2H, s), and 7.72 (1H, s). $C_{24}H_{24}F_6O_3$ requires C, 60.76; H, 5.09; found C, 61.15; H, 5.07.

EXAMPLE 276

1-({[4-Oxo-1-phenylcyclohexyl]methoxy}methyl)-3, 5-bis(trifluoromethyl)benzene

Pyridinium p-toluenesulfonate (100 mg, 0.4 mmol) was added to a solution of 1-{[(1,4-dioxa-8-phenylspiro[4.5] decan-8-yl)methoxy]methyl}-3,5-bis(trifluoromethyl) benzene (Example 275, 5 g, 1 mmol) in acetone-water (8:1, 9 mL) and the mixture was heated under reflux for 3 days. The mixture was cooled and the solvent was evaporated under reduced pressure. Aqueous sodium hydrogen carbonate (saturated) and ethyl acetate were added and the layers were separated. The organic fraction was dried ($MgSO_4$) and the solvent was evaporated under reduced pressure. The residue was purified by flash column chromatography on silica gel, eluting with hexane/EtOAc (70:30), to give the title compound as a colorless oil (350 mg, 83%). $^1$H NMR (360 MHz, $CDCl_3$) δ 2.06–2.10 (2H, m), 2.27–2.38 (4H, m), 2.58–2.65 (2H, m), 3.47 (2H, s), 4.44 (2H, s), 7.29–7.50 (5H, m), 7.56 (2H, s), and 7.75 (1H, s) $C_{22}H_{20}F_6O_2$ requires C, 61.39, H, 4.68; found C, 60.92; H, 4.51.

EXAMPLE 277

Cis-1-({4–4-(4-Fluorophenyl)piperdin-1-yl]-1-phenylcyclohexanemethoxy}methyl)-3,5-bis (trifluoromethyl)benzene and Trans-1-({4-[4-(4-Fluorophenyl)piperidin-1-yl]-1-phenylcyclohexanemethoxy}methyl-3,5-bis (trifluoromethyl)benzene Prepared from 1-({[4-oxo-1-phenylcyclohexyl] methoxy}methyl)-3,5-bis(trifluoromethyl)benzene (Example 276) and 4-(4-fluorophenyl)piperidine (Description 16) according to the method of Example 45:

cis-1-({4-[4-(4-Fluorophenyl)piperidin-1-yl]-1-phenylcyclohexanemethoxy}methyl)-3,5-bis(trifluoromethyl)benzene; $^1$H NMR (400 MHz, CDCl$_3$) δ 7.73 (1H, s), 7.55 (2H, s), 7.42–7.17 (7H, m), 7.00–6.95 (2H, m), 4.45 (2H, s), 3.70 (2H, s), 3.10 (2H, m), 2.47 (1H, m), trans-1-({4-[4-(4-Fluorophenyl)piperidin-1-yl]-1-phenylcyclohexanemethoxy}methyl)-3,5-bis(trifluoromethyl)benzene; $^1$H NMR (400 MHz, CDCl$_3$) δ 7.74 (1H, s), 7.57 (2H, s), 7.39 (4H, m), 7.24 (1H, m), 7.15 (2H, dd, J 8.6, 5.4 Hz), 6.95 (2H, t, J 8.6 Hz), 4.42 (2H, s), 3.33 (2H, s), 3.04 (2H, m), 2.75–1.62 (14H, m), and 1.39 (2H, m). m/z (ES$^+$) 594 (M+1).

EXAMPLE 278

(RS)-4-Methylene-1-phenyl-N-{1-[35-bis(trifluoromethyl)phenyl]ethyl}cyclohexanecarboxamide Methyltriphenylphosphonium bromide (1.71 g, 4.8 mmol) was dried azeotropically by evaporating toluene (3×20 mL) under reduced pressure, suspended in tetrahydrofuran (20 mL) and cooled in ice. Butyllithium (1.6M in hexanes, 3.0 mL, 4.8 mmol) was added and the mixture was stirred at room temperature for 3 hours. The mixture was cooled in ice and (RS)-4-oxo-1-phenyl-N-{1-[3,5-bis(trifluoromethyl)phenyl]ethyl}cyclohexanecarboxamide (Example 18, 0.91 g, 2.0 mmol) in tetrahydrofuran (5 mL) was added. The mixture was stirred at room temperature for 1 hour, then heated under reflux for 3 hours. The mixture was cooled, poured into water (50 mL) and extracted with ethyl acetate (3×50 mL). The combined organic fractions were washed with water (3×50 mL) and brine (50 mL), dried (MgSO$_4$) and evaporated under reduced pressure. The residue was purified by flash column chromatography on silica gel, eluting with CH$_2$Cl$_2$, to give the title compound as a colorless solid (0.67 g, 73%); $^1$H NMR (400 MHz, CD$_3$OD) δ 7.76 (1H, s), 7.69 (2H, s), 7.34–7.20 (5H, m), 5.14 (1H, q, J 7.1 Hz), 4.64 (2H, s), 2.53 (2H, m), 2.27 (4H, m), 1.99 (1H, m), 1.77 (1H, m), and 1.42 (3H, d, J 7.1 Hz).

EXAMPLE 279

Cis-(RS)-4-(Hydroxymethyl)-N-{1-[3,5-bis(trifluoromethyl)phenyl]ethyl}-1-phenylcyclohexanecarboxamide and

Trans-(RS)-4-(Hydroxymethyl)-N-{1-[3,5-bis(trifluoromethyl)phenyl]ethyl}-1-phenylcyclohexanecarboxamide 9-Borabicyclo[3.3.1]nonane (0.5M in tetrahydrofuran, 1.0 mL, 0.5 mmol) was added to a solution of (RS)-4-methylene-1-phenyl-N-{1-[3,5-bis(trifluoromethyl)phenyl]ethyl}cyclohexanecarboxamide (Example 278, 182 mg, 0.4 mmol) in tetrahydrofuran (2 mL) and the mixture was stirred at room temperature for 2 hours. Ethanol (0.5 mL), aqueous sodium hydroxide (4M, 0.2 mL) and aqueous hydrogen peroxide (35%, 0.2 mL) were added and the mixture was stirred at 50° C. for 1 hour. The mixture was cooled, poured into aqueous sodium hydrogen carbonate (saturated, 20 mL) and water (10 mL) and extracted with dichloromethane (3×20 mL). The combined organic fractions were dried (MgSO$_4$) and evaporated under reduced pressure. The residue was purified by MPLC chromatography on silica gel, eluting with isohexane/EtOAc (70:30 increasing to 50:50), to give:

cis-(RS)-4-(hydroxymethyl)-N-{1-[3,5-bis(trifluoromethyl)phenyl]ethyl}-1-phenylcyclohexanecarboxamide (113 mg, 60%), $^1$H NMR (400 MHz, CD$_3$OD) δ 7.76 (1H, s), 7.71 (2H, s), 7.31 (2H, d, J 7.5 Hz), 7.25 (2H, t, J 7.5 Hz), 7.20 (1H, t, J 7.5 Hz), 5.14 (1H, q, J 7.1 Hz), 3.32 (2H, m), 2.67 (2H, m), 1.89–1.48 (5H, m), 1.43 (3H, d, J 7.1 Hz), and 1.24–1.09 (2, m); and trans-(RS)-4-(hydroxymethyl)-N-{1-[3,5-bis(trifluoromethyl)phenyl]ethyl}-1-phenylcyclohexanecarboxamide (34 mg, 18%), $^1$H NMR (400 MHz, CD$_3$OD) δ 7.73 (1H, s), 7.61 (2H, s), 7.44 (2H, d, J 7.5 Hz), 7.34 (2H, t, J 7.5 Hz), 7.23 (1H, t, J 7.5 Hz), 5.03 (1H, q, J 7.0 Hz), 3.29 (2H, d, J 6.6 Hz), 2.68 (1H, m), 1.90 (2H, m), (2H, m), 1.72 (2H, m), 1.56 (1H, m), 1.39 (3H, d, J 7.0 Hz), 1.20 (1H, m), and 1.07 (1H, m).

The following compound was prepared from trans-(RS)-β-[(4-methylamino-1-phenylcyclohexyl)methoxy]-3,5-bis(trifluoromethyl)benzeneethanol (Example 90) and 1H-imidazole-4-acetic acid according to the method of Example 91.

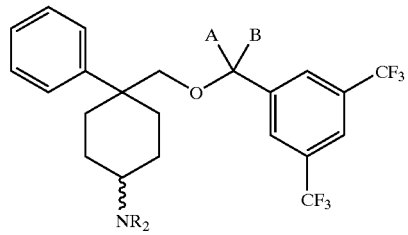

| Ex. | A | B | —NR$_2$ | Stereochemistry | Formula | M.W. | m/z (ES$^+$) (M + 1). |
|---|---|---|---|---|---|---|---|
| 280 | CH$_2$OH | H | (structure with NH imidazole acetamide) | Trans-(RS)- | C$_{29}$H$_{31}$F$_6$N$_3$O$_3$ | 583 | 584 |

The following compounds were prepared according to the method of Example 45, substituting a suitable ketone for (RS)-β-[(4-oxo-1-phenylcyclohexyl)methoxy]-3,5-bis(trifluoromethyl)benzeneethanol, and a suitable amine for benzylamine, followed by separation of diastereoisomers by chromatography on silica gel.

The following compounds were prepared from trans-(RS)-4-(4-oxopiperidin-1-yl)-1-phenyl-N-{1-[3,5-bis(trifluoromethyl)phenyl]ethyl}cyclohexanecarboxamide (Example 184) according to the method of Example 187, substituting a suitable Grignard reagent for phenylmagnesium bromide.

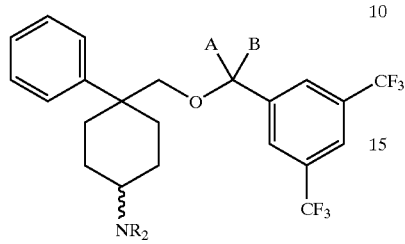

| Ex. | A | B | —NR$_2$ | Stereochemistry | Formula | M.W. | m/z (ES$^+$) (M + 1). |
|---|---|---|---|---|---|---|---|
| 281 | H | H | | Cis-(RS)- | C$_{30}$H$_{35}$F$_6$NO$_2$ | 555 | 556 |
| 282 | H | H | | Trans-(RS)- | C$_{30}$H$_{35}$F$_6$NO$_2$ | 555 | 556 |
| 283 | Me | H | | Trans-(RS)- | C$_{29}$H$_{33}$F$_8$NO | 563 | 564 |
| 284 | Me | H | | Cis-(RS)- | C$_{31}$H$_{37}$F$_6$NO$_2$ | 569 | 570 |
| 285 | Me | H | | Trans-(RS)- | C$_{31}$H$_{37}$F$_6$NO$_2$ | 569 | 570 |
| 286 | Me | H | | Trans-(RS)- | C$_{27}$H$_{30}$F$_6$N$_2$O$_2$ | 528 | 529 |
| 287 | Me | H | | Trans-(RS)- | C$_{33}$H$_{34}$F$_6$N$_2$O$_2$ | 604 | 605 |
| 288 | CH$_2$OH | H | | Cis-(RS)- | C$_{31}$H$_{37}$F$_6$NO$_3$ | 585 | 586 |
| 289 | CH$_2$OH | H | | Trans-(RS)- | C$_{31}$H$_{37}$F$_6$NO$_3$ | 585 | 586 |

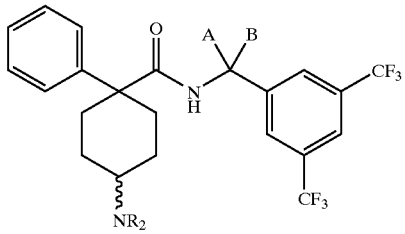

| Ex. | A | B | —NR₂ | Stereochemistry | Formula | M.W. | m/z (ES⁺) (M + 1). |
|---|---|---|---|---|---|---|---|
| 290 | Me | H | piperidine-4-ol with propyl substituent | Trans-(RS)- | $C_{32}H_{40}F_6N_2O_2$ | 598 | 599 |
| 291 | Me | H | piperidine-4-ol with isopropyl substituent | Trans-(RS)- | $C_{31}H_{38}F_6N_2O_2$ | 584 | 585 |
| 292 | Me | H | piperidine-4-ol with isobutyl substituent | Trans-(RS)- | $C_{32}H_{40}F_6N_2O_2$ | 598 | 599 |
| 293 | Me | H | cyclohexane-ol with ethyl substituent | Trans-(RS)- | $C_{30}H_{36}F_6N_2O_2$ | 570 | 571 |

EXAMPLE 294

Cis-(RS)- and Trans-(RS)-1-(4-{2-hydroxy-3-[3,5-bis(trifluoromethyl)phenyl]propyl}-4-phenylcyclohexyl)piperidine Prepared as a 1:1 mixture of diastereoisomers from (RS)-4-{2-hydroxy-3-[3,5-bis(trifluoromethyl)phenyl]propyl}-4-phenylcyclohexanone (Example 25) and piperidine according to the method of Example 45. ¹H NMR (400 MHz, CDCl₃) δ 7.68 (1H, s), 7.50 and 7.48 (Total 2H, each s), 7.4–7.25 (4H, m), 7.25–7.15 (1H, m), 3.80–3.70 and 3.70–3.60 (Total 1H, each m), and 2.75–1.20 (23H, m). m/z (ES⁺) 514 (M+1).

EXAMPLE 295

(RS)-1-(8-Phenyl-1,4-dioxaspiro[4.5]decan-8-yl)-3-[3,5-bis(trifluoromethyl)phenyl]propan-1-ol Potassium carbonate (1.75 g, 12.7 mmol) was added to a solution of (RS)-1-(8-phenyl-1,4-dioxaspiro[4.5]decan-8-yl)-3-[3,5-bis(trifluoromethyl)phenyl]propan-1-yl ethanoate (Example 23, 410 mg, 0.773 mmol) in methanol (15 mL) and water (2 mL) and the mixture was stirred at room temperature for 48 hours, then at 50° C. for 24 hours. The mixture was cooled and the methanol was evaporated under reduced pressure. Water (50 mL) was added and the mixture was extracted with ethyl acetate (2×50 mL). The combined organic fractions were dried (Na₂SO₄) and the solvent was evaporated under reduced pressure to give the title compound (334 mg, 88%). ¹H NMR (400 MHz, CDCl₃) δ 7.68 (1H, s), 7.53 (2H, s), 7.4–7.3 (4H, m), 7.3–7.2 (1H, m), 3.95–3.8 (4H, m), 3.36 (1H, br d, J 9 Hz), 2.91 (1H, ddd, J 14, 10, 5 Hz), 2.64 (1H, ddd, J 16, 9, 7.5 Hz), 2.5–2.4 (1H, m), 2.3–2.2 (1H, m), 1.9–1.7 (3H, m) and 1.65–1.20 (6H, m).

EXAMPLE 296

(RS)-4-{1-Hydroxy-3-[3,5-bis(trifluoromethyl)phenyl]propyl}-4-phenylcyclohexanone Prepared from (RS)-1-(8-phenyl-1,4-dioxaspiro[4.5]decan-8-yl)-3-[3,5-bis(trifluoromethyl)phenyl]propan-1-ol (Example 295) according to the method of Example 10. ¹H NMR (400 MHz, CDCl₃) δ 7.69 (1H, s), 7.51 (2H, s), 7.5–7.4 (4H, m), 7.35–7.25 (1H, m), 3.44 (1H, br d, J 11 Hz), 2.93 (1H, ddd, J 14, 10, 5 Hz), 2.8–2.7 (1H, m), 2.7–2.6 (1H, m), 2.6–2.5 (1H, m), 2.4–2.2 (4H, m), 2.05–1.9 (2H, m), 1.85–1.75 (1H, m), and 1.45–1.3 (2H, m).

EXAMPLE 297

Trans-(RS)-1-(4-{1-hydroxy-3-[3,5-bis(trifluoromethyl)phenyl]propyl}-4-phenylcyclohexyl)piperidine Prepared from (RS)-4-{1-hydroxy-3-[3,5-bis(trifluoromethyl)phenyl]propyl}-4-phenylcyclohexanone (Example 296) and piperidine according to the method of Example 45, followed by separation of diastereoisomers by chromatography on silica gel. ¹H NMR (400 MHz, CDCl₃) δ 7.67 (1H, s), 7.51 (2H, s), 7.4–7.3 (4H, m), 7.3–7.2 (1H, m), 3.30 (1H, br d, J 11 Hz), 2.90 (1H, ddd, J 14, 10, 5 Hz), 2.7–2.55 (2H, m), 2.45–2.3 (8H, m), 1.85–1.75 (3H, m), and 1.7–1.2 (10H, m). m/z (ES+) 514 (M+1).

EXAMPLE 298

Cis-(RS)-4-(4-Fluorophenyl)-1-(4-hydroxy-3-[3,5-bis(trifluoromethyl)phenyl]propyl}-4-phenylcyclohexyl)piperidine; and Trans-(RS)-4-(4-Fluorophenyl)-1-(4-{1-hydroxy-3-[3,5-bis(trifluoromethyl)phenyl]propyl}-4-phenylcyclohexyl)piperidine Prepared from (RS)-4-{1-hydroxy-3-[3,5-bis(trifluoromethyl)phenyl]propyl}-4-phenylcyclohexanone (Example 296) and 4-(4-fluorophenyl)piperidine (Description 16) according to the method of Example 45, followed by separation by flash column chromatography on silica gel, eluting with $CH_2Cl_2/MeOH/NH_3(Aq.)$ (97.5:2.5:0.25 increasing to 95:5:0.5), to give cis-(RS)-4-(4-fluorophenyl)-1-(4-{1-hydroxy-3-[3,5-bis(trifluoromethyl)phenyl]propyl}-4-phenylcyclohexyl)piperidine; $^1$H NMR (400 MHz, $CDCl_3$) δ 7.68 (1H, s), 7.58 (2H, s), 7.4–7.3 (4H, m), 7.3–7.25 (1H, m), 7.25–7.15 (2H, m), 6.99 (2H, t, J 9 Hz), 3.85 (1H, br d, J 10 Hz), 3.25–3.05 (2H, m), 2.95–2.85 (1H, m), 2.78–2.62 (2H, m), 2.50 (1H, quin, J7 Hz), 2.45–2.15 (4H, m), 1.9–1.4 (12H, m), and 1.2–1.08 (1H, m); m/z (ES+) 608 (M+1); and. trans-(RS)-4-(4-fluorophenyl)-1-(4-{1-hydroxy-3-[3,5-bis(trifluoromethyl)phenyl]propyl}-4-phenylcyclohexyl)piperidine; $^1$H NMR (400 MHz, $CDCl_3$) δ 7.67 (1H, s), 7.52 (2H, s), 7.4–7.3 (4H, m), 7.3–7.2 (1H, m), 7.13 (2H, dd, J 8.7, 5.5 Hz), 6.94 (2H, t, J 8.7 Hz), 3.31 (1H, br d, J 10.5 Hz), 3.0–2.85 (3H, m), 2.69–2.58 (2H, m), 2.55–2.35 (3H, m), 2.3–2.1 (2H, m), 1.9–1.5 (9H, m), and 1.4–1.2 (4H, m); m/z (ES+) 608 (M+1).

EXAMPLE 299

Trans-4-(4-Fluorophenyl)-1-(4-{1-oxo-3-[3,5-bis(trifluoromethyl)phenyl]propyl}-4-phenylcyclohexyl)piperidine 1,1,1-Tris(acetyloxy)-1,1-dihydro-1,2-benziodoxol-3(1H)-one (28 mg, 0.066 mmol) was added to a solution of trans-(RS)-4-(4-fluorophenyl)-1-(4-{1-hydroxy-3-[3,5-bis(trifluoromethyl)phenyl]propyl}-4-phenylcyclohexyl)piperidine (Example 298, 14 mg, 0.023 mmol) in dichloromethane (2 mL) and the mixture was stirred at room temperature for 2 hours. Saturated aqueous sodium bisufite (1 mL) and aqueous sodium hydrogen carbonate (5%, 15 mL) were added and the mixture was stirred at room temperature for 20 minutes. The layers were separated and the aqueous layer was extracted with dichloromethane (2 mL). The combined organic fractions were poured onto an SCX cartridge (Varian Bond Elut™; 10 mL/500 mg). The cartridge was washed with methanol (4×2 mL), then eluted with methanolic ammonia (2M, 2×2 mL). The solvent was evaporated under reduced pressure to give the title compound (13.1 mg, 94%). $^1$H NMR (400 MHz, $CDCl_3$) δ 7.61 (1H, s), 7.35 (2H, s), 7.28–7.08 (7H, m), 6.95 (2H, t, J 9 Hz), 2.95 (2H, br d, J 11 Hz), 2.80 (2H, t, J 7 Hz), 2.6–2.5 (2H, m), 2.54 (2H, t, J 7 Hz), 2.45–2.30 (2H, m), 2.15 (2H, t, J 11 Hz), 1.9–1.5 (8H, m), and 1.5–1.35 (2H, m). m/z (ES+) 606 (M+1).

EXAMPLE 300

(RS)-1-(4-Oxo-1-phenylcyclohexyl)-3-[3,5-bis(trifluoromethyl)phenyl]propan-2-yl Ethanoate Prepared from (RS)-1-(8-phenyl-1,4-dioxaspiro[4.5]decan-8-yl)-3-[3,5-bis(trifluoromethyl)phenyl]propan-2-yl ethanoate (Example 23) according to the method of Example 10. $^1$H NMR (400 MHz, $CDCl_3$) δ 7.69 (1H, s), 7.38 (2H, s), 7.36–7.20 (5H, m), 4.95–4.85 (1H, m), 2.73 (1H, dd, J 14, 7 Hz), 2.62–2.47 (2H, m), 2.46 (1H, dd, J 14, 6 Hz), 2.35–2.20 (4H, m), 2.02 (1H, dd, J 14, 7 Hz), 1.95–1.80 (2H, m), 1.77 (1H, dd, J 14, 3 Hz), and 1.75 (3H, m).

EXAMPLE 301

Trans-(RS)-1-{4-[4-(4-Fluorophenyl)piperidin-1-yl]-1-phenylcyclohexyl}-3-[3,5-bis(trifluoromethyl)phenyl]propan-2-yl Ethanoate Prepared from (RS)-1-(4-oxo-1-phenylcyclohexyl)-3-[3,5-bis(trifluoromethyl)phenyl]propan-2-yl ethanoate (Example 300) and 4-(4-fluorophenyl)piperidine (Description 16) according to the method of Example 45, followed by separation of diastereoisomers by flash column chromatography on silica gel, eluting with $CH_2Cl_2/MeOH$ (95:5). $^1$H NMR (400 MHz, $CDCl_3$) δ 7.68 (1H, s), 7.36 (2H, s), 7.32–7.10 (7H, m), 6.92 (2H, t, J 9 Hz), 4.92–4.82 (1H, m), 3.01 (2H, br d, J 9 Hz), 2.66 (1H, dd, J 14, 7 Hz), 2.6–2.2 (6H, m), 2.40 (1H, dd, J 14, 6 Hz), 2.10–1.70 (7H, m), 1.74 (3H, s, 1.64 (1H, dd, J 14, 3 Hz), and 1.55–1.22 (4H, m). m/z (ES+) 650 (M+1).

What is claimed is:
1. A compound of the formula (I):

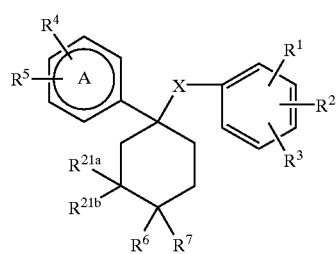

(I)

wherein
ring A is a phenyl ring;
X represents a linker which is:

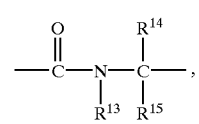

(a)

$R^1$ represents hydroxy, $C_{1-6}$alkyl, fluoro$C_{1-6}$alkyl, $C_{2-6}$alkenyl, $C_{3-7}$cycloalkyl, $C_{3-7}$cycloalkyl$C_{1-4}$alkyl, $C_{1-6}$alkoxy, fluoro$C_{1-6}$alkoxy, $C_{1-6}$alkoxy$C_{1-4}$alkyl, $C_{1-6}$alkoxy$C_{1-4}$alkoxy, fluoro$C_{1-6}$alkoxy$C_{1-4}$alkyl, $C_{2-6}$alkenyloxy, $C_{3-7}$cycloalkoxy, $C_{3-7}$cycloalkyl$C_{1-4}$alkoxy, phenoxy, cyano, halogen, $NR^aR^b$, $SR^a$, $SOR^a$, $SO_2R^a$, $OSO_2R^a$, $NR^aCOR^c$, $COR^a$, $CO_2R^a$ or $CONR^aR^b$ where $R^a$ and $R^b$ each independently represent hydrogen, $C_{1-4}$alkyl, $C_{3-5}$cycloalkyl, fluoro$C_{1-4}$alkyl or $CH_2CO_2C_{1-4}$alkyl, and $R^c$ represents $C_{1-6}$alkyl, $C_{1-6}$alkoxy, fluoro$C_{1-6}$alkyl or phenyl;

$R^2$ represents hydrogen, halogen, $C_{1-6}$alkyl or $C_{1-6}$alkoxy;

$R^3$ represents hydrogen, halogen, $C_{1-6}$alkyl, fluoro$C_{1-6}$alkyl, $C_{1-6}$alkoxy, fluoro$C_{1-6}$alkoxy, $C_{3-7}$cycloalkyl, $C_{3-7}$cycloalkyl$C_{1-4}$alkyl, cyano, $SR^a$, $SOR^a$, $SO_2R^a$, $NR^aR^b$, $NR^aCOR^{14}$, $COR^a$, $CO_2R^a$, $CONR^aR^b$ or $C_{1-4}$alkyl substituted by cyano, $CO_2R^a$ or $CONR^aR^b$ where $R^a$ and $R^b$ are as previously defined;

$R^4$ is hydrogen, halogen, $C_{1-6}$alkyl, $C_{1-6}$alkoxy, fluoro$C_{1-6}$alkyl, fluoro$C_{1-6}$alkoxy, hydroxy, $NO_2$, CN, $SR^a$, $SOR^a$, $SO_2R^a$, $CO_2R^a$, $CONR^2R^b$, $C_{2-6}$alkenyl, $C_{2-6}$alkynyl or $C_{1-4}$alkyl substituted by $C_{1-4}$alkoxy, wherein $R^a$ and $R^b$ are as previously defined;

$R^5$ is hydrogen, halogen, $C_{1-6}$alkyl, fluoro$C_{1-6}$alkyl or $C_{1-6}$alkoxy substituted by $C_{1-4}$alkoxy;

$R^6$ represents hydrogen, hydroxy or a $C_{1-4}$alkyl group optionally substituted by a hydroxy group;

$R^7$ represents hydrogen, hydroxy, $-(CH_2)_nNR^8R^9$, $-(CH_2)_nCO_2R^a$, or carbocyclyl;

or $R^6$ and $R^7$ together represent $=O$, $=CHCO_2R^a$ or $-O(CH_2)_mO-$;

$R^8$ and $R^9$ each independently represent hydrogen, $C_{1-6}$alkyl, $C_{2-6}$alkenyl, hydroxy$C_{1-6}$alkyl, $(CH_2)_qC_{3-7}$cycloalkyl, $(CH_2)_q$aryl, CHO, $C(O)C_{1-6}$alkyl, $C(O)(CH_2)_qC_{3-7}$cycloalkyl, $C(O)(CH_2)_q$aryl, $C(O)(CH_2)_pNR^aR^b$, $(CH_2)_qCO_2C_{1-6}$alkyl, $CO_2(CH_2)_qC_{3-7}$cycloalkyl, $CO_2(CH_2)_q$aryl, $CO_2(CH_2)_pNR^aR^b$, $(CH_2)_pNR^aCOR^b$, $(CH_2)_pNR^aCO_2R^b$, or $(CH_2)_qCONR^a$aryl where $R^a$ and $R^b$ are as previously defined;

or $R^8$ and $R^9$, together with the nitrogen atom to which they are attached, represent a heteroaliphatic ring selected from the group consisting of:

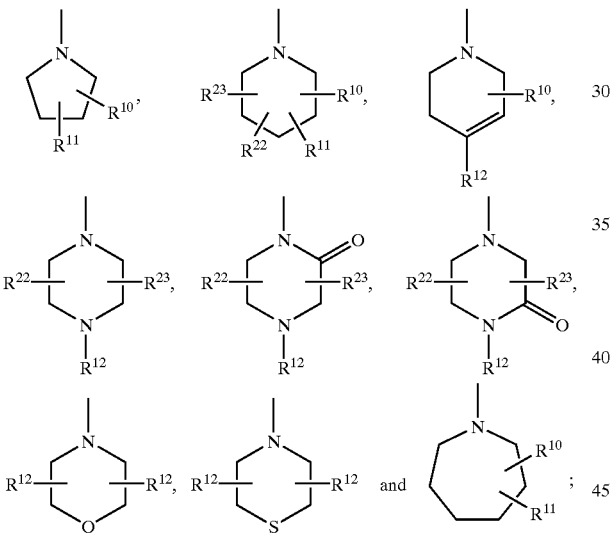

$R^{10}$ and $R^{11}$ each independently represent hydrogen, halogen, hydroxy, $C_{1-6}$alkyl, $C_{2-6}$alkenyl, $C_{2-6}$alkynyl, hydroxy$C_{1-6}$alkyl, fluoro$C_{1-6}$alkyl, $C_{1-6}$alkoxy, $(CH_2)_qC_{3-7}$cycloalkyl, $(CH_2)_q$aryl, $(C_{2-6}$alkenyl)aryl, $(C_{2-6}$alkynyl)aryl, $(CH_2)_q$heterocyclyl, $(CH_2)_pNR^aR^b$, $O(CH_2)_qC_{3-7}$cycloalkyl, $O(CH_2)_q$aryl, $O(CH_2)_q$heterocyclyl, $O(CH_2)_pNR^aR^b$, $OC(O)C_{1-6}$alkyl, $C(O)C_{1-6}$alkyl, $C(O)(CH_2)_q$aryl, $C(O)(CH_2)_q$heterocyclyl, $C(O)(CH_2)_pNR^aR^b$, $CO_2H$, $CO_2C_{1-6}$alkyl, $CO_2(CH_2)_qC_{3-7}$cycloalkyl, $CO_2(CH_2)_q$aryl, $CO_2(CH_2)_q$heterocyclyl or $CO_2(CH_2)_pNR^aR^b$, where $R^a$ and $R^b$ are as previously defined;

or, when they are attached to the same carbon atom, $R^{10}$ and $R^{11}$ may together represent $=O$, $=CHCO_2R^a$, $-O(CH_2)_mO-$, $-CH_2O(CH_2)_s-$, $-CH_2OCH_2C(O)-$, $-CH_2OCH_2CH(OH)-$, $-CH_2OCH_2C(CH_3)_2-$, $-CH_2OC(CH_3)_2CH_2-$, $-C(CH_3)_2OCH_2CH_2-$, $-CH_2C(O)OCH_2-$, $-OC(O)CH_2CH_2-$, $-C(O)OCH_2CH_2-$, $-C(O)OC$ $(CH_3)_2CH_2-$, $-C(O)OCH_2C(CH_3)_2-$, $-OCH_2$ $(CH_2)_s-$, $-OC(CH_3)_2CH_2CH_2-$, $-OCH_2C(CH_3)_2$ $CH_2-$, $-OCH_2CH_2C(CH_3)_2-$, $-OCH_2CH=CHCH_2-$, $-OCH_2CH(OH)CH_2CH_2-$, $-OCH_2CH_2CH(OH)CH_2-$, $-OCH_2C(O)CH_2CH_2-$, $-OCH_2CH_2C(O)CH_2-$, or a group of the formula

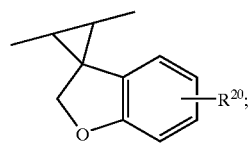

or, where they are attached to adjacent carbon atoms, $R^{10}$ and $R^{11}$ may together represent $-OCH_2CH_2-$ or $-OCH_2CH(OH)-$, or $R^{10}$ and $R^{11}$ may together form a fused benzene ring;

or, $R^{10}$ and $R^{11}$ together form a $C_{1-2}$alkylene bridge across the pyrrolidine, piperidine or hexamethyleneimine ring to which they are attached;

$R^{12}$ represents hydrogen, $C_{1-6}$alkyl, $(CH_2)_qC_{3-7}$cycloalkyl, $(CH_2)_q$aryl, CHO, $C(O)C_{1-6}$alkyl, $C(O)(CH_2)_qC_{3-7}$cycloalkyl, $C(O)(CH_2)_q$aryl, $CO_2C_{1-6}$alkyl, $CO_2(CH_2)_qC_{3-7}$cycloalkyl, $CO_2(CH_2)_q$aryl, or $CO_2(CH_2)_pNR^aR^b$, where $R^a$ and $R^b$ are as previously defined;

$R^{13}$ represents hydrogen, $C_{1-6}$alkyl or $C(O)C_{1-6}$alkyl;

$R^{14}$, $R^{15}$, $R^{16}$, $R^{17}$, $R^{18}$ and $R^{19}$ each independently represent hydrogen, hydroxy, $C_{1-6}$alkyl, $C_{1-6}$alkenyl, hydroxy$C_{1-6}$alkyl, $C_{1-4}$alkoxy$C_{1-4}$alkyl, $(CH_2)_pNR^aR^b$, CHO, $C(O)C_{1-6}$alkyl or $CO_2C_{1-6}$alkyl;

or, $R^{14}$ and $R^{15}$ together represent $-CH_2CH_2-$;
or, $R^{16}$ and $R^{17}$ together represent $-CH_2CH_2-$;
or, $R^{18}$ and $R^{19}$ together represent $-CH_2CH_2-$;

$R^{20}$ represents hydrogen, halogen, hydroxy, $C_{1-4}$alkyl, hydroxy$C_{1-4}$alkyl or fluoro$C_{1-4}$alkyl;

$R^{21a}$ represents hydrogen, halogen or hydroxy and $R^{21b}$ represents hydrogen;

or $R^{21a}$ and $R^{21b}$ both represent fluorine or together represent oxo ($=O$);

$R^{22}$ and $R^{23}$ each independently represent hydrogen, halogen, hydroxy, $C_{1-6}$alkyl or oxo ($=O$);

n is zero, 1 or 2;
m is 1 or 2;
p is 1, 2, 3 or 4;
q is zero, 1, 2, 3 or 4; and
s is 1, 2 or 3;

or a pharmaceutically acceptable salt or N-oxide thereof.

2. The compound of claim 1 wherein $R^1$ is hydroxy, $C_{1-6}$alkyl, fluoro$C_{1-6}$alkyl, $C_{2-6}$alkenyl, $C_{1-6}$alkoxy, fluoro$C_{1-6}$alkoxy, $C_{2-6}$alkenyloxy, $C_{3-7}$cycloalkoxy, $C_{3-7}$cycloalkyl$C_{1-4}$alkoxy, cyano, $NR^aR^b$, $SR^a$, $OSO_2R^a$.

3. The compound of claim 1 wherein $R^2$ a hydrogen, fluorine or chlorine atom.

4. The compound of claim 1 wherein $R^3$ is hydrogen, halogen, fluoro$C_{1-6}$alkyl, fluoro$C_{1-6}$alkoxy, cyano, $NR^aR^b$, $NR^aCOR^d$ (where $R^d$ is methyl, methoxy, trifluoromethyl or phenyl).

5. The compound of claim 1 wherein $R^4$ is hydrogen.

6. The compound of claim 1 wherein $R^5$ is hydrogen, fluorine, chlorine or $CF_3$.

7. The compound of claim 1 wherein $R^6$ is hydrogen.

8. The compound of claim 1 wherein $R^7$ is hydroxy, $-(CH_2)_nNR^8R^9$ or $R^6$ and $R^7$ together represent $=O$, $-O(CH_2)_mO-$ or $-CH_2OCH_2C(O)-$.

9. The compound of claim 1 wherein $R^8$ represents hydrogen, $C_{1-6}$alkyl, $C_{2-6}$alkenyl, hydroxy$C_{1-6}$alkyl, $(CH_2)_q$ $C_{3-7}$cycloalkyl, $(CH_2)_q$aryl, $C(O)C_{1-6}$alkyl, $C(O)(CH_2)_q$ aryl, $C(O)(CH_2)_p NR^a R^b$, $(CH_2)_q CO_2 C_{1-6}$alkyl, $(CH_2)_p NR^a CO_2 R^b$ or $(CH_2)_q CONR^a$aryl;

and $R^9$ represents hydrogen, $C_{1-6}$alkyl, $(CH_2)_q C_{3-7}$cycloalkyl or $CO_2 C_{1-6}$alkyl;

or $R^8$ and $R^9$ together with the nitrogen atom to which they are attached represent a heteroaliphatic ring selected from the group consisting of:

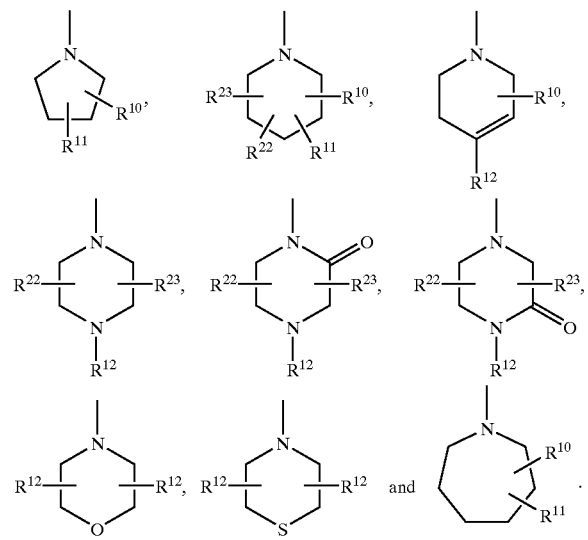

10. The compound of claim 9 wherein $R^{10}$ represents hydrogen, hydroxy, $C_{1-6}$alkyl, $C_{2-6}$alkenyl, $C_{2-6}$alkynyl, hydroxy$C_{1-6}$alkyl, fluoro$C_{1-6}$alkyl, $(C_{2-6}$alkynyl)aryl, $(CH_2)_q$ aryl, $(CH_2)_q$heterocyclyl, $(CH_2)_q NR^a R^b$, $OC(O)C_{1-6}$alkyl, $C(O)(CH_2)_q NR^a R^b$, $CO_2 H$ or $CO_2 C_{1-6}$alkyl;

and $R^{11}$ represents hydrogen, halogen, hydroxy, $C_{1-6}$alkyl or $(CH_2)_q NR^a R^b$.

11. The compound of claim 9 wherein $R^{12}$ represents hydrogen, $C_{1-6}$alkyl, $(CH_2)_q C_{3-7}$cycloalkyl, $(CH_2)_q$aryl, CHO, $C(O)C_{1-6}$alkyl, $C(O)C_{3-7}$cycloalkyl, $C(O)(CH_2)_q$aryl or $CO_2 C_{1-6}$alkyl.

12. The compound of claim 9 wherein the ring A is an unsubstituted phenyl ring.

13. A compound of claim 1 wherein X is a linker which is:

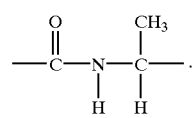

14. The compound of claim 1 of the formula (Ia):

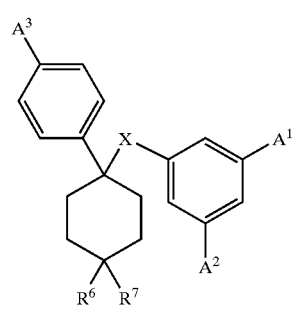

(Ia)

wherein $A^1$ is fluorine or $CF_3$;

$A^2$ is fluorine or $CF_3$;

$A^3$ is fluorine or hydrogen;

X is a linker which is:

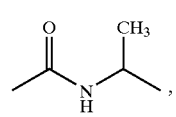

(a)

or a pharmaceutically acceptable salt thereof.

15. The compound of claim 1 wherein the stereochemistry of the 1- and 4-positions is as shown in formula (Ib):

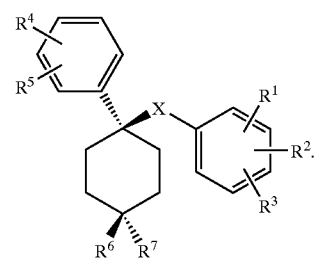

(Ib)

16. A pharmaceutical composition comprising the compound of claim 1 or a pharmaceutically acceptable salt thereof and a pharmaceutically acceptable carrier or excipient.

17. A method for the treatment of pain or inflammation, migraine, emesis, postherpetic neuralgia, depression or anxiety which method comprises administration to a patient in need thereof of an effective amount of the compound of claim 1 or a pharmaceutically acceptable salt thereof.

* * * * *